US010206999B2

(12) United States Patent
Suarez et al.

(10) Patent No.: US 10,206,999 B2
(45) Date of Patent: Feb. 19, 2019

(54) ANTIBODIES AGAINST LIF AND USES THEREOF

(71) Applicants: MOSAIC BIOMEDICALS, S.L., Barcelona (ES); FUNDACIÓ PRIVADA INSTITUT D'INVESTIGACIÓ ONCOLÓGICA DE VALL HEBRON, Barcelona (ES); FUNDACIÓ PRIVADA INSTITUCIÓ CATALANA DE RECERCA I ESTUDIS AVANÇATS, Barcelona (ES)

(72) Inventors: Joan Seoane Suarez, Barcelona (ES); Judit Anido Folgueira, Barcelona (ES)

(73) Assignees: Mosaic Biomedicals, S.L., Barcelona; Fundació Privada Institut d'Investigació Oncológica de Vall Hebron, Barcelona; Fundació Privada Institució Catalana de Recerca I Estudis Avançats, Barcelona ( * ) Notice: Subject to any disclaimer, the term of this patent is extended or adjusted under 35 U.S.C. 154(b) by 0 days.

(21) Appl. No.: 15/880,906

(22) Filed: Jan. 26, 2018

(65) Prior Publication Data

US 2018/0169233 A1  Jun. 21, 2018

Related U.S. Application Data

(62) Division of application No. 15/845,614, filed on Dec. 18, 2017.

(60) Provisional application No. 62/467,017, filed on Mar. 3, 2017.

(30) Foreign Application Priority Data

Dec. 19, 2016  (EP) .................................... 16382617
Oct. 13, 2017  (EP) .................................... 17382683

(51) Int. Cl.

| | |
|---|---|
| *C07K 16/24* | (2006.01) |
| *A61K 39/395* | (2006.01) |
| *A61P 35/02* | (2006.01) |
| *A61P 35/00* | (2006.01) |
| *A61K 9/00* | (2006.01) |
| *C07K 16/28* | (2006.01) |
| *A61K 39/00* | (2006.01) |

(52) U.S. Cl.
CPC ...... *A61K 39/39558* (2013.01); *A61K 9/0085* (2013.01); *A61K 39/3955* (2013.01); *A61P 35/00* (2018.01); *A61P 35/02* (2018.01); *C07K 16/244* (2013.01); *C07K 16/248* (2013.01); *C07K 16/2896* (2013.01); *A61K 2039/505* (2013.01); *A61K 2039/55527* (2013.01); *C07K 2317/24* (2013.01); *C07K 2317/33* (2013.01); *C07K 2317/34* (2013.01); *C07K 2317/567* (2013.01); *C07K 2317/76* (2013.01); *C07K 2317/92* (2013.01)

(58) Field of Classification Search
CPC ................ C07K 2317/24; C07K 16/22; C07K 2317/73; C07K 14/47; C07K 14/00; C07K 2319/33; C12P 21/02; C12P 13/00; C12P 13/005; A61K 2039/505; A61K 38/17; C12N 15/67; C12N 9/93; C12N 15/1086; C12N 15/1093; C07H 21/04; G01N 33/583; G01N 33/6854; G01N 33/6893
See application file for complete search history.

(56) References Cited

U.S. PATENT DOCUMENTS

| | | | |
|---|---|---|---|
| 5,624,821 | A | 4/1997 | Winter et al. |
| 5,648,260 | A | 7/1997 | Winter et al. |
| 5,654,157 | A | 8/1997 | Kim |
| 5,980,894 | A | 11/1999 | Kim |
| 7,084,257 | B2 | 8/2006 | Deshpande et al. |
| 7,550,569 | B2 | 6/2009 | Baker et al. |
| 7,993,869 | B2 | 8/2011 | Drijfhout et al. |
| 8,926,956 | B2 | 1/2015 | Suarez et al. |
| 8,974,785 | B2 | 3/2015 | Li et al. |
| 9,194,872 | B2 | 11/2015 | Chang et al. |
| 9,322,067 | B2 | 4/2016 | Von et al. |
| 2005/0014934 | A1 | 1/2005 | Hinton et al. |
| 2011/0135645 | A1 | 6/2011 | Williamson et al. |
| 2012/0114671 | A1 | 5/2012 | Seoane et al. |
| 2012/0315244 | A1 | 12/2012 | Yuan et al. |
| 2014/0271676 | A1 | 9/2014 | Pan et al. |
| 2014/0294867 | A1 | 10/2014 | Pan et al. |
| 2014/0314741 | A1 | 10/2014 | Wu et al. |
| 2015/0056195 | A1 | 2/2015 | Bertolotto-Ballotti |
| 2015/0079070 | A1 | 3/2015 | Pan et al. |

(Continued)

FOREIGN PATENT DOCUMENTS

| | | |
|---|---|---|
| CN | 101440128 A | 5/2009 |
| WO | WO-9323556 A1 | 11/1993 |

(Continued)

OTHER PUBLICATIONS

Seoane, Joan. "Everything you always wanted to know about creating a company (but were afraid to ask)." Published Jan. 4, 2016, 32 pages. http://www.slideshare.net/icrea/everything-you-always-wanted-to-know-about-creating-a-company-but-were-afraid-to-ask.
Adams, et al. PHENIX: a comprehensive Python-based system for macromolecular structure solution. Acta crystallographica. Section D, Biological crystallography. 66:213-221, 2010.
Al-Lazikani et al., Standard conformations for the canonical structures of immunoglobulins. JMB 273:927-948, 1997.
Boulanger, et al., Convergent mechanisms for recognition of divergent cytokines by the shared signaling receptor gp130. Molecular cell. 12:577-589, 2003.

(Continued)

Primary Examiner — Bridget E Bunner
Assistant Examiner — Fozia M Hamud
(74) Attorney, Agent, or Firm — Wilson Sonsini Goodrich & Rosati

(57) ABSTRACT

Described herein are antibodies that target Leukemia Inhibitory Factor (LIF). Also described herein are uses of these antibodies for the treatment of cancer.

17 Claims, 22 Drawing Sheets

Specification includes a Sequence Listing.

(56) References Cited

U.S. PATENT DOCUMENTS

| | | |
|---|---|---|
| 2015/0098947 A1 | 4/2015 | Imhof et al. |
| 2015/0139989 A1 | 5/2015 | Suarez et al. |
| 2016/0060354 A1 | 3/2016 | Avila et al. |

FOREIGN PATENT DOCUMENTS

| | | |
|---|---|---|
| WO | WO-9323665 A1 | 11/1993 |
| WO | WO-9429351 A2 | 12/1994 |
| WO | WO-9633740 A1 | 10/1996 |
| WO | WO-2010115868 A2 | 10/2010 |
| WO | WO-2011057144 A2 | 5/2011 |
| WO | WO-2011124566 A1 | 10/2011 |
| WO | WO-2015025786 A1 | 2/2015 |
| WO | WO-2015040243 A2 | 3/2015 |
| WO | WO-2015106080 A2 | 7/2015 |
| WO | WO-2016040657 A1 | 3/2016 |
| WO | WO-2017089614 A1 | 6/2017 |

OTHER PUBLICATIONS

Chowdhury, Engineering hot spots for affinity enhancement of antibodies. Methods Mol. Biol. 207:179-196, 2008.

Clackson et al., Making antibody fragments using phage display libraries. Nature, 352:624-628, 1991.

Cunningham and Wells, High-resolution epitope mapping of hGH-receptor interactions by alanine-scanning mutagenesis. Science, 244(4908):1081-1085, 1989.

Duncan and Winter, The binding site for Clq and IgG. Nature, 322:738-40, 1988.

Emsley et al., Features and development of Coot. Acta crystallographica. Section D, Biological crystallography. 66:486-50, 2010.

European Patent Application No. 16382617.5 extended European Search Report dated Oct. 20, 2017.

Honegger and Plückthun, Yet another numbering scheme for immunoglobulin variable domains: An automatic modeling and analysis tool, J Mol Biol, 309(3):657-670, 2001.

Hoogenboom et al., Overview of antibody phage-display technology and its applications. In: Methods in Molecular Biology, vol. 178:1-37, 2001.

Kabsch et al., XDS. Acta crystallographica. Section D, Biological crystallography 66:125-132, 2010.

Kim et al., Detection of human leukemia inhibitory factor by monoclonal antibody based ELISA. Journal of Immunological Methods, 156:9-17, 1992.

Lefranc et al.,IMGT unique numbering for immunoglobulin and T cell receptor variable domains and Ig superfamily V-like domains. Dev Comp Immunol, 27(1):55-77, 2003.

MacCallum et al., Antibody-antigen interactions: contact analysis and binding site topography.. J. Mol. Biol. 262:732-745, 1996.

McCoy et al., Phaser crystallographic software. J Appl Crystallogr 40:658-674, 2007.

Portolano et al., Lack of promiscuity in autoantigen-specific H and L chain combinations as revealed by human H and L chain "roulette". J. Immunol. 150:880-887, 1993.

Penuelas et al., TGF-Beta increases glioma-initiating cell self-renewal through the induction of LIF in human glioblastoma. Cancer Cell, 15:315-327, 2009 and Supplemental Data, 15 pages.

Seoane, Joan. "Everything you always wanted to know about creating a company (but were afraid to ask)." Published Dec. 22, 2016, 32 pages. http://www.slideshare.net/icrea/everthing-you-always-wanted-to-know-about-creating-a-company-but-were-afraid-to-ask.

Hyman et al., A Phase 1, First-in-human, open label, dose escalation, dose expansion study of MSC-1, a humanized anti-LIF monoclonal antibody, in patients with relapsed/refractory metastatic solid tumors (Abstract). Northern Biologics, Nov. 2, 2017, 1 page.

Hyman et al., Poster: A Phase 1, First-in-human, open label, dose escalation, dose expansion study of MSC-1, a humanized anti-LIF monoclonal antibody, in patients with relapsed/refractory metastatic solid tumors. Northern Biologics, Nov. 11, 2017, 1 page.

Magram et al., LIF as a novel cancer immunotherapy target: modulating the tumor microenvironment with MSC-1, a humanized anti-LIF monoclonal antibody (Abstract). In: Proceedings of the AACR-NCI-EORTC International Conference: Molecular Targets and Cancer Therapeutics: Oct. 26-30, 2017; Philadelphia, PA.: AACR; Mol Cancer Ther 17(1 Supp): Abstract nr LB-B34, 2018.

Magram et al., Poster: LIF as a novel cancer immunotherapy target: modulating the tumor microenvironment with MSC-1, a humanized anti-LIF monoclonal antibody. Northern Biologics, Oct. 29, 2017, 1 page.

U.S. Appl. No. 15/845,614, filed Dec. 18, 2017.

PCT Patent Application No. PCT/IB2017/001677 filed Dec. 18, 2017.

PCT/IB2017/001677 International Search Report and Written Opinion dated Apr. 20, 2018.

Li et al. LIF promotes tumorigenesis and metastasis of breast cancer through the AKT-mTOR pathway. Oncotarget 5(3):788-801 (2014).

Tu et al. Leukemia inhibitory factor (LIF) antinociception activity and inhibits tolerance induction of opioids.Br J Anaesth 117(4):512-520 (2016).

Yamashita et al. Effect of novel monoclonalantibodies on LIF-induced signaling in chicken blastodermal cells. Dev Comp Immunol 30(5):513-522 (2006).

Deckers, S. et al. CD44 Loss of Function in Spontaneous Murine Glioma Implicates CD44 in Tumor Maintenance. (Abstract No. 61) Neuro-Oncology, p. 578. Oct. 1, 2009.

Farhad Ravandi and Zeev Estrov. The Role of Leukemia Inhibitory Factor in Cancer and Cancer Metastatis. Cancer Metastasis Biology and Treatment Growth Factors and Their Receptors in Cancer Metastasis. vol. 2, pp. 1-25 (Jan. 1, 2004).

Godard, A. et al. Generation of monoclonal antibodies against HILDA/LIF and their use in the quantitative assay of the cytokine. Cytokine. Jan. 1993;5(1):16-23.

Hirobe, Tomohisa. Role of leukemia inhibitory factor in the regulation of the proliferation and differentiation of neonatal mouse epidermal melanocytes in culture.J Cell Physiol. Sep. 2002;192(3):315-26.

Huang, C. et al. Evaluation of the prognostic value of CD44 in glioblastoma multiforme. Anticancer Res. Jan. 2010;30(1):253-9.

Hudis. Trastuzumab—mechanism of action and use in clinical practice. N. Engl J Med. Jul. 5, 2007;357(1):39-51.

Kamohara, H. et al. Leukemia inhibitory factor functions as a growth factor in pancreas carcinoma cells: Involvement of regulation of LIF and its receptor expression. Int J Oncol. Apr. 2007;30(4):977-83.

Kellokumpu-Lehtinen, P. et. al. Leukemia-inhibitory factor stimulates breast, kidney and prostate cancer cell proliferation by paracrine and autocrine pathways. Int J Cancer. May 16, 1996;66(4):515-9. 0.

Northern Biologics, BioCentury NewsMakers, Sep. 8, 2017, pp. 1-13.

Northern Biologics, Bloom, Burton & Co. Healthcare Investor Conference, May 2, 2017, pp. 1-21.

Northern Biologics Investor Presentation, Sep. 2017, pp. 1-19.

Northern Biologics, Investor Deck, Bio-Europe, Nov. 6, 2017, pp. 1-15.

Northern Biologics, Investor Deck, BioInvestor Forum, Oct. 17, 2017, pp. 1-17.

Sengupta, J. et al. Monoclonal anti-leukemia inhibitory factor antibody inhibits blastocyst implantation in the rhesus monkey. Contraception. Nov. 2006;74(5):419-25. Epub Jul 17, 2006.

Soroceanu, L. et al. Id-1 is a Key Transcriptional Regulator of Glioblastoma Aggressiveness and a Novel Therapeutic Target. Cancer Res. Mar. 1, 2013; 73(5): 1559-1569.

Towle, M.F. et al. Deprivation of leukemia inhibitory factor by its function-blocking antibodies augments T cell activation. J Interferon Cytokine Res. Jun. 1998;18(6):387-92.

Tsuchiya, Takeshi et al. Targeting Id1 and Id3 inhibits peritoneal metastasis of gastric cancer. Cancer Sci. Nov. 2005;96(11):784-90.

Seoane, Joan. Everything you always wanted to know about creating a company (but were afraid to ask). Published Dec. 22, 2015, pp. 1-32. http://www.slideshare.net/icrea/everything-you-always-wanted-to-know-about-creating-a-company-but-we.

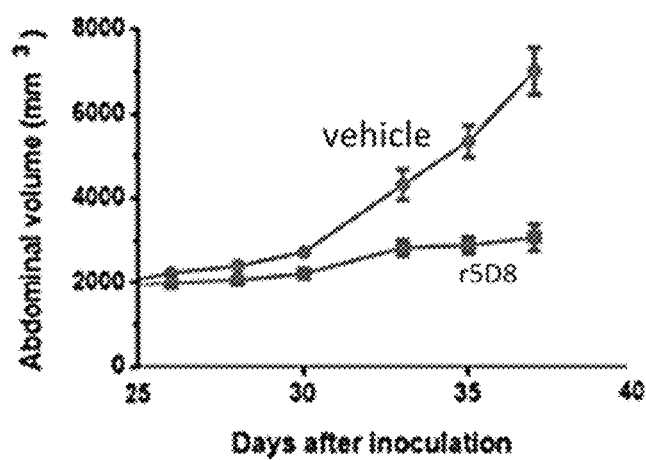
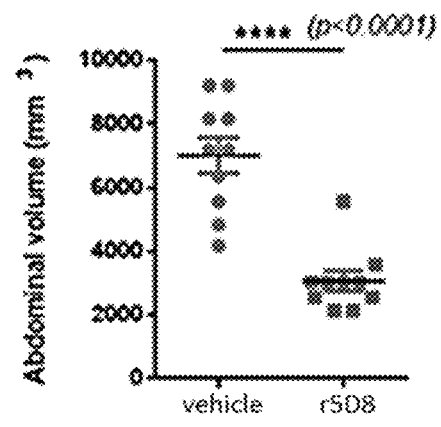
Fig. 8A
Fig. 8B
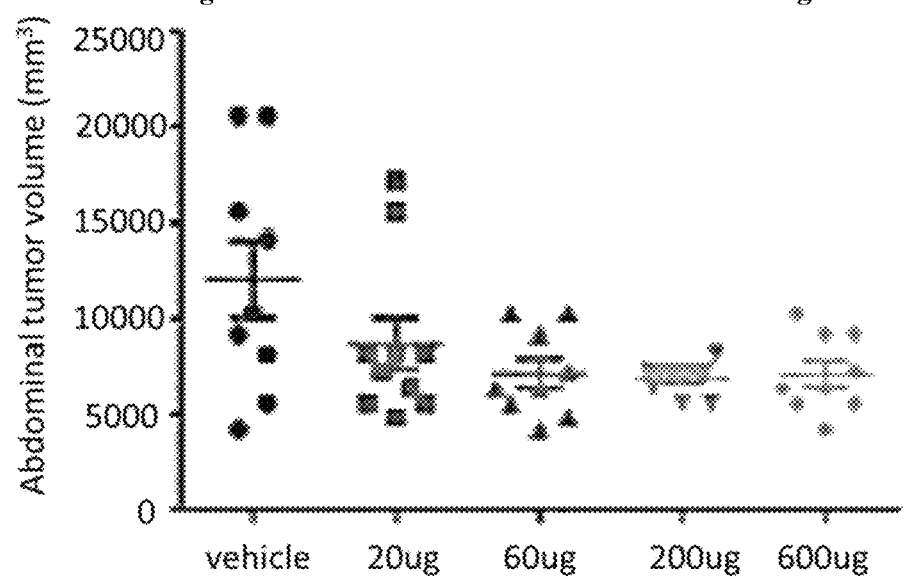
Fig. 8C

ANTIBODIES AGAINST LIF AND USES THEREOF

CROSS REFERENCE TO RELATED APPLICATIONS

This application is a divisional of U.S. patent application Ser. No. 15/845,614, filed Dec. 18, 2017, entitled "ANTIBODIES AGAINST LIF AND USES THEREOF", which claims priority to European Patent Application No. EP16382617.5 filed on Dec. 19, 2016, U.S. Provisional Patent Application No. 62/467,017 filed on Mar. 3, 2017, and European Patent Application No. EP17382683.5 filed on Oct. 13, 2017, all of which are incorporated by reference herein in their entireties.

SEQUENCE LISTING

The instant application contains a Sequence Listing which has been submitted electronically in ASCII format and is hereby incorporated by reference in its entirety. Said ASCII copy, created on Jan. 31, 2018, is named 48885-704_301_SL.txt and is 84,894 bytes in size.

BACKGROUND

Leukemia inhibitory factor (LIF) is an Interleukin 6 (IL-6)-type cytokine that is involved in a variety of biological activities including the inhibition of cell differentiation. Human LIF is a polypeptide of 202 amino acids that exerts biological effects via binding to the cell surface LIF receptor (LIFR or CD118) which heterodimerizes with gp130. This leads to activation of pro-growth signaling pathways such as the mitogen activated protein kinase (MAPK) and the Janus activated kinase (JAK/STAT) pathway. High expression levels and high serum levels of LIF have been demonstrated to be associated with a poor prognosis for many types of cancer.

SUMMARY

Described herein are novel anti-LIF antibodies that antagonize or block LIF activity. These antibodies are useful for the treatment of cancer. These antibodies can be humanized in order to develop a clinical therapy for cancers that express high levels of LIF, LIF receptor, or exhibit LIF dependent growth. One such antibody described herein exhibits an unexpected improvement in binding affinity and biological effect after the humanization process.

In one aspect, described herein, is a recombinant antibody that specifically binds Leukemia Inhibitory Factor (LIF) comprising: a) a heavy chain complementarity determining region 1 (VH-CDR1) comprising an amino acid sequence set forth in any one of SEQ ID NOs: 1-7 or 33; b) a heavy chain complementarity determining region 2 (VH-CDR2) comprising an amino acid sequence set forth in any one of SEQ ID NOs: 9-13 or 35; c) a heavy chain complementarity determining region 3 (VH-CDR3) comprising an amino acid sequence set forth in any one of SEQ ID NOs: 15-19 or 37; d) a light chain complementarity determining region 1 (VL-CDR1) comprising an amino acid sequence set forth in any one of SEQ ID NOs: 21-23 or 39; e) a light chain complementarity determining region 2 (VL-CDR2) comprising an amino acid sequence set forth in any one of SEQ ID NOs: 25-27 or 41; and f) a light chain complementarity determining region 3 (VL-CDR3) comprising an amino acid sequence set forth in any one of SEQ ID NOs: 29, 30, or 43, wherein the recombinant antibody specifically binds to LIF. In certain embodiments, the recombinant antibody binds to glycosylated LIF. In certain embodiments, the recombinant antibody comprises at least one framework region derived from a human antibody framework region. In certain embodiments, the recombinant antibody is humanized. In certain embodiments, the recombinant antibody is deimmunized. In certain embodiments, the recombinant antibody comprises two immunoglobulin heavy chains and two immunoglobulin light chains. In certain embodiments, the recombinant antibody comprises a Fab, F(ab)$_2$, single-domain antibody, a single chain variable fragment (scFv), or a nanobody. In certain embodiments, the recombinant antibody specifically binds LIF with a dissociation constant ($K_D$) of less than about 200 picomolar. In certain embodiments, the recombinant antibody specifically binds LIF with a dissociation constant ($K_D$) of less than about 100 picomolar. In certain embodiments, the VH-CDR1 comprises an amino acid sequence set forth in SEQ ID NO: 4 (GFTFSNAWMH), wherein the VH-CDR2 comprises an amino acid sequence set forth in SEQ ID NO: 11 (QIKDKSDNYATYYAESVKG), wherein the VH-CDR3 comprises an amino acid sequence set forth in SEQ ID NO: 17 (TCWEWYLDF), wherein the VL-CDR1 comprises an amino acid sequence set forth in SEQ ID NO: 21 (RSSQSLLDSDGHTYLN), wherein the VL-CDR2 comprises an amino acid sequence set forth in SEQ ID NO: 25 (SVSNLES), and wherein the VL-CDR3 comprises an amino acid sequence set forth in SEQ ID NO: 29 (MQATHAPPYT). In certain embodiments, the VH-CDR1 comprises an amino acid sequence set forth in SEQ ID NO: 7 (SKFMY), wherein the VH-CDR2 comprises an amino acid sequence set forth in SEQ ID NO: 13 (WIYPGDGDTEYNQKFSE), wherein the VH-CDR3 comprises an amino acid sequence set forth in SEQ ID NO: 19 (RDYHSSHFAY), wherein the VL-CDR1 comprises an amino acid sequence set forth in SEQ ID NO: 23 (RSSQSLLHNNGNTYLS), wherein the VL-CDR2 comprises an amino acid sequence set forth in SEQ ID NO: 27 (QVSNRFS), and wherein the VL-CDR3 comprises an amino acid sequence set forth in SEQ ID NO: 30 (GQGTQYPYT). In certain embodiments, the VH-CDR1 comprises an amino acid sequence set forth in SEQ ID NO: 33 (TAGMQ), wherein the VH-CDR2 comprises an amino acid sequence set forth in SEQ ID NO: 35 (WINTQSGEPQYVDDFRG), wherein the VH-CDR3 comprises an amino acid sequence set forth in SEQ ID NO: 37 (WALYSEYDVMDY), wherein the VL-CDR1 comprises an amino acid sequence set forth in SEQ ID NO: 39 (KASENVDSYVS), wherein the VL-CDR2 comprises an amino acid sequence set forth in SEQ ID NO: 41 (GASNRYT), and wherein the VL-CDR3 comprises an amino acid sequence set forth in SEQ ID NO: 43 (GQSYRYPPT). In certain embodiments, the VH-CDR1 comprises an amino acid sequence set forth in SEQ ID NO: 1 (GFTFSHAWMH), wherein the VH-CDR2 comprises an amino acid sequence set forth in SEQ ID NO: 9 (QIKAKSDDYATYYAESVKG), wherein the VH-CDR3 comprises an amino acid sequence set forth in SEQ ID NO: 15 (TCWEWDLDF), wherein the VL-CDR1 comprises an amino acid sequence set forth in SEQ ID NO: 21 (RSSQSLLDSDGHTYLN), wherein the VL-CDR2 comprises an amino acid sequence set forth in SEQ ID NO: 25 (SVSNLES), and wherein the VL-CDR3 comprises an amino acid sequence set forth in SEQ ID NO: 29 (MQATHAPPYT). In certain embodiments, the recombinant antibody comprises one or more of a heavy chain framework 1 (VH-FR1) region amino acid sequence at least about 80%, about 90%, or about 95% identical to the amino acid sequence set forth in any one of SEQ ID NOs: 44-47, a heavy chain framework 2 (VH-FR2) region amino acid sequence at least about 80%, about 90%, or about 95% identical to the amino acid sequence set forth in any one of SEQ ID NOs: 48-49, a heavy chain framework 3 (VH-FR3) region amino acid sequence at least about 80%, about 90%, or about 95% identical to the amino acid sequence set forth in any one of SEQ ID NOs: 50-52, and a heavy chain framework 4 (VH-FR4) region amino acid sequence at least about 80%, about 90%, or about 95% identical to the amino acid sequence set forth in any one of SEQ ID NOs: 53-55. In certain embodiments, the recombinant antibody comprises one or more of a light chain framework 1 (VL-FR1) region amino acid sequence at least about 80%, about 90%, or about 95% identical to the amino acid sequence set forth in any one of SEQ ID NOs: 56-59, a light chain framework 2 (VL-FR2) region amino acid sequence at least about 80%, about 90%, or about 95% identical to the amino acid sequence set forth in any one of SEQ ID NOs: 60-63, a light chain framework 3 (VL-FR3) region amino acid sequence at least about 80%, about 90%, or about 95% identical to the amino acid sequence set forth in any one of SEQ ID NOs: 64-67, and a light chain framework 4 (VL-FR4) region amino acid sequence at least about 80%, about 90%, or about 95% identical to the amino acid sequence set forth in any one of SEQ ID NOs: 68-70. In certain embodiments, the recombinant antibody comprises a VH-FR1 amino acid sequence at least about 80%, about 90%, or about 95% identical to the amino acid sequence set forth in SEQ ID NO: 45, a VH-FR2 amino acid sequence at least about 80%, about 90%, or about 95% identical to the amino acid sequence set forth in SEQ ID NO: 49, a VH-FR3 amino acid sequence at least about 80%, about 90%, or about 95% identical to the amino acid sequence set forth in SEQ ID NO: 50, and a VH-FR4 amino acid sequence at least about 80%, about 90%, or about 95% identical to the amino acid sequence set forth in SEQ ID NO: 54. In certain embodiments, the recombinant antibody comprises a VL-FR1 amino acid sequence at least about 80%, about 90%, or about 95% identical to the amino acid sequence set forth in SEQ ID NO: 57, a VL-FR2 amino acid sequence at least about 80%, about 90%, or about 95% identical to the amino acid sequence set forth in SEQ ID NO: 61, a VL-FR3 amino acid sequence at least about 80%, about 90%, or about 95% identical to the amino acid sequence set forth in SEQ ID NO: 65, and a VL-FR4 amino acid sequence at least about 80%, about 90%, or about 95% identical to the amino acid sequence set forth in SEQ ID NO: 68. In certain embodiments, the recombinant antibody comprises a VH-FR1 amino acid sequence at least about 80%, about 90%, or about 95% identical to the amino acid sequence set forth in SEQ ID NO: 45, a VH-FR2 amino acid sequence at least about 80%, about 90%, or about 95% identical to the amino acid sequence set forth in SEQ ID NO: 49, a VH-FR3 amino acid sequence at least about 80%, about 90%, or about 95% identical to the amino acid sequence set forth in SEQ ID NO: 50, a VH-FR4 amino acid sequence at least about 80%, about 90%, or about 95% identical to the amino acid sequence set forth in SEQ ID NO: 54, a VL-FR1 amino acid sequence at least about 80%, about 90%, or about 95% identical to the amino acid sequence set forth in SEQ ID NO: 57, a VL-FR2 amino acid sequence at least about 80%, about 90%, or about 95% identical to the amino acid sequence set forth in SEQ ID NO: 61, a VL-FR3 amino acid sequence at least about 80%, about 90%, or about 95% identical to the amino acid sequence set forth in SEQ ID NO: 65, and a VL-FR4 amino acid sequence at least about 80%, about 90%, or about 95% identical to the amino acid sequence set forth in SEQ ID NO: 68. In certain embodiments, the recombinant antibody is for use in treating cancer. In certain embodiments, the cancer comprises glioblastoma, pancreatic cancer, ovarian cancer, or lung cancer. In certain embodiments, the recombinant antibody is a constituent of a pharmaceutical composition comprising the recombinant antibody and a pharmaceutically acceptable carrier. In certain embodiments, the pharmaceutical composition is formulated for intravenous administration. In certain embodiments, the pharmaceutical composition is formulated for intracerebral administration. In certain embodiments, the pharmaceutical composition is for use in treating cancer. In certain embodiments, the cancer comprises glioblastoma, pancreatic cancer, ovarian cancer, colon cancer, prostate cancer, or lung cancer.

In another aspect, described herein, is a recombinant antibody that specifically binds Leukemia Inhibitory Factor (LIF) comprising: a) an immunoglobulin heavy chain variable region (VH) sequence with an amino acid sequence at least about 80%, about 90%, or about 95% identical to the amino acid sequence set forth in any one of SEQ ID NOs: 71, 72, or 74; and b) an immunoglobulin light chain variable region (VL) sequence with an amino acid sequence at least about 80%, about 90%, or about 95% identical to the amino acid sequence set forth in any one of SEQ ID NOs: 75-78. In certain embodiments, the VH sequence is at least about 80%, about 90%, or about 95% identical to the amino acid sequence set forth in SEQ ID NO: 72; and the VL sequence is at least about 80%, about 90%, or about 95% identical to the amino acid sequence set forth in SEQ ID NO: 76.

In another aspect, described herein, is a method of treating an individual with cancer comprising administering to the individual a recombinant antibody that specifically binds Leukemia Inhibitory Factor (LIF) comprising: a) a heavy chain complementarity determining region 1 (VH-CDR1) comprising an amino acid sequence set forth in any one of SEQ ID NOs: 1-7 or 33; b) a heavy chain complementarity determining region 2 (VH-CDR2) comprising an amino acid sequence set forth in any one of SEQ ID NOs: 9-13 or 35; c) a heavy chain complementarity determining region 3 (VH-CDR3) comprising an amino acid sequence set forth in any one of SEQ ID NOs: 15-19 or 37; d) a light chain complementarity determining region 1 (VL-CDR1) comprising an amino acid sequence set forth in any one of SEQ ID NOs: 21-23 or 39; e) a light chain complementarity determining region 2 (VL-CDR2) comprising an amino acid sequence set forth in any one of SEQ ID NOs: 25-27 or 41; and f) a light chain complementarity determining region 3 (VL-CDR3) comprising an amino acid sequence set forth in any one of SEQ ID NOs: 29, 30, or 43, wherein the recombinant antibody specifically binds to LIF. In certain embodiments, the recombinant antibody binds to glycosylated LIF. In certain embodiments, the recombinant antibody comprises at least one framework region derived from a human antibody framework region. In certain embodiments, the recombinant antibody is humanized. In certain embodiments, the recombinant antibody is deimmunized. In certain embodiments, the recombinant antibody comprises two immunoglobulin heavy chains and two immunoglobulin light chains. In certain embodiments, the recombinant antibody is a Fab, F(ab)$_2$, single-domain antibody, a single chain variable fragment (scFv), or a nanobody. In certain embodiments, the recombinant antibody specifically binds LIF with a dissociation constant ($K_D$) of less than about 200 picomolar. In certain embodiments, the recombinant antibody specifically binds LIF with a dissociation constant ($K_D$) of less than about 100 picomolar. In certain embodiments, the VH-CDR1 comprises an amino acid sequence set forth in SEQ ID NO: 4 (GFTFSNAWMH), wherein the VH-CDR2 comprises an amino acid sequence set forth in SEQ ID NO: 11 (QIKDKSDNYATYYAESVKG), wherein the VH-CDR3 comprises an amino acid sequence set forth in SEQ ID NO: 17 (TCWEWYLDF), wherein the VL-CDR1 comprises an amino acid sequence set forth in SEQ ID NO: 21 (RSSQSLLDSDGHTYLN), wherein the VL-CDR2 comprises an amino acid sequence set forth in SEQ ID NO: 25 (SVSNLES), and wherein the VL-CDR3 comprises an amino acid sequence set forth in SEQ ID NO: 29 (MQATHAPPYT). In certain embodiments, the VH-CDR1 comprises an amino acid sequence set forth in SEQ ID NO: 7 (SKFMY), wherein the VH-CDR2 comprises an amino acid sequence set forth in SEQ ID NO: 13 (WIYPGDGDTEYNQKFSE), wherein the VH-CDR3 comprises an amino acid sequence set forth in SEQ ID NO: 19 (RDYHSSHFAY), wherein the VL-CDR1 comprises an amino acid sequence set forth in SEQ ID NO: 23 (RSSQSLLHNNGNTYLS), wherein the VL-CDR2 comprises an amino acid sequence set forth in SEQ ID NO: 27 (QVSNRFS), and wherein the VL-CDR3 comprises an amino acid sequence set forth in SEQ ID NO: 30 (GQGTQYPYT). In certain embodiments, the VH-CDR1 comprises an amino acid sequence set forth in SEQ ID NO: 33 (TAGMQ), wherein the VH-CDR2 comprises an amino acid sequence set forth in SEQ ID NO: 35 (WINTQSGEPQYVDDFRG), wherein the VH-CDR3 comprises an amino acid sequence set forth in SEQ ID NO: 37 (WALYSEYDVMDY), wherein the VL-CDR1 comprises an amino acid sequence set forth in SEQ ID NO: 39 (KASENVDSYVS), wherein the VL-CDR2 comprises an amino acid sequence set forth in SEQ ID NO: 41 (GASNRYT), and wherein the VL-CDR3 comprises an amino acid sequence set forth in SEQ ID NO: 43 (GQSYRYPPT). In certain embodiments, the VH-CDR1 comprises an amino acid sequence set forth in SEQ ID NO: 1 (GFTFSHAWMH), wherein the VH-CDR2 comprises an amino acid sequence set forth in SEQ ID NO: 9 (QIKAKSDDYATYYAESVKG), wherein the VH-CDR3 comprises an amino acid sequence set forth in SEQ ID NO: 15 (TCWEWDLDF), wherein the VL-CDR1 comprises an amino acid sequence set forth in SEQ ID NO: 21 (RSSQSLLDSDGHTYLN), wherein the VL-CDR2 comprises an amino acid sequence set forth in SEQ ID NO: 25 (SVSNLES), and wherein the VL-CDR3 comprises an amino acid sequence set forth in SEQ ID NO: 29 (MQATHAPPYT). In certain embodiments, the recombinant antibody comprises one or more of a heavy chain framework 1 (VH-FR1) region amino acid sequence at least about 80%, about 90%, or about 95% identical to the amino acid sequence set forth in any one of SEQ ID NOs: 44-47, a heavy chain framework 2 (VH-FR2) region amino acid sequence at least about 80%, about 90%, or about 95% identical to the amino acid sequence set forth in any one of SEQ ID NOs: 48-49, a heavy chain framework 3 (VH-FR3) region amino acid sequence at least about 80%, about 90%, or about 95% identical to the amino acid sequence set forth in any one of SEQ ID NOs: 50-52, and a heavy chain framework 4 (VH-FR4) region amino acid sequence at least about 80%, about 90%, or about 95% identical to the amino acid sequence set forth in any one of SEQ ID NOs: 53-55. In certain embodiments, the recombinant antibody comprises one or more of a light chain framework 1 (VL-FR1) region amino acid sequence at least about 80%, about 90%, or about 95% identical to the amino acid sequence set forth in any one of SEQ ID NOs: 56-59, a light chain framework 2 (VL-FR2) region amino acid sequence at least about 80%, about 90%, or about 95% identical to the amino acid sequence set forth in any one of SEQ ID NOs: 60-63, a light chain framework 3 (VL-FR3) region amino acid sequence at least about 80%, about 90%, or about 95% identical to the amino acid sequence set forth in any one of SEQ ID NOs: 64-67, and a light chain framework 4 (VL-FR4) region amino acid sequence at least about 80%, about 90%, or about 95% identical to the amino acid sequence set forth in any one of SEQ ID NOs: 68-70. In certain embodiments, the recombinant antibody comprises a VH-FR1 amino acid sequence at least about 80%, about 90%, or about 95% identical to the amino acid sequence set forth in SEQ ID NO: 45, a VH-FR2 amino acid sequence at least about 80%, about 90%, or about 95% identical to the amino acid sequence set forth in SEQ ID NO: 49, a VH-FR3 amino acid sequence at least about 80%, about 90%, or about 95% identical to the amino acid sequence set forth in SEQ ID NO: 50, and a VH-FR4 amino acid sequence at least about 80%, about 90%, or about 95% identical to the amino acid sequence set forth in SEQ ID NO: 54. In certain embodiments, the recombinant antibody comprises a VL-FR1 amino acid sequence at least about 80%, about 90%, or about 95% identical to the amino acid sequence set forth in SEQ ID NO: 57, a VL-FR2 amino acid sequence at least about 80%, about 90%, or about 95% identical to the amino acid sequence set forth in SEQ ID NO: 61, a VL-FR3 amino acid sequence at least about 80%, about 90%, or about 95% identical to the amino acid sequence set forth in SEQ ID NO: 65, and a VL-FR4 amino acid sequence at least about 80%, about 90%, or about 95% identical to the amino acid sequence set forth in SEQ ID NO: 68. In certain embodiments, the recombinant antibody comprises a VH-FR1 amino acid sequence at least about 80%, about 90%, or about 95% identical to the amino acid sequence set forth in SEQ ID NO: 45, a VH-FR2 amino acid sequence at least about 80%, about 90%, or about 95% identical to the amino acid sequence set forth in SEQ ID NO: 49, a VH-FR3 amino acid sequence at least about 80%, about 90%, or about 95% identical to the amino acid sequence set forth in SEQ ID NO: 50, a VH-FR4 amino acid sequence at least about 80%, about 90%, or about 95% identical to the amino acid sequence set forth in SEQ ID NO: 54, a VL-FR1 amino acid sequence at least about 80%, about 90%, or about 95% identical to the amino acid sequence set forth in SEQ ID NO: 57, a VL-FR2 amino acid sequence at least about 80%, about 90%, or about 95% identical to the amino acid sequence set forth in SEQ ID NO: 61, a VL-FR3 amino acid sequence at least about 80%, about 90%, or about 95% identical to the amino acid sequence set forth in SEQ ID NO: 65, and a VL-FR4 amino acid sequence at least about 80%, about 90%, or about 95% identical to the amino acid sequence set forth in SEQ ID NO: 68. In certain embodiments, the cancer comprises glioblastoma, pancreatic cancer, ovarian cancer, colon cancer, prostate cancer, or lung cancer. In certain embodiments, the recombinant antibody is administered intravenously. In certain embodiments, the recombinant antibody is administered intracerebrally.

In another aspect, described herein, is a method of treating an individual with cancer comprising administering to the individual a recombinant antibody that specifically binds Leukemia Inhibitory Factor (LIF) comprising: a) an immunoglobulin heavy chain variable region (VH) sequence with an amino acid sequence at least about 80%, about 90%, or about 95% identical to the amino acid sequence set forth in any one of SEQ ID NOs: 71, 72, or 74; and b) an immunoglobulin light chain variable region (VL) sequence with an amino acid sequence at least about 80%, about 90%, or about 95% identical to the amino acid sequence set forth in any one of SEQ ID NOs: 75-78. In certain embodiments, the VH sequence is at least about 80%, about 90%, or about 95% identical to the amino acid sequence set forth in SEQ ID NO: 72; and the VL sequence is at least about 80%, about 90%, or about 95% identical to the amino acid sequence set forth in SEQ ID NO: 76.

In another aspect, described herein, is a method of preparing a cancer treatment for treating a subject with cancer comprising admixing a pharmaceutically acceptable carrier and a recombinant antibody that specifically binds Leukemia Inhibitory Factor (LIF) comprising a heavy chain complementarity determining region 1 (VH-CDR1) comprising: a) a heavy chain complementarity determining region 1 (VH-CDR1) comprising an amino acid sequence set forth in any one of SEQ ID NOs: 1-7 or 33; b) a heavy chain complementarity determining region 2 (VH-CDR2) comprising an amino acid sequence set forth in any one of SEQ ID NOs: 9-13 or 35; c) a heavy chain complementarity determining region 3 (VH-CDR3) comprising an amino acid sequence set forth in any one of SEQ ID NOs: 15-19 or 37; d) a light chain complementarity determining region 1 (VL-CDR1) comprising an amino acid sequence set forth in any one of SEQ ID NOs: 21-23 or 39; e) a light chain complementarity determining region 2 (VL-CDR2) comprising an amino acid sequence set forth in any one of SEQ ID NOs: 25-27 or 41; and f) a light chain complementarity determining region 3 (VL-CDR3) comprising an amino acid sequence set forth in any one of SEQ ID NOs: 29, 30, or 43, wherein the recombinant antibody specifically binds to LIF. In certain embodiments, the recombinant antibody binds to glycosylated LIF. In certain embodiments, the recombinant antibody comprises at least one framework region derived from a human antibody framework region. In certain embodiments, the recombinant antibody is humanized. In certain embodiments, the recombinant antibody is deimmunized. In certain embodiments, the recombinant antibody comprises two immunoglobulin heavy chains and two immunoglobulin light chains. In certain embodiments, the recombinant antibody is a Fab, F(ab)$_2$, single-domain antibody, a single chain variable fragment (scFv), or a nanobody. In certain embodiments, the recombinant antibody specifically binds LIF with a dissociation constant ($K_D$) of less than about 200 picomolar. In certain embodiments, the recombinant antibody specifically binds LIF with a dissociation constant ($K_D$) of less than about 100 picomolar. In certain embodiments, the VH-CDR1 comprises an amino acid sequence set forth in SEQ ID NO: 4 (GFTFSNAWMH), wherein the VH-CDR2 comprises an amino acid sequence set forth in SEQ ID NO: 11 (QIKDKSDNYATYYAESVKG), wherein the VH-CDR3 comprises an amino acid sequence set forth in SEQ ID NO: 17 (TCWEWYLDF), wherein the VL-CDR1 comprises an amino acid sequence set forth in SEQ ID NO: 21 (RSSQSLLDSDGHTYLN), wherein the VL-CDR2 comprises an amino acid sequence set forth in SEQ ID NO: 25 (SVSNLES), and wherein the VL-CDR3 comprises an amino acid sequence set forth in SEQ ID NO: 29 (MQATHAPPYT). In certain embodiments, the VH-CDR1 comprises an amino acid sequence set forth in SEQ ID NO: 7 (SKFMY), wherein the VH-CDR2 comprises an amino acid sequence set forth in SEQ ID NO: 13 (WIYPGDGDTEYNQKFSE), wherein the VH-CDR3 comprises an amino acid sequence set forth in SEQ ID NO: 19 (RDYHSSHFAY), wherein the VL-CDR1 comprises an amino acid sequence set forth in SEQ ID NO: 23 (RSSQSLLHNNGNTYLS), wherein the VL-CDR2 comprises an amino acid sequence set forth in SEQ ID NO: 27 (QVSNRFS), and wherein the VL-CDR3 comprises an amino acid sequence set forth in SEQ ID NO: 30 (GQGTQYPYT). In certain embodiments, the VH-CDR1 comprises an amino acid sequence set forth in SEQ ID NO: 33 (TAGMQ), wherein the VH-CDR2 comprises an amino acid sequence set forth in SEQ ID NO: 35 (WINTQSGEPQYVDDFRG), wherein the VH-CDR3 comprises an amino acid sequence set forth in SEQ ID NO: 37 (WALYSEYDVMDY), wherein the VL-CDR1 comprises an amino acid sequence set forth in SEQ ID NO: 39 (KASENVDSYVS), wherein the VL-CDR2 comprises an amino acid sequence set forth in SEQ ID NO: 41 (GASNRYT), and wherein the VL-CDR3 comprises an amino acid sequence set forth in SEQ ID NO: 43 (GQSYRYPPT). In certain embodiments, the VH-CDR1 comprises an amino acid sequence set forth in SEQ ID NO: 1 (GFTFSHAWMH), wherein the VH-CDR2 comprises an amino acid sequence set forth in SEQ ID NO: 9 (QIKAKSDDYATYYAESVKG), wherein the VH-CDR3 comprises an amino acid sequence set forth in SEQ ID NO: 15 (TCWEWDLDF), wherein the VL-CDR1 comprises an amino acid sequence set forth in SEQ ID NO: 21 (RSSQSLLDSDGHTYLN), wherein the VL-CDR2 comprises an amino acid sequence set forth in SEQ ID NO: 25 (SVSNLES), and wherein the VL-CDR3 comprises an amino acid sequence set forth in SEQ ID NO: 29 (MQATHAPPYT). In certain embodiments, the recombinant antibody comprises one or more of a heavy chain framework 1 (VH-FR1) region amino acid sequence at least about 80%, about 90%, or about 95% identical to the amino acid sequence set forth in any one of SEQ ID NOs: 44-47, a heavy chain framework 2 (VH-FR2) region amino acid sequence at least about 80%, about 90%, or about 95% identical to the amino acid sequence set forth in any one of SEQ ID NOs: 48-49, a heavy chain framework 3 (VH-FR3) region amino acid sequence at least about 80%, about 90%, or about 95% identical to the amino acid sequence set forth in any one of SEQ ID NOs: 50-52, and a heavy chain framework 4 (VH-FR4) region amino acid sequence at least about 80%, about 90%, or about 95% identical to the amino acid sequence set forth in any one of SEQ ID NOs: 53-55. In certain embodiments, the recombinant antibody comprises one or more of a light chain framework 1 (VL-FR1) region amino acid sequence at least about 80%, about 90%, or about 95% identical to the amino acid sequence set forth in any one of SEQ ID NOs: 56-59, a light chain framework 2 (VL-FR2) region amino acid sequence at least about 80%, about 90%, or about 95% identical to the amino acid sequence set forth in any one of SEQ ID NOs: 60-63, a light chain framework 3 (VL-FR3) region amino acid sequence at least about 80%, about 90%, or about 95% identical to the amino acid sequence set forth in any one of SEQ ID NOs: 64-67, and a light chain framework 4 (VL-FR4) region amino acid sequence at least about 80%, about 90%, or about 95% identical to the amino acid sequence set forth in any one of SEQ ID NOs: 68-70. In certain embodiments, the recombinant antibody comprises a VH-FR1 amino acid sequence at least about 80%, about 90%, or about 95% identical to the amino acid sequence set forth in SEQ ID NO: 45, a VH-FR2 amino acid sequence at least about 80%, about 90%, or about 95% identical to the amino acid sequence set forth in SEQ ID NO: 49, a VH-FR3 amino acid sequence at least about 80%, about 90%, or about 95% identical to the amino acid sequence set forth in SEQ ID NO: 50, and a VH-FR4 amino acid sequence at least about 80%, about 90%, or about 95% identical to the amino acid sequence set forth in SEQ ID NO: 54. In certain embodiments, the recombinant antibody comprises a VL-FR1 amino acid sequence at least about 80%, about 90%, or about 95% identical to the amino acid sequence set forth in SEQ ID NO: 57, a VL-FR2 amino acid sequence at least about 80%, about 90%, or about 95% identical to the amino acid sequence set forth in SEQ ID NO: 61, a VL-FR3 amino acid sequence at least about 80%, about 90%, or about 95% identical to the amino acid sequence set forth in SEQ ID NO: 65, and a VL-FR4 amino acid sequence at least about 80%, about 90%, or about 95% identical to the amino acid sequence set forth in SEQ ID NO: 68. In certain embodiments, the recombinant antibody comprises a VH-FR1 amino acid sequence at least about 80%, about 90%, or about 95% identical to the amino acid sequence set forth in SEQ ID NO: 45, a VH-FR2 amino acid sequence at least about 80%, about 90%, or about 95% identical to the amino acid sequence set forth in SEQ ID NO: 49, a VH-FR3 amino acid sequence at least about 80%, about 90%, or about 95% identical to the amino acid sequence set forth in SEQ ID NO: 50, a VH-FR4 amino acid sequence at least about 80%, about 90%, or about 95% identical to the amino acid sequence set forth in SEQ ID NO: 54, a VL-FR1 amino acid sequence at least about 80%, about 90%, or about 95% identical to the amino acid sequence set forth in SEQ ID NO: 57, a VL-FR2 amino acid sequence at least about 80%, about 90%, or about 95% identical to the amino acid sequence set forth in SEQ ID NO: 61, a VL-FR3 amino acid sequence at least about 80%, about 90%, or about 95% identical to the amino acid sequence set forth in SEQ ID NO: 65, and a VL-FR4 amino acid sequence at least about 80%, about 90%, or about 95% identical to the amino acid sequence set forth in SEQ ID NO: 68. In certain embodiments, the cancer comprises glioblastoma, pancreatic cancer, ovarian cancer, colon cancer, prostate cancer, or lung cancer.

In another aspect, described herein, is a method of preparing a cancer treatment for treating a subject with cancer comprising admixing a pharmaceutically acceptable carrier and a recombinant antibody that specifically binds Leukemia Inhibitory Factor (LIF) comprising: a) an immunoglobulin heavy chain variable region (VH) sequence with an amino acid sequence at least about 80%, about 90%, or about 95% identical to the amino acid sequence set forth in any one of SEQ ID NOs: 71, 72, or 74; b) and an immunoglobulin light chain variable region (VL) sequence with an amino acid sequence at least about 80%, about 90%, or about 95% identical to the amino acid sequence set forth in any one of SEQ ID NOs: 75-78. In certain embodiments, the VH sequence is at least about 80%, about 90%, or about 95% identical to the amino acid sequence set forth in SEQ ID NO: 72; and the VL sequence is at least about 80%, about 90%, or about 95% identical to the amino acid sequence set forth in SEQ ID NO: 76.

In another aspect, described herein, is a recombinant antibody that specifically binds Leukemia Inhibitory Factor (LIF) comprising at least one complementarity determining region (CDR) of rat origin and at least one immunoglobulin framework region (FR) of human origin, wherein the at least one CDR of rat origin specifically binds to LIF. In certain embodiments, the recombinant antibody binds to glycosylated LIF. In certain embodiments, the recombinant antibody comprises at least one framework region derived from a human antibody framework region. In certain embodiments, the recombinant antibody is humanized. In certain embodiments, the recombinant antibody is deimmunized. In certain embodiments, the recombinant antibody comprises two immunoglobulin heavy chains and two immunoglobulin light chains. In certain embodiments, the recombinant antibody is a Fab, F(ab)$_2$, single-domain antibody, a single chain variable fragment (scFv), or a nanobody. In certain embodiments, the recombinant antibody specifically binds LIF with a dissociation constant ($K_D$) of less than about 200 picomolar. In certain embodiments, the recombinant antibody specifically binds LIF with a dissociation constant ($K_D$) of less than about 100 picomolar. In certain embodiments, the at least one CDR of rat origin comprises an amino acid sequence set forth in any one of SEQ ID NOs: 1-3, 9, 10, 15, 16, 21, 22, 25, 26, or 29. In certain embodiments, the at least one CDR of rat origin comprises an amino acid sequence set forth in any one of SEQ ID NOs: 1, 9, 15, 21, 25, and 29. In certain embodiments, the at least one immunoglobulin framework region of human origin comprises an amino acid sequence set forth in any one of SEQ ID NOs: 44-70. In certain embodiments, the recombinant antibody comprises a heavy chain CDR1 amino acid sequence set forth in SEQ ID NO: 1, a heavy chain CDR2 amino acid sequence set forth in SEQ ID NO: 9, and a heavy chain CDR3 amino acid sequence set forth in SEQ ID NO: 15. In certain embodiments, the recombinant antibody comprises a light chain CDR1 amino acid sequence set forth in SEQ ID NO: 21, a light chain CDR2 amino acid sequence set forth in SEQ ID NO: 25, and a light chain CDR3 amino acid sequence set forth in SEQ ID NO: 29. In certain embodiments, the recombinant antibody comprises a heavy chain CDR1 amino acid sequence set forth in SEQ ID NO: 1, a heavy chain CDR2 amino acid sequence set forth in SEQ ID NO: 9, a heavy chain CDR3 amino acid sequence set forth in SEQ ID NO: 15, a light chain CDR1 amino acid sequence set forth in SEQ ID NO: 21, a light chain CDR2 amino acid sequence set forth in SEQ ID NO: 25, and a light chain CDR3 amino acid sequence set forth in SEQ ID NO: 29. In certain embodiments, the recombinant antibody comprises a heavy chain FR1 amino acid sequence at least about 80%, about 90%, or about 95% identical to the amino acid sequence set forth in SEQ ID NO: 45, a heavy chain FR2 amino acid sequence at least about 80%, about 90%, or about 95% identical to the amino acid sequence set forth in SEQ ID NO: 49, a heavy chain FR3 amino acid sequence at least about 80%, about 90%, or about 95% identical to the amino acid sequence set forth in SEQ ID NO: 50, and a heavy chain FR4 amino acid sequence at least about 80%, about 90%, or about 95% identical to the amino acid sequence set forth in SEQ ID NO: 54. In certain embodiments, the recombinant antibody comprises a light chain FR1 amino acid sequence at least about 80%, about 90%, or about 95% identical to the amino acid sequence set forth in SEQ ID NO: 57, a light chain FR2 amino acid sequence at least about 80%, about 90%, or about 95% identical to the amino acid sequence set forth in SEQ ID NO: 61, a light chain FR3 amino acid sequence at least about 80%, about 90%, or about 95% identical to the amino acid sequence set forth in SEQ ID NO: 65, and a light chain FR4 amino acid sequence at least about 80%, about 90%, or about 95% identical to the amino acid sequence set forth in SEQ ID NO: 68. In certain embodiments, the recombinant antibody comprises a heavy chain FR1 amino acid sequence at least about 80%, about 90%, or about 95% identical to the amino acid sequence set forth in SEQ ID NO: 45, a heavy chain FR2 amino acid sequence at least about 80%, about 90%, or about 95% identical to the amino acid sequence set forth in SEQ ID NO: 49, a heavy chain FR3 amino acid sequence at least about 80%, about 90%, or about 95% identical to the amino acid sequence set forth in SEQ ID NO: 50, a heavy chain FR4 amino acid sequence at least about 80%, about 90%, or about 95% identical to the amino acid sequence set forth in SEQ ID NO: 54, a light chain FR1 amino acid sequence at least about 80%, about 90%, or about 95% identical to the amino acid sequence set forth in SEQ ID NO: 57, a light chain FR2 amino acid sequence at least about 80%, about 90%, or about 95% identical to the amino acid sequence set forth in SEQ ID NO: 61, a light chain FR3 amino acid sequence at least about 80%, about 90%, or about 95% identical to the amino acid sequence set forth in SEQ ID NO: 65, and a light chain FR4 amino acid sequence at least about 80%, about 90%, or about 95% identical to the amino acid sequence set forth in SEQ ID NO: 68. In certain embodiments, the recombinant antibody further comprises a pharmaceutically acceptable carrier. In certain embodiments, the recombinant antibody is formulated for intravenous administration. In certain embodiments, the recombinant antibody is formulated for intracerebral administration. In certain embodiments, the recombinant antibody of is for use in treating cancer. In certain embodiments, the cancer comprises glioblastoma, pancreatic cancer, ovarian cancer, colon cancer, prostate cancer, or lung cancer.

In another aspect, described herein, is a recombinant antibody that specifically binds Leukemia Inhibitory Factor (LIF) comprising an immunoglobulin heavy chain sequence with an amino acid sequence at least about 80%, about 90%, or about 95% identical to the amino acid sequence set forth in any one of SEQ ID NOs: 71, 72, or 74; and an immunoglobulin light chain sequence with an amino acid sequence at least about 80%, about 90%, or about 95% identical to the amino acid sequence set forth in any one of SEQ ID NOs: 75-78. In certain embodiments, the immunoglobulin heavy chain sequence is at least about 80%, about 90%, or about 95% identical to the amino acid sequence set forth in of SEQ ID NO: 72; and the immunoglobulin light chain sequence is at least about 80%, about 90%, or about 95% identical to the amino acid sequence set forth in of SEQ ID NO: 76.

In another aspect, described herein, is a method of treating a subject with cancer comprising administering to an individual a recombinant antibody that specifically binds Leukemia Inhibitory Factor (LIF), wherein the recombinant antibody that specifically binds (LIF) comprises at least one complementarity determining region (CDR) of rat origin and at least one immunoglobulin framework region (FR) of human origin, wherein the at least one CDR of rat origin specifically binds to LIF. In certain embodiments, the recombinant antibody binds to glycosylated LIF. In certain embodiments, the recombinant antibody comprises at least one framework region derived from a human antibody framework region. In certain embodiments, the recombinant antibody is humanized. In certain embodiments, the recombinant antibody is deimmunized. In certain embodiments, the recombinant antibody comprises two immunoglobulin heavy chains and two immunoglobulin light chains. In certain embodiments, the recombinant antibody is a Fab, F(ab)$_2$, single-domain antibody, a single chain variable fragment (scFv), or a nanobody. In certain embodiments, the recombinant antibody specifically binds LIF with a dissociation constant (K$_D$) of less than about 200 picomolar. In certain embodiments, the recombinant antibody specifically binds LIF with a dissociation constant (K$_D$) of less than about 100 picomolar. In certain embodiments, at least one CDR of rat origin comprises an amino acid sequence set forth in any one of SEQ ID NOs: 1-3, 9, 10, 15, 16, 21, 22, 25, 26, or 29. In certain embodiments, the at least one CDR of rat origin comprises an amino acid sequence set forth in any one of SEQ ID NOs: 1, 7, 11, 15, 17, and 19. In certain embodiments, the at least one CDR of rat origin comprises an amino acid sequence set forth in any one of SEQ ID NOs: 1, 9, 15, 21, 25, and 29. In certain embodiments, the at least one immunoglobulin framework region of human origin comprises an amino acid sequence set forth in any one of SEQ ID NOs: 44-70. In certain embodiments, the recombinant antibody that specifically binds LIF comprises a heavy chain CDR1 amino acid sequence set forth in SEQ ID NO: 1, a heavy chain CDR2 amino acid sequence set forth in SEQ ID NO: 9, and a heavy chain CDR3 amino acid sequence set forth in SEQ ID NO: 15. In certain embodiments, the recombinant antibody that specifically binds LIF comprises a light chain CDR1 amino acid sequence set forth in SEQ ID NO: 21, a light chain CDR2 amino acid sequence set forth in SEQ ID NO: 25, and a light chain CDR3 amino acid sequence set forth in SEQ ID NO: 29. In certain embodiments, the recombinant antibody that specifically binds LIF comprises a heavy chain CDR1 amino acid sequence set forth in SEQ ID NO: 1, a heavy chain CDR2 amino acid sequence set forth in SEQ ID NO: 9, a heavy chain CDR3 amino acid sequence set forth in SEQ ID NO: 15, a light chain CDR1 amino acid sequence set forth in SEQ ID NO: 21, a light chain CDR2 amino acid sequence set forth in SEQ ID NO: 25, and a light chain CDR3 amino acid sequence set forth in SEQ ID NO: 29. In certain embodiments, the recombinant antibody comprises a heavy chain FR1 amino acid sequence at least about 80%, about 90%, or about 95% identical to the amino acid sequence set forth in SEQ ID NO: 45, a heavy chain FR2 amino acid sequence at least about 80%, about 90%, or about 95% identical to the amino acid sequence set forth in SEQ ID NO: 49, a heavy chain FR3 amino acid sequence at least about 80%, about 90%, or about 95% identical to the amino acid sequence set forth in SEQ ID NO: 50, and a heavy chain FR4 amino acid sequence at least about 80%, about 90%, or about 95% identical to the amino acid sequence set forth in SEQ ID NO: 54. In certain embodiments, the recombinant antibody that specifically binds LIF comprises a light chain FR1 amino acid sequence at least about 80%, about 90%, or about 95% identical to the amino acid sequence set forth in SEQ ID NO: 57, a light chain FR2 amino acid sequence at least about 80%, about 90%, or about 95% identical to the amino acid sequence set forth in SEQ ID NO: 61, a light chain FR3 amino acid sequence at least about 80%, about 90%, or about 95% identical to the amino acid sequence set forth in SEQ ID NO: 65, and a light chain FR4 amino acid sequence at least about 80%, about 90%, or about 95% identical to the amino acid sequence set forth in SEQ ID NO: 68. In certain embodiments, the recombinant antibody that specifically binds LIF comprises a heavy chain FR1 amino acid sequence at least about 80%, about 90%, or about 95% identical to the amino acid sequence set forth in SEQ ID NO: 45, a heavy chain FR2 amino acid sequence at least about 80%, about 90%, or about 95% identical to the amino acid sequence set forth in SEQ ID NO: 49, a heavy chain FR3 amino acid sequence at least about 80%, about 90%, or about 95% identical to the amino acid sequence set forth in SEQ ID NO: 50, a heavy chain FR4 amino acid sequence at least about 80%, about 90%, or about 95% identical to the amino acid sequence set forth in SEQ ID NO: 54, a light chain FR1 amino acid sequence at least about 80%, about 90%, or about 95% identical to the amino acid sequence set forth in SEQ ID NO: 57, a light chain FR2 amino acid sequence at least about 80%, about 90%, or about 95% identical to the amino acid sequence set forth in SEQ ID NO: 61, a light chain FR3 amino acid sequence at least about 80%, about 90%, or about 95% identical to the amino acid sequence set forth in SEQ ID NO: 65, and a light chain FR4 amino acid sequence at least about 80%, about 90%, or about 95% identical to the amino acid sequence set forth in SEQ ID NO: 68. In certain embodiments, the recombinant antibody is administered intravenously. In certain embodiments, the recombinant antibody is administered intracerebrally. In certain embodiments, the cancer comprises glioblastoma, pancreatic cancer, ovarian cancer, colon cancer, prostate cancer, or lung cancer.

In another aspect, described herein, is a method of treating a subject with cancer comprising administering to an individual a recombinant antibody that specifically binds Leukemia Inhibitory Factor (LIF), wherein the recombinant antibody that specifically binds (LIF) comprises an immunoglobulin heavy chain sequence with an amino acid sequence at least about 80%, about 90%, or about 95% identical to the amino acid sequence set forth in any one of SEQ ID NOs: 71, 72, or 74; and an immunoglobulin light chain sequence with an amino acid sequence at least about 80%, about 90%, or about 95% identical to the amino acid sequence set forth in any one of SEQ ID NOs: 75-78. In certain embodiments, the immunoglobulin heavy chain sequence is at least about 80%, about 90%, or about 95% identical to the amino acid sequence set forth in of SEQ ID NO: 72; and the immunoglobulin light chain sequence is at least about 80%, about 90%, or about 95% identical to the amino acid sequence set forth in of SEQ ID NO: 76.

In another aspect, described herein, is a method of preparing a cancer treatment for treating a subject with cancer comprising admixing a pharmaceutically acceptable carrier and a recombinant antibody that specifically binds Leukemia Inhibitory Factor (LIF), wherein the recombinant antibody that specifically binds (LIF) comprises at least one complementarity determining region (CDR) of rat origin and at least one immunoglobulin framework region (FR) of human origin, wherein the at least one CDR of rat origin specifically binds to LIF. In certain embodiments, the recombinant antibody binds to glycosylated LIF. In certain embodiments, the recombinant antibody comprises at least one framework region derived from a human antibody framework region. In certain embodiments, the recombinant antibody is humanized. In certain embodiments, the recombinant antibody is deimmunized. In certain embodiments, the recombinant antibody comprises two immunoglobulin heavy chains and two immunoglobulin light chains. In certain embodiments, the recombinant antibody is a Fab, F(ab)$_2$, single-domain antibody, a single chain variable fragment (scFv), or a nanobody. In certain embodiments, the recombinant antibody specifically binds LIF with a dissociation constant ($K_D$) of less than about 200 picomolar. In certain embodiments, the recombinant antibody specifically binds LIF with a dissociation constant ($K_D$) of less than about 100 picomolar. In certain embodiments, the at least one CDR of rat origin comprises an amino acid sequence set forth in any one of SEQ ID NOs: 1-3, 9, 10, 15, 16, 21, 22, 25, 26, or 29. In certain embodiments, the at least one CDR of rat origin comprises an amino acid sequence set forth in any one of SEQ ID NOs: 1, 9, 15, 21, 25, and 29. In certain embodiments, the at least one immunoglobulin framework region of human origin comprises an amino acid sequence set forth in any one of SEQ ID NOs: 44-70. In certain embodiments, the recombinant antibody that specifically binds LIF comprises a heavy chain CDR1 amino acid sequence set forth in SEQ ID NO: 1, a heavy chain CDR2 amino acid sequence set forth in SEQ ID NO: 9, and a heavy chain CDR3 amino acid sequence set forth in SEQ ID NO: 15. In certain embodiments, the recombinant antibody that specifically binds LIF comprises a light chain CDR1 amino acid sequence set forth in SEQ ID NO: 21, a light chain CDR2 amino acid sequence set forth in SEQ ID NO: 25, and a light chain CDR3 amino acid sequence set forth in SEQ ID NO: 29. In certain embodiments, the recombinant antibody that specifically binds LIF comprises a heavy chain CDR1 amino acid sequence set forth in SEQ ID NO: 1, a heavy chain CDR2 amino acid sequence set forth in SEQ ID NO: 9, a heavy chain CDR3 amino acid sequence set forth in SEQ ID NO: 15, a light chain CDR1 amino acid sequence set forth in SEQ ID NO: 21, a light chain CDR2 amino acid sequence set forth in SEQ ID NO: 25, and a light chain CDR3 amino acid sequence set forth in SEQ ID NO: 29. In certain embodiments, the recombinant antibody that specifically binds LIF comprises a heavy chain FR1 amino acid sequence at least about 80%, about 90%, or about 95% identical to the amino acid sequence set forth in SEQ ID NO: 45, a heavy chain FR2 amino acid sequence at least about 80%, about 90%, or about 95% identical to the amino acid sequence set forth in SEQ ID NO: 49, a heavy chain FR3 amino acid sequence at least about 80%, about 90%, or about 95% identical to the amino acid sequence set forth in SEQ ID NO: 50, and a heavy chain FR4 amino acid sequence at least about 80%, about 90%, or about 95% identical to the amino acid sequence set forth in SEQ ID NO: 54. In certain embodiments, the recombinant antibody comprises a light chain FR1 amino acid sequence at least about 80%, about 90%, or about 95% identical to the amino acid sequence set forth in SEQ ID NO: 57, a light chain FR2 amino acid sequence at least about 80%, about 90%, or about 95% identical to the amino acid sequence set forth in SEQ ID NO: 61, a light chain FR3 amino acid sequence at least about 80%, about 90%, or about 95% identical to the amino acid sequence set forth in SEQ ID NO: 65, and a light chain FR4 amino acid sequence at least about 80%, about 90%, or about 95% identical to the amino acid sequence set forth in SEQ ID NO: 68. In certain embodiments, the recombinant antibody that specifically binds LIF comprises a heavy chain FR1 amino acid sequence at least about 80%, about 90%, or about 95% identical to the amino acid sequence set forth in SEQ ID NO: 45, a heavy chain FR2 amino acid sequence at least about 80%, about 90%, or about 95% identical to the amino acid sequence set forth in SEQ ID NO: 49, a heavy chain FR3 amino acid sequence at least about 80%, about 90%, or about 95% identical to the amino acid sequence set forth in SEQ ID NO: 50, a heavy chain FR4 amino acid sequence at least about 80%, about 90%, or about 95% identical to the amino acid sequence set forth in SEQ ID NO: 54, a light chain FR1 amino acid sequence at least about 80%, about 90%, or about 95% identical to the amino acid sequence set forth in SEQ ID NO: 57, a light chain FR2 amino acid sequence at least about 80%, about 90%, or about 95% identical to the amino acid sequence set forth in SEQ ID NO: 61, a light chain FR3 amino acid sequence at least about 80%, about 90%, or about 95% identical to the amino acid sequence set forth in SEQ ID NO: 65, and a light chain FR4 amino acid sequence at least about 80%, about 90%, or about 95% identical to the amino acid sequence set forth in SEQ ID NO: 68. In certain embodiments, the pharmaceutically acceptable carrier is suitable for intravenous administration. In certain embodiments, the pharmaceutically acceptable carrier is suitable for intracerebral administration. In certain embodiments, the cancer comprises glioblastoma, pancreatic cancer, ovarian cancer, colon cancer, prostate cancer, or lung cancer.

In another aspect, described herein, is a method of preparing a cancer treatment for treating a subject with cancer comprising admixing a pharmaceutically acceptable carrier and a recombinant antibody that specifically binds Leukemia Inhibitory Factor (LIF), wherein the recombinant antibody that specifically binds (LIF) comprises an immunoglobulin heavy chain sequence with an amino acid sequence at least about 80%, about 90%, or about 95% identical to the amino acid sequence set forth in any one of SEQ ID NOs: 71, 72, or 74; and an immunoglobulin light chain sequence with an amino acid sequence at least about 80%, about 90%, or about 95% identical to the amino acid sequence set forth in any one of SEQ ID NOs: 75-78. In certain embodiments, the immunoglobulin heavy chain sequence is at least about 80%, about 90%, or about 95% identical to the amino acid sequence set forth in of SEQ ID NO: 72; and the immunoglobulin light chain sequence is at least about 80%, about 90%, or about 95% identical to the amino acid sequence set forth in of SEQ ID NO: 76.

In another aspect described herein is a recombinant antibody that binds LIF, wherein the antibody comprises: a heavy chain CDR1 amino acid sequence set forth in SEQ ID NO: 1, a heavy chain CDR2 amino acid sequence set forth in SEQ ID NO: 9, a heavy chain CDR3 amino acid sequence set forth in SEQ ID NO: 15, a heavy chain FR1 amino acid sequence at least 90% identical to the amino acid sequence set forth in SEQ ID NO: 45, a heavy chain FR2 amino acid sequence at least 90% identical to the amino acid sequence set forth in SEQ ID NO: 49, a heavy chain FR3 amino acid sequence at least 90% identical to the amino acid sequence set forth in SEQ ID NO: 50, a heavy chain FR4 amino acid sequence at least 90% identical to the amino acid sequence set forth in SEQ ID NO: 54, a light chain CDR1 amino acid sequence set forth in SEQ ID NO: 21, a light chain CDR2 amino acid sequence set forth in SEQ ID NO: 25, a light chain CDR3 amino acid sequence set forth in SEQ ID NO: 29, a light chain FR1 amino acid sequence at least 90% identical to the amino acid sequence set forth in SEQ ID NO: 57, a light chain FR2 amino acid sequence at least 90% identical to the amino acid sequence set forth in SEQ ID NO: 61, a light chain FR3 amino acid sequence at least 90% identical to the amino acid sequence set forth in SEQ ID NO: 65, and a light chain FR4 amino acid sequence at least 90% identical to the amino acid sequence set forth in SEQ ID NO: 68.

In another aspect described herein is a recombinant antibody that specifically binds LIF, wherein the antibody comprises, a humanized heavy chain variable region at least 90%, 95%, 97%, 98%, or 99% identical to the amino acid set forth in SEQ ID NO: 72, and a humanized light chain variable region at least 90%, 95%, 97%, 98%, or 99% identical to the amino acid set forth in SEQ ID NO: 76. In certain embodiments, the antibody is formulated with a pharmaceutically acceptable diluent, carrier, or excipient to form a pharmaceutical composition.

In another aspect described herein is a recombinant antibody that specifically binds LIF comprising: a) a heavy chain CDR1 comprising an amino acid sequence set forth in any one of SEQ ID NOs: 1-7 or 33; b) a heavy chain CDR2 comprising an amino acid sequence set forth in any one of SEQ ID NOs: 9-13 or 35; and c) a heavy chain CDR3 comprising an amino acid sequence set forth in any one of SEQ ID NOs: 15-19 or 37, wherein the recombinant antibody specifically binds to LIF. In certain embodiments, the antibody is formulated with a pharmaceutically acceptable diluent, carrier, or excipient to form a pharmaceutical composition.

In another aspect described herein is a recombinant antibody that specifically binds LIF comprising: a) a light chain complementarity determining region 1 (VL-CDR1) comprising an amino acid sequence set forth in any one of SEQ ID NOs: 21-23 or 39; b) a light chain complementarity determining region 2 (VL-CDR2) comprising an amino acid sequence set forth in any one of SEQ ID NOs: 25-27 or 41; and c) a light chain complementarity determining region 3 (VL-CDR3) comprising an amino acid sequence set forth in any one of SEQ ID NOs: 29, 30, or 43, wherein the recombinant antibody specifically binds to LIF. In certain embodiments, the antibody is formulated with a pharmaceutically acceptable diluent, carrier, or excipient to form a pharmaceutical composition.

In another aspect described herein is a recombinant antibody that binds LIF, wherein the antibody comprises: a heavy chain variable domain comprising a heavy chain CDR1 amino acid sequence set forth in SEQ ID NO: 1, a heavy chain CDR2 amino acid sequence set forth in SEQ ID NO: 9, and a heavy chain CDR3 amino acid sequence set forth in SEQ ID NO: 15, and a light chain variable domain comprising a light chain CDR1 amino acid sequence set forth in SEQ ID NO: 21, a light chain CDR2 amino acid sequence set forth in SEQ ID NO: 25, and a light chain CDR3 amino acid sequence set forth in SEQ ID NO: 29. In certain embodiments, the antibody comprises a heavy chain variable region comprising the amino acid sequence set forth in SEQ ID NO: 72. In certain embodiments, the antibody comprises a light chain variable region comprising the amino acid sequence set forth in SEQ ID NO: 76. In certain embodiments, the antibody comprises a heavy chain variable region comprising the amino acid sequence set forth in SEQ ID NO: 72; and a light chain variable region comprising the amino acid sequence set forth in SEQ ID NO: 76. In certain embodiments, the antibody is formulated with a pharmaceutically acceptable diluent, carrier, or excipient to form a pharmaceutical composition.

In another aspect described herein is a recombinant antibody that specifically binds LIF comprising: a) a light chain comprising an amino acid sequence at least 90%, 95%, 97%, 98%, or 99% identical to the amino acid sequence set forth in any one of SEQ ID NOs: 91-94; and b) a heavy chain comprising an amino acid sequence at least 90%, 95%, 97%, 98%, or 99% identical to the amino acid sequence set forth in any one of SEQ ID NOs: 87-90, wherein the recombinant antibody specifically binds to LIF. In certain embodiments, the light chain has the amino acid sequence set forth in any one of SEQ ID NOs: 91-94; and the heavy chain has the amino acid sequence set forth in any one of SEQ ID NOs: 87-90. In certain embodiments, the light chain has the amino acid sequence set forth in SEQ ID NO: 92; and the heavy chain has the amino acid sequence set forth in SEQ ID NO: 88. In certain embodiments, the antibody is formulated with a pharmaceutically acceptable diluent, carrier, or excipient to form a pharmaceutical composition.

In another aspect described herein is a recombinant antibody that binds LIF, wherein the antibody comprises: a heavy chain CDR1 having an amino acid sequence at least 90% identical to SEQ ID NO: 1, a heavy chain CDR2 having an amino acid sequence at least 90% identical to SEQ ID NO: 9, a heavy chain CDR3 having an amino acid sequence at least 90% identical to SEQ ID NO: 15, a light chain CDR1 having an amino acid sequence at least 90% identical to SEQ ID NO: 21, a light chain CDR2 having an amino acid sequence at least 90% identical to SEQ ID NO: 25, and a light chain CDR3 having an amino acid sequence at least 90% identical to SEQ ID NO: 29. In certain embodiments, the antibody is formulated with a pharmaceutically acceptable diluent, carrier, or excipient to form a pharmaceutical composition.

In another aspect herein is a recombinant antibody that binds LIF, wherein the antibody comprises: a heavy chain CDR1 having an amino acid sequence that contains no more than 3, 2 or 1 amino acid substitutions, deletions or insertions as compared to SEQ ID NO: 1 with, a heavy chain CDR2 having an amino acid sequence that contains no more than 3, 2 or 1 amino acid substitutions, deletions or insertions as compared to SEQ ID NO: 9, a heavy chain CDR3 having an amino acid sequence that contains no more than 3, 2, or 1 amino acid substitutions, deletions or insertions as compared to SEQ ID NO: 15, a light chain CDR1 having an amino acid sequence that contains no more than 3, 2 or 1 amino acid substitutions, deletions or insertions as compared to SEQ ID NO: 21, a light chain CDR2 having an amino acid sequence that contains no more than 3, 2 or 1 amino acid substitutions, deletions or insertions as compared to SEQ ID NO: 25, and a light chain CDR3 having an amino acid sequence that contains no more than 3, 2 or 1 amino acid substitutions, deletions or insertions as compared to SEQ ID NO: 29. In certain embodiments, the antibody is formulated with a pharmaceutically acceptable diluent, carrier, or excipient to form a pharmaceutical composition.

In another aspect described herein is a recombinant antibody that binds LIF and competes with an antibody defined by: a heavy chain CDR1 having an amino acid sequence set forth in SEQ ID NO: 1, a heavy chain CDR2 having an amino acid sequence set forth in SEQ ID NO: 9, a heavy chain CDR3 having an amino acid sequence set forth in SEQ ID NO: 15, a light chain CDR1 having an amino acid sequence set forth in SEQ ID NO: 21, a light chain CDR2 having an amino acid sequence set forth in SEQ ID NO: 25, and a light chain CDR3 having an amino acid sequence set forth in SEQ ID NO: 29. In certain embodiments, the antibody is humanized. In certain embodiments, the antibody is formulated with a pharmaceutically acceptable diluent, carrier, or excipient to form a pharmaceutical composition.

In another aspect described herein is an isolated monoclonal antibody, wherein, when bound to human LIF, the monoclonal antibody binds to at least one of the following residues: A13, I14, R15, H16, P17, C18, H19, N20, Q25, Q29, Q32, D120, R123, S127, N128, L130, C131, C134, S135, H138 of SEQ ID NO:98. In certain embodiments, the monoclonal antibody binds to at least A13. In certain embodiments, the monoclonal antibody binds to at least I14. In certain embodiments, the monoclonal antibody binds to at least R15. In certain embodiments, the monoclonal antibody binds to at least H16. In certain embodiments, the monoclonal antibody binds to at least P17. In certain embodiments, the monoclonal antibody binds to at least C18. In certain embodiments, the monoclonal antibody binds to at least H19. In certain embodiments, the monoclonal antibody binds to at least N20. In certain embodiments, the monoclonal antibody binds to at least Q25. In certain embodiments, the monoclonal antibody binds to at least Q29. In certain embodiments, the monoclonal antibody binds to at least Q32. In certain embodiments, the monoclonal antibody binds to at least D120. In certain embodiments, the monoclonal antibody binds to at least R123. In certain embodiments, the monoclonal antibody binds to at least S127. In certain embodiments, the monoclonal antibody binds to at least N128. In certain embodiments, the monoclonal antibody binds to at least L130. In certain embodiments, the monoclonal antibody binds to at least C131. In certain embodiments, the monoclonal antibody binds to at least C134. In certain embodiments, the monoclonal antibody binds to at least S135. In certain embodiments, the monoclonal antibody binds to at least H138. In certain embodiments, the monoclonal antibody binds to two distinct alpha helices of human LIF, wherein the two distinct alpha helices are separated by a plurality of amino acids. In certain embodiments, the monoclonal antibody blocks binding of human LIF to human gp130. In certain embodiments, the antibody blocks the biological activity of human LIF in cell culture model. In certain embodiments, the biological activity is LIF-induced STAT3 phosphorylation. In certain embodiments, the antibody is chimeric, humanized, or human. In certain embodiments, a pharmaceutical composition comprises the isolated monoclonal antibody and a pharmaceutically acceptable diluent, carrier, or excipient. In certain embodiments, the pharmaceutical composition is formulated for intravenous injection. In certain embodiments, the isolated monoclonal antibody or the pharmaceutical composition is for use in a method of treating cancer. In certain embodiments, described herein is a method of treating an individual diagnosed with or suspected of having cancer comprising administering to the individual the monoclonal antibody or the pharmaceutical composition.

In another aspect described herein is an isolated monoclonal antibody, wherein, when bound to human LIF, the monoclonal antibody binds to at least one of the following residues: A13, I14, R15, H16, P17, C18, H19, N20, Q25, Q29, Q32, D120, R123, S127, N128, L130, C131, C134, S135, H138 of SEQ ID NO: 98. In certain embodiments, the monoclonal antibody binds to at least to at least two of the following residues: A13, I14, R15, H16, P17, C18, H19, N20, Q25, Q29, Q32, D120, R123, S127, N128, L130, C131, C134, S135, H138 of SEQ ID NO:98. In certain embodiments, the monoclonal antibody binds to at least to at least five of the following residues: A13, I14, R15, H16, P17, C18, H19, N20, Q25, Q29, Q32, D120, R123, S127, N128, L130, C131, C134, S135, H138 of SEQ ID NO: 98. In certain embodiments, the monoclonal antibody binds to at least to at least 10 of the following residues: A13, I14, R15, H16, P17, C18, H19, N20, Q25, Q29, Q32, D120, R123, S127, N128, L130, C131, C134, S135, H138 of SEQ ID NO: 98. In certain embodiments, the monoclonal antibody binds to all of the following residues: A13, I14, R15, H16, P17, C18, H19, N20, Q25, Q29, Q32, D120, R123, S127, N128, L130, C131, C134, S135, H138 of SEQ ID NO: 98. In certain embodiments, the monoclonal antibody binds to two distinct alpha helices of human LIF, wherein the two distinct alpha helices are separated by a plurality of amino acids. In certain embodiments, the monoclonal antibody blocks binding of human LIF to human gp130. In certain embodiments, the antibody blocks the biological activity of human LIF in cell culture model. In certain embodiments, the biological activity is LIF-induced STAT3 phosphorylation. In certain embodiments, the antibody is chimeric, humanized, or human. In certain embodiments, a pharmaceutical composition comprises the isolated monoclonal antibody and a pharmaceutically acceptable diluent, carrier, or excipient. In certain embodiments, the pharmaceutical composition is formulated for intravenous injection. In certain embodiments, the isolated monoclonal antibody or the pharmaceutical composition is for use in a method of treating cancer. In certain embodiments, described herein is a method of treating an individual diagnosed with or suspected of having cancer comprising administering to the individual the monoclonal antibody or the pharmaceutical composition.

In another aspect described herein is an isolated monoclonal antibody wherein the VH-CDR1 comprises an amino acid sequence that differs from that set forth in SEQ ID NO: 1 (GFTFSHAWMI-1) by 0, 1, 2, 3, or 4 amino acid residues, wherein the VH-CDR2 comprises an amino acid sequence that differs from that set forth in SEQ ID NO: 9 (QIKAKSD-DYATYYAESVKG) by 0, 1, 2, 3, or 4 amino acid residues, wherein the VH-CDR3 comprises an amino acid sequence that differs from that set forth in SEQ ID NO: 15 (TCWEWDLDF) by 0, 1, 2, 3, or 4 amino acid residues, wherein the VL-CDR1 comprises an amino acid sequence that differs from that set forth in SEQ ID NO: 21 (RSSQSLLDSDGHTYLN) by 0, 1, 2, 3, or 4 amino acid residues, wherein the VL-CDR2 comprises an amino acid sequence that differs from that set forth in SEQ ID NO: 25 (SVSNLES) by 0, 1, 2, 3, or 4 amino acid residues, wherein the VL-CDR3 comprises an amino acid sequence that differs from that set forth in SEQ ID NO: 29 (MQATHAPPYT) by 0, 1, 2, 3, or 4 amino acid residues, and wherein the monoclonal antibody binds to at least one of the following residues: A13, I14, R15, H16, P17, C18, H19, N20, Q25, Q29, Q32, D120, R123, S127, N128, L130, C131, C134, S135, H138 of SEQ ID NO: 98. In certain embodiments, the monoclonal antibody binds to at least to at least two of the following residues: A13, I14, R15, H16, P17, C18, H19, N20, Q25, Q29, Q32, D120, R123, S127, N128, L130, C131, C134, S135, H138 of SEQ ID NO: 98. In certain embodiments, the monoclonal antibody binds to at least to at least five of the following residues: A13, I14, R15, H16, P17, C18, H19, N20, Q25, Q29, Q32, D120, R123, S127, N128, L130, C131, C134, S135, H138 of SEQ ID NO: 98. In certain embodiments, the monoclonal antibody binds to at least to at least 10 of the following residues: A13, I14, R15, H16, P17, C18, H19, N20, Q25, Q29, Q32, D120, R123, S127, N128, L130, C131, C134, S135, H138 of SEQ ID NO: 98. In certain embodiments, the monoclonal antibody binds to all of the following residues: A13, I14, R15, H16, P17, C18, H19, N20, Q25, Q29, Q32, D120, R123, S127, N128, L130, C131, C134, S135, H138 of SEQ ID NO: 98. In certain embodiments, the monoclonal antibody binds to two distinct alpha helices of human LIF, wherein the two distinct alpha helices are separated by a plurality of amino acids. In certain embodiments, the monoclonal antibody blocks binding of human LIF to human gp130. In certain embodiments, the antibody blocks the biological activity of human LIF in cell culture model. In certain embodiments, the biological activity is LIF-induced STAT3 phosphorylation. In certain embodiments, the antibody is chimeric, humanized, or human. In certain embodiments, a pharmaceutical composition comprises the isolated monoclonal antibody and a pharmaceutically acceptable diluent, carrier, or excipient. In certain embodiments, the pharmaceutical composition is formulated for intravenous injection. In certain embodiments, the isolated monoclonal antibody or the pharmaceutical composition is for use in a method of treating cancer. In certain embodiments, described herein is a method of treating an individual diagnosed with or suspected of having cancer comprising administering to the individual the monoclonal antibody or the pharmaceutical composition.

In another aspect described herein is an isolated monoclonal antibody wherein the VH-CDR1 comprises an amino acid sequence that differs from that set forth in SEQ ID NO: 1 (GFTFSHAWMI-1) by 0, 1, 2, 3, or 4 amino acid residues, wherein the VH-CDR2 comprises an amino acid sequence that differs from that set forth in SEQ ID NO: 9 (QIKAKSD-DYATYYAESVKG) by 0, 1, 2, 3, or 4 amino acid residues, wherein the VH-CDR3 comprises an amino acid sequence that differs from that set forth in SEQ ID NO: 95 (TSWEWDLDF) by 0, 1, 2, 3, or 4 amino acid residues, wherein the VL-CDR1 comprises an amino acid sequence that differs from that set forth in SEQ ID NO: 21 (RSSQSLLDSDGHTYLN) by 0, 1, 2, 3, or 4 amino acid residues, wherein the VL-CDR2 comprises an amino acid sequence that differs from that set forth in SEQ ID NO: 25 (SVSNLES) by 0, 1, 2, 3, or 4 amino acid residues, wherein the VL-CDR3 comprises an amino acid sequence that differs from that set forth in SEQ ID NO: 29 (MQATHAPPYT) by 0, 1, 2, 3, or 4 amino acid residues, and wherein the monoclonal antibody binds to at least one of the following residues: A13, I14, R15, H16, P17, C18, H19, N20, Q25, Q29, Q32, D120, R123, S127, N128, L130, C131, C134, S135, H138 of SEQ ID NO: 98. In certain embodiments, the monoclonal antibody binds to at least two of the following residues: A13, I14, R15, H16, P17, C18, H19, N20, Q25, Q29, Q32, D120, R123, S127, N128, L130, C131, C134, S135, H138 of SEQ ID NO: 98. In certain embodiments, the monoclonal antibody binds to at least five of the following residues: A13, I14, R15, H16, P17, C18, H19, N20, Q25, Q29, Q32, D120, R123, S127, N128, L130, C131, C134, S135, H138 of SEQ ID NO: 98. In certain embodiments, the monoclonal antibody binds to at least 10 of the following residues: A13, I14, R15, H16, P17, C18, H19, N20, Q25, Q29, Q32, D120, R123, S127, N128, L130, C131, C134, S135, H138 of SEQ ID NO: 98. In certain embodiments, the monoclonal antibody binds to all of the following residues: A13, I14, R15, H16, P17, C18, H19, N20, Q25, Q29, Q32, D120, R123, S127, N128, L130, C131, C134, S135, H138 of SEQ ID NO: 98. In certain embodiments, the monoclonal antibody binds to two distinct alpha helices of human LIF, wherein the two distinct alpha helices are separated by a plurality of amino acids. In certain embodiments, the monoclonal antibody blocks binding of human LIF to human gp130. In certain embodiments, the antibody blocks the biological activity of human LIF in cell culture model. In certain embodiments, the biological activity is LIF-induced STAT3 phosphorylation. In certain embodiments, the antibody is chimeric, humanized, or human. In certain embodiments, a pharmaceutical composition comprises the isolated monoclonal antibody and a pharmaceutically acceptable diluent, carrier, or excipient. In certain embodiments, the pharmaceutical composition is formulated for intravenous injection. In certain embodiments, the pharmaceutical composition is formulated for intracerebral injection. In certain embodiments, the isolated monoclonal antibody or the pharmaceutical composition is for use in a method of treating cancer. In certain embodiments, described herein is a method of treating an individual diagnosed with or suspected of having cancer comprising administering to the individual the monoclonal antibody or the pharmaceutical composition.

In a certain aspect, described herein, is a recombinant antibody that specifically binds Leukemia Inhibitory Factor (LIF) comprising: a heavy chain complementarity determining region 1 (VH-CDR1) comprising an amino acid sequence set forth in SEQ ID NO: 2; a heavy chain complementarity determining region 2 (VH-CDR2) comprising an amino acid sequence set forth in SEQ ID NO: 10; a heavy chain complementarity determining region 3 (VH-CDR3) comprising an amino acid sequence set forth in SEQ ID NO: 15; a light chain complementarity determining region 1 (VL-CDR1) comprising an amino acid sequence set forth in SEQ ID NO: 22; and a light chain complementarity determining region 2 (VL-CDR2) comprising an amino acid sequence set forth in SEQ ID NO: 26; and a light chain complementarity determining region 3 (VL-CDR3) comprising an amino acid sequence set forth in SEQ ID NO: 29.

In a certain aspect, described herein, is a recombinant antibody that specifically binds Leukemia Inhibitory Factor (LIF) comprising: a heavy chain complementarity determining region 1 (VH-CDR1) comprising an amino acid sequence set forth in SEQ ID NO: 3; a heavy chain complementarity determining region 2 (VH-CDR2) comprising an amino acid sequence set forth in SEQ ID NO: 9; a heavy chain complementarity determining region 3 (VH-CDR3) comprising an amino acid sequence set forth in SEQ ID NO: 16; a light chain complementarity determining region 1 (VL-CDR1) comprising an amino acid sequence set forth in SEQ ID NO: 21; and a light chain complementarity determining region 2 (VL-CDR2) comprising an amino acid sequence set forth in SEQ ID NO: 25; and a light chain complementarity determining region 3 (VL-CDR3) comprising an amino acid sequence set forth in SEQ ID NO: 29.

In a certain aspect, described herein, is a recombinant antibody that specifically binds Leukemia Inhibitory Factor (LIF) comprising: a heavy chain complementarity determining region 1 (VH-CDR1) comprising an amino acid sequence set forth in SEQ ID NO: 3; a heavy chain complementarity determining region 2 (VH-CDR2) comprising an amino acid sequence set forth in SEQ ID NO: 10; a heavy chain complementarity determining region 3 (VH-CDR3) comprising an amino acid sequence set forth in SEQ ID NO: 16; a light chain complementarity determining region 1 (VL-CDR1) comprising an amino acid sequence set forth in SEQ ID NO: 22; and a light chain complementarity determining region 2 (VL-CDR2) comprising an amino acid sequence set forth in SEQ ID NO: 26; and a light chain complementarity determining region 3 (VL-CDR3) comprising an amino acid sequence set forth in SEQ ID NO: 29.

In a certain aspect described herein, is a recombinant antibody that specifically binds Leukemia Inhibitory Factor (LIF) comprising: a) a heavy chain complementarity determining region 1 (VH-CDR1) comprising an amino acid sequence set forth in SEQ ID NO: 3; b) a heavy chain complementarity determining region 2 (VH-CDR2) comprising an amino acid sequence set forth in SEQ ID NO: 10; c) a heavy chain complementarity determining region 3 (VH-CDR3) comprising an amino acid sequence set forth in SEQ ID NO: 16; d) a light chain complementarity determining region 1 (VL-CDR1) comprising an amino acid sequence set forth in SEQ ID NO: 22; e) a light chain complementarity determining region 2 (VL-CDR2) comprising an amino acid sequence set forth in SEQ ID NO: 26; and f) a light chain complementarity determining region 3 (VL-CDR3) comprising an amino acid sequence set forth in SEQ ID NO: 29, wherein the recombinant antibody specifically binds to LIF. In certain embodiments, the recombinant antibody binds to glycosylated LIF. In certain embodiments, the recombinant antibody is humanized. In certain embodiments, the recombinant antibody is deimmunized. In certain embodiments, the recombinant antibody comprises two immunoglobulin heavy chains and two immunoglobulin light chains. In certain embodiments, the recombinant antibody comprises a Fab, F(ab)$_2$, single-domain antibody, a single chain variable fragment (scFv), or a nanobody. In certain embodiments, the recombinant antibody specifically binds LIF with a dissociation constant ($K_D$) of less than about 200 picomolar. In certain embodiments, the recombinant antibody specifically binds LIF with a dissociation constant ($K_D$) of less than about 100 picomolar. In certain embodiments, the VH-CDR1 comprises an amino acid sequence set forth in SEQ ID NO: 1 (GFTFSHAWMH), wherein the VH-CDR2 comprises an amino acid sequence set forth in SEQ ID NO: 9 (QIKAKSDDYATYYAESVKG), wherein the VH-CDR3 comprises an amino acid sequence set forth in SEQ ID NO: 15 (TCWEWDLDF), wherein the VL-CDR1 comprises an amino acid sequence set forth in SEQ ID NO: 21 (RSSQSLLDSDGHTYLN), wherein the VL-CDR2 comprises an amino acid sequence set forth in SEQ ID NO: 25 (SVSNLES), and wherein the VL-CDR3 comprises an amino acid sequence set forth in SEQ ID NO: 29 (MQATHAPPYT). In certain embodiments, the VH-CDR1 comprises an amino acid sequence set forth in SEQ ID NO: 1 (GFTFSHAWMH), wherein the VH-CDR2 comprises an amino acid sequence set forth in SEQ ID NO: 9 (QIKAKSDDYATYYAESVKG), wherein the VH-CDR3 comprises an amino acid sequence set forth in SEQ ID NO: 95 (TSWEWDLDF), wherein the VL-CDR1 comprises an amino acid sequence set forth in SEQ ID NO: 21 (RSSQSLLDSDGHTYLN), wherein the VL-CDR2 comprises an amino acid sequence set forth in SEQ ID NO: 25 (SVSNLES), and wherein the VL-CDR3 comprises an amino acid sequence set forth in SEQ ID NO: 29 (MQATHAPPYT). In certain embodiments, the recombinant antibody comprises a VH sequence at least about 80% identical to the amino acid sequence set forth in SEQ ID NO: 72; and a VL sequence at least about 80% identical to the amino acid sequence set forth in SEQ ID NO: 76. In certain embodiments, the recombinant antibody comprises VH sequence at least about 90% identical to the amino acid sequence set forth in SEQ ID NO: 72; and a VL sequence at least about 90% identical to the amino acid sequence set forth in SEQ ID NO: 76. In certain embodiments, the recombinant antibody blocks binding of human LIF to human gp130. In certain embodiments, the recombinant antibody when bound to LIF, binds to at least one of the following residues: A13, I14, R15, H16, P17, C18, H19, N20, Q25, Q29, Q32, D120, R123, S127, N128, L130, C131, C134, S135, H138 of SEQ ID NO:98. In certain embodiments, the recombinant antibody when bound to LIF, binds all of the following residues: A13, I14, R15, H16, P17, C18, H19, N20, Q25, Q29, Q32, D120, R123, S127, N128, L130, C131, C134, S135, H138 of SEQ ID NO:98. In certain embodiments, the recombinant antibody is included in a pharmaceutical composition comprising the recombinant antibody and a pharmaceutically acceptable carrier. In certain embodiments, the recombinant antibody or the pharmaceutical composition is for use in a method of treating cancer. In certain embodiments, a method of treating cancer in an individual comprises administering the recombinant antibody or the pharmaceutical composition to the individual. In certain embodiments, the cancer comprises glioblastoma, pancreatic cancer, ovarian cancer, colon cancer, prostate cancer, or lung cancer. In certain embodiments, the cancer comprises glioblastoma, pancreatic cancer, ovarian cancer, colon cancer, prostate cancer, or lung cancer. In certain embodiments, a method of preparing a cancer treatment for treating a subject with cancer comprises admixing a pharmaceutically acceptable carrier and the recombinant antibody.

In a certain aspect described herein, is a recombinant antibody that specifically binds Leukemia Inhibitory Factor (LIF) comprising: a) a heavy chain complementarity determining region 1 (VH-CDR1) comprising an amino acid sequence set forth in any one of SEQ ID NOs: 4-7 or 33; b) a heavy chain complementarity determining region 2 (VH-CDR2) comprising an amino acid sequence set forth in any one of SEQ ID NOs: 11-13 or 35; c) a heavy chain complementarity determining region 3 (VH-CDR3) comprising an amino acid sequence set forth in any one of SEQ ID NOs: 17-19 or 37; d) a light chain complementarity determining region 1 (VL-CDR1) comprising an amino acid sequence set forth in any one of SEQ ID NOs: 21-23 or 39; e) a light chain complementarity determining region 2 (VL-CDR2) comprising an amino acid sequence set forth in any one of SEQ ID NOs: 25-27 or 41; and f) a light chain complementarity determining region 3 (VL-CDR3) comprising an amino acid sequence set forth in any one of SEQ ID NOs: 29, 30, or 43; wherein the recombinant antibody specifically binds to LIF. In certain embodiments, the recombinant antibody binds to glycosylated LIF. In certain embodiments, the recombinant antibody is humanized. In certain embodiments, the recombinant antibody is deimmunized. In certain embodiments, the recombinant antibody comprises two immunoglobulin heavy chains and two immunoglobulin light chains. In certain embodiments, the recombinant antibody is a Fab, F(ab)$_2$, single-domain antibody, a single chain variable fragment (scFv), or a nanobody. In certain embodiments, the recombinant antibody specifically binds LIF with a dissociation constant ($K_D$) of less than about 200 picomolar. In certain embodiments, the -CDR1 comprises an amino acid sequence set forth in SEQ ID NO: 6 (NAWMH), wherein the VH-CDR2 comprises an amino acid sequence set forth in SEQ ID NO: 12 (IKDKSDNYAT), wherein the VH-CDR3 comprises an amino acid sequence set forth in SEQ ID NO: 18 (WEWYLDF), wherein the VL-CDR1 comprises an amino acid sequence set forth in SEQ ID NO: 22 (QSLLDSDGHTY), wherein the VL-CDR2 comprises an amino acid sequence set forth in SEQ ID NO: 26 (SVS), and wherein the VL-CDR3 comprises an amino acid sequence set forth in SEQ ID NO: 29 (MQATHAPPYT). In certain embodiments, the VH-CDR1 comprises an amino acid sequence set forth in SEQ ID NO: 7 (SKFMY), wherein the VH-CDR2 comprises an amino acid sequence set forth in SEQ ID NO: 13 (WIYPGDGDTEYNQKFSE), wherein the VH-CDR3 comprises an amino acid sequence set forth in SEQ ID NO: 19 (RDYHSSHFAY), wherein the VL-CDR1 comprises an amino acid sequence set forth in SEQ ID NO: 23 (RSSQSLLHNNGNTYLS), wherein the VL-CDR2 comprises an amino acid sequence set forth in SEQ ID NO: 27 (QVSNRFS), and wherein the VL-CDR3 comprises an amino acid sequence set forth in SEQ ID NO: 30 (GQGTQYPYT). In certain embodiments, the VH-CDR1 comprises an amino acid sequence set forth in SEQ ID NO: 33 (TAGMQ), wherein the VH-CDR2 comprises an amino acid sequence set forth in SEQ ID NO: 35 (WINTQSGEPQYVDDFRG), wherein the VH-CDR3 comprises an amino acid sequence set forth in SEQ ID NO: 37 (WALYSEYDVMDY), wherein the VL-CDR1 comprises an amino acid sequence set forth in SEQ ID NO: 39 (KASENVDSYVS), wherein the VL-CDR2 comprises an amino acid sequence set forth in SEQ ID NO: 41 (GASNRYT), and wherein the VL-CDR3 comprises an amino acid sequence set forth in SEQ ID NO: 43 (GQSYRYPPT). In certain embodiments, the monoclonal antibody blocks binding of human LIF to human gp130. In certain embodiments, the recombinant antibody is included in a pharmaceutical composition comprising the recombinant antibody and a pharmaceutically acceptable carrier. In certain embodiments, the recombinant antibody or the pharmaceutical composition is for use in a method of treating cancer. In certain embodiments, a method of treating cancer in an individual comprises administering the recombinant antibody or the pharmaceutical composition to the individual. In certain embodiments, the cancer comprises glioblastoma, pancreatic cancer, ovarian cancer, colon cancer, prostate cancer, or lung cancer. In certain embodiments, the cancer comprises glioblastoma, pancreatic cancer, ovarian cancer, colon cancer, prostate cancer, or lung cancer. In certain embodiments, a method of preparing a cancer treatment for treating a subject with cancer comprises admixing a pharmaceutically acceptable carrier and the recombinant antibody.

In a certain aspect described herein, is a recombinant antibody that specifically binds Leukemia Inhibitory Factor (LIF) comprising: a) a VH-CDR1 comprising an amino acid sequence set forth in SEQ ID NO: 1 (GFTFSHAWMH); b) a the VH-CDR2 comprising an amino acid sequence set forth in SEQ ID NO: 9 (QIKAKSDDYATYYAESVKG); c) a VH-CDR3 comprising an amino acid sequence set forth in SEQ ID NO: 15 (TCWEWDLDF), d) a VL-CDR1 comprising an amino acid sequence set forth in SEQ ID NO: 21 (RSSQSLLDSDGHTYLN), e) a VL-CDR2 comprising an amino acid sequence set forth in SEQ ID NO: 25 (SVSNLES); and f) a VL-CDR3 comprising an amino acid sequence set forth in SEQ ID NO: 29 (MQATHAPPYT); wherein the cysteine residue of SEQ ID NO: 15 is any amino acid except for tyrosine, tryptophan, histidine, lysine or arginine. In certain embodiments, the recombinant antibody binds to glycosylated LIF. In certain embodiments, the recombinant antibody is humanized. In certain embodiments, the recombinant antibody is deimmunized. In certain embodiments, the recombinant antibody comprises two immunoglobulin heavy chains and two immunoglobulin light chains. In certain embodiments, the recombinant antibody is a Fab, F(ab)$_2$, single-domain antibody, a single chain variable fragment (scFv), or a nanobody. In certain embodiments, the recombinant antibody specifically binds LIF with a dissociation constant ($K_D$) of less than about 200 picomolar. In certain embodiments, the recombinant antibody blocks binding of human LIF to human gp130. In certain embodiments, the recombinant antibody is included in a pharmaceutical composition comprising the recombinant antibody and a pharmaceutically acceptable carrier. In certain embodiments, the recombinant antibody or the pharmaceutical composition is for use in a method of treating cancer. In certain embodiments, a method of treating cancer in an individual comprises administering the recombinant antibody or the pharmaceutical composition to the individual. In certain embodiments, the cancer comprises glioblastoma, pancreatic cancer, ovarian cancer, colon cancer, prostate cancer, or lung cancer. In certain embodiments, the cancer comprises glioblastoma, pancreatic cancer, ovarian cancer, colon cancer, prostate cancer, or lung cancer. In certain embodiments, a method of preparing a cancer treatment for treating a subject with cancer comprises admixing a pharmaceutically acceptable carrier and the recombinant antibody.

BRIEF DESCRIPTION OF THE DRAWINGS

FIG. 8A shows the effect of r5D8 on inhibition of growth of ovarian cancer cells in an syngeneic mouse model.

FIG. 8B shows the individual measurements of tumors at day 25.

FIG. 8C illustrates that h5D8 shows a significant reduction in tumor growth when administered at 200 μg/mouse twice weekly ($p<0.05$). Symbols are mean+SEM, statistical significance compared with vehicle (with unpaired non-parametric Mann-Whitney U-test).

DETAILED DESCRIPTION

Certain Definitions

Figure 1:
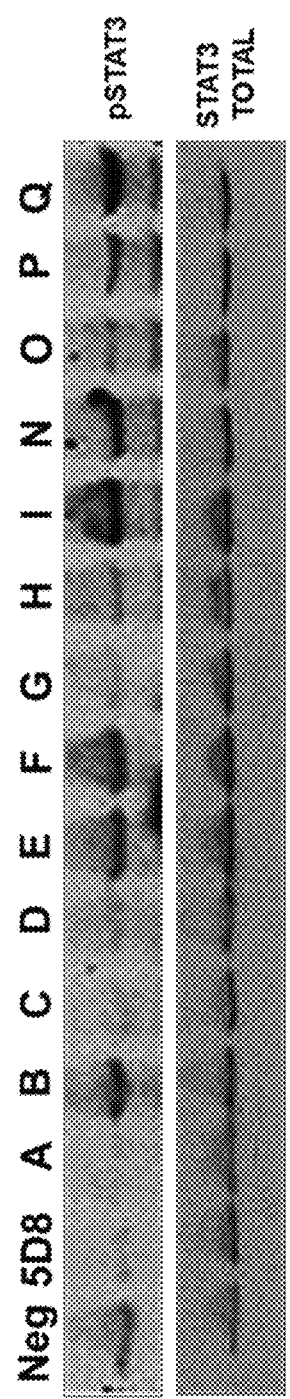
FIG. 1 depicts a western blot showing inhibition of LIF-induced STAT3 phosphorylation of different anti-LIF humanized antibodies.

Unless otherwise defined, all technical terms used herein have the same meaning as commonly understood by one of ordinary skill in the art to which this invention belongs. As used in this specification and the appended claims, the singular forms "a," "an," and "the" include plural references unless the context clearly dictates otherwise. Any reference to "or" herein is intended to encompass "and/or" unless otherwise stated.

As used herein, unless otherwise indicated, the term "about" refers to an amount that is near the stated amount, for example by 10%, 5%, or 1%.

As used herein the terms "individual," "subject," and "patient" are used interchangeably and include humans diagnosed with or suspected of being afflicted with a tumor, a cancer or other neoplasm.

As used herein, unless otherwise indicated, the term "antibody" includes antigen binding fragments of antibodies, i.e. antibody fragments that retain the ability to bind specifically to the antigen bound by the full-length antibody, e.g. fragments that retain one or more CDR regions. Examples of antibody fragments include, but are not limited to, Fab, Fab', F(ab')2, and Fv fragments; diabodies; linear antibodies; heavy chain antibodies, single-chain antibody molecules, e.g. single-chain variable region fragments (scFv), nanobodies and multispecific antibodies formed from antibody fragments with separate specificities, such as a bispecific antibody. In certain embodiments, the antibodies are humanized in such a way as to reduce an individual's immune response to the antibody. For example the antibodies may be chimeric, e.g. non-human variable region with human constant region, or CDR grafted, e.g. non-human CDR regions with human constant region and variable region framework sequences. In certain embodiments, antibodies are deimmunized after humanization. Deimmunization involves removing or mutating one or more T-cell epitopes in the constant region of the antibody. In certain embodiments, the antibodies described herein are monoclonal. As used herein a "recombinant antibody" is an antibody that comprises an amino acid sequence derived from two different species or, or two different sources, and includes synthetic molecules, for example, an antibody that comprises a non-human CDR and a human framework or constant region. In certain embodiments, recombinant antibodies of the present invention are produced from a recombinant DNA molecule or synthesized.

The terms "cancer" and "tumor" relate to the physiological condition in mammals characterized by deregulated cell growth. Cancer is a class of diseases in which a group of cells display uncontrolled growth or unwanted growth. Cancer cells can also spread to other locations, which can lead to the formation of metastases. Spreading of cancer cells in the body can, for example, occur via lymph or blood. Uncontrolled growth, intrusion, and metastasis formation are also termed malignant properties of cancers. These malignant properties differentiate cancers from benign tumors, which typically do not invade or metastasize.

Percent (%) sequence identity with respect to a reference polypeptide or antibody sequence is the percentage of amino acid residues in a candidate sequence that are identical with the amino acid residues in the reference polypeptide or antibody sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are known for instance, using publicly available computer software such as BLAST, BLAST-2, ALIGN, or Megalign (DNASTAR) software. Appropriate parameters for aligning sequences are able to be determined, including algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows: 100 times the fraction X/Y, where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "epitope" includes any determinant capable of being bound by an antigen binding protein, such as an antibody. An epitope is a region of an antigen that is bound by an antigen binding protein that targets that antigen, and when the antigen is a protein, includes specific amino acids that directly contact the antigen binding protein. Most often, epitopes reside on proteins, but in some instances can reside on other kinds of molecules, such as saccharides or lipids. Epitope determinants can include chemically active surface groupings of molecules such as amino acids, sugar side chains, phosphoryl or sulfonyl groups, and can have specific three dimensional structural characteristics, and/or specific charge characteristics. Generally, antibodies specific for a particular target antigen will preferentially recognize an epitope on the target antigen in a complex mixture of proteins and/or macromolecules.

Structural Attributes of the Antibodies Described Herein

A complementarity determining region ("CDR") is a part of an immunoglobulin (antibody) variable region that is primarily responsible for the antigen binding specificity of the antibody. CDR regions are highly variable from one antibody to the next even when the antibody specifically binds the same target or epitope. A heavy chain variable region comprises three CDR regions, abbreviated VH-CDR1, VH-CDR2, and VH-CDR3; and a light chain variable region comprises three CDR regions, abbreviated VL-CDR1, VL-CDR2, and VL-CDR3. These CDR regions are ordered consecutively in the variable region with the CDR1 being the most N-terminal and the CDR3 being the most C-terminal. Interspersed between the CDRs are framework regions which contribute to the structure and display much less variability than the CDR regions. A heavy chain variable region comprises four framework regions, abbreviated VH-FR1, VH-FR2, VH-FR3, and VH-FR4; and a light chain variable region comprises four framework regions, abbreviated VL-FR1, VL-FR2, VL-FR3, and VL-FR4. Complete full-sized bivalent antibodies comprising two heavy and light chains will comprise: 12 CDRs, with three unique heavy chain CDRs and three unique light chain CDRs; 16 FR regions, with four unique heavy chain FR regions and four unique light chain FR regions. In certain embodiments, the antibodies described herein minimally comprise three heavy chain CDRs. In certain embodiments, the antibodies described herein minimally comprise three light chain CDRs. In certain embodiments, the antibodies described herein minimally comprise three heavy chain CDRs and three light chain CDRs. The precise amino acid sequence boundaries of a given CDR or FR can be readily determined using any of a number of well-known schemes, including those described by Kabat et al. (1991), "Sequences of Proteins of Immunological Interest," 5th Ed. Public Health Service, National Institutes of Health, Bethesda, Md. ("Kabat" numbering scheme); Al-Lazikani et al., (1997) *JMB* 273,927-948 ("Chothia" numbering scheme); MacCallum et al., *J. Mol. Biol.* 262:732-745 (1996), "Antibody-antigen interactions: Contact analysis and binding site topography," ("Contact" numbering scheme); Lefranc M P et al., "IMGT unique numbering for immunoglobulin and T cell receptor variable domains and Ig superfamily V-like domains," Dev Comp *Immunol*, 2003 January; 27(1):55-77 ("IMGT" numbering scheme); and Honegger A and Pluckthun A, "Yet another numbering scheme for immunoglobulin variable domains: an automatic modeling and analysis tool," *J Mol Biol*, 2001 Jun. 8; 309(3):657-70, ("Aho" numbering scheme). CDRs are identified herein from variable sequences provided using different numbering systems, herein with the Kabat, the IMGT, the Chothia numbering system, or any combination of the three. The boundaries of a given CDR or FR may vary depending on the scheme used for identification. For example, the Kabat scheme is based on structural alignments, while the Chothia scheme is based on structural information. Numbering for both the Kabat and Chothia schemes is based upon the most common antibody region sequence lengths, with insertions accommodated by insertion letters, for example, "30a," and deletions appearing in some antibodies. The two schemes place certain insertions and deletions ("indels") at different positions, resulting in differential numbering. The Contact scheme is based on analysis of complex crystal structures and is similar in many respects to the Chothia numbering scheme.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three CDRs (See e.g., Kindt et al. Kuby *Immunology, 6th ed.*, W.H. Freeman and Co., page 91(2007)). A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively (See e.g., Portolano et al., *J Immunol*. 150:880-887 (1993); Clarkson et al., Nature 352:624-628 (1991)). In certain embodiments, the antibodies described herein comprise variable regions of rat origin. In certain embodiments, the antibodies described herein comprise CDRs of rat origin. In certain embodiments, the antibodies described herein comprise variable regions of mouse origin. In certain embodiments, the antibodies described herein comprise CDRs of mouse origin.

Alterations (e.g., substitutions) may be made in CDRs, e.g., to improve antibody affinity. Such alterations may be made in CDR encoding codons with a high mutation rate during somatic maturation (See e.g., Chowdhury, *Methods Mol. Biol*. 207:179-196 (2008)), and the resulting variant can be tested for binding affinity. Affinity maturation (e.g., using error-prone PCR, chain shuffling, randomization of CDRs, or oligonucleotide-directed mutagenesis) can be used to improve antibody affinity (See e.g., Hoogenboom et al. in *Methods in Molecular Biology* 178:1-37 (2001)). CDR residues involved in antigen binding may be specifically identified, e.g., using alanine scanning mutagenesis or modeling (See e.g., Cunningham and Wells *Science*, 244:1081-1085 (1989)). CDR-H3 and CDR-L3 in particular are often targeted. Alternatively, or additionally, a crystal structure of an antigen-antibody complex is analyzed to identify contact points between the antibody and antigen. Such contact residues and neighboring residues may be targeted or eliminated as candidates for substitution. Variants may be screened to determine whether they contain the desired properties.

In certain embodiments, the antibodies described herein comprise a constant region in addition to a variable region. The heavy chain constant region ($C_H$) comprises four domains abbreviated $C_H1$, $C_H2$, $C_H3$, and $C_H4$, located at the C-terminal end of the full heavy chain polypeptide, C-terminal to the variable region. The light chain constant region (CO is much smaller than the $C_H$ and is located at the C-terminal end of the full light chain polypeptide, C-terminal to the variable region. The constant region is highly conserved and comprises different isotypes that are associated with slightly different functions and properties. In certain embodiments, the constant region is dispensable for antibody binding to a target antigen. In certain embodiments, the constant regions of the antibody, both heavy and light chains are dispensable for antibody binding. In certain embodiments, the antibodies described herein lack one or more of a light chain constant region, heavy chain constant region, or both. Most monoclonal antibodies are of an IgG isotype; which is further divided into four subclasses $IgG_1$, $IgG_2$, $IgG_3$, and $IgG_4$. In certain embodiments, the antibodies described herein comprise any IgG subclass. In certain embodiments, the IgG subclass comprises $IgG_1$. In certain embodiments, the IgG subclass comprises $IgG_2$. In certain embodiments, the IgG subclass comprises $IgG_3$. In certain embodiments, the IgG subclass comprises $IgG_4$.

Antibodies comprise a fragment crystallizable region (Fc region) that is responsible for binding to complement and Fc receptors. The Fc region comprises the $C_H2$, $C_H3$, and $C_H4$ regions of the antibody molecule. The Fc region of an antibody is responsible for activating complement and antibody dependent cell cytotoxicity (ADCC). The Fc region also contributes to an antibody's serum half-life. In certain embodiments, the Fc region of the antibodies described herein comprise one ore more amino acid substitutions that promote complement mediated cell lysis. In certain embodiments, the Fc region of antibodies described herein comprises one or more amino acid substitutions that promote ADCC. In certain embodiments, the Fc region of antibodies described herein comprises one or more amino acid substitutions that reduce complement mediated cell lysis. In certain embodiments, the Fc region of antibodies described herein comprises one or more amino acid substitutions that increase binding of the antibody to an Fc receptor. In certain embodiments, the Fc receptor comprises FcγRI (CD64), FcγRIIA (CD32), FcγRIIIA (CD16a), FcγRIIIB (CD16b), or any combination thereof. In certain embodiments, the Fc region of the antibodies described herein comprise one or more amino acid substitutions that increase the serum half-life of the antibody. In certain embodiments, the one or more amino acid substitutions that increase the serum half-life of the antibody increase affinity of the antibody to the neonatal Fc receptor (FcRn).

In some embodiments, the antibodies of this disclosure are variants that possesses some but not all effector functions, which make it a desirable candidate for applications in which the half-life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. Non-limiting examples of in vitro assays to assess ADCC activity of a molecule of interest are described in U.S. Pat. Nos. 5,500,362 and 5,821,337. Alternatively, non-radioactive assays methods may be employed (e.g., ACTI™ and CytoTox 96® non-radioactive cytotoxicity assays). Useful effector cells for such assays include peripheral blood mononuclear cells (PBMC), monocytes, macrophages, and Natural Killer (NK) cells.

Antibodies can have increased half-lives and improved binding to the neonatal Fc receptor (FcRn) (See e.g., US 2005/0014934). Such antibodies can comprise an Fc region with one or more substitutions therein which improve binding of the Fc region to FcRn, and include those with substitutions at one or more of Fc region residues: 238, 256, 265, 272, 286, 303, 305, 307, 311, 312, 317, 340, 356, 360, 362, 376, 378, 380, 382, 413, 424 or 434 according to the EU numbering system (See e.g., U.S. Pat. No. 7,371,826). Other examples of Fc region variants are also contemplated (See e.g., Duncan & Winter, Nature 322:738-40 (1988); U.S. Pat. Nos. 5,648,260 and 5,624,821; and WO94/29351).

Antibodies useful in the clinic are often "humanized" to reduce immunogenicity in human individuals. Humanized antibodies improve safety and efficacy of monoclonal antibody therapy. One common method of humanization is to produce a monoclonal antibody in any suitable animal (e.g., mouse, rat, hamster) and replace the constant region with a human constant region, antibodies engineered in this way are termed "chimeric". Another common method is "CDR grafting" which replaces the non-human V-FRs with human V-FRs. In the CDR grafting method all residues except for the CDR region are of human origin. In certain embodiments, the antibodies described herein are humanized. In certain embodiments, the antibodies described herein are chimeric. In certain embodiments, the antibodies described herein are CDR grafted.

Humanization generally reduces or has little effect on the overall affinity of the antibody. Described herein are antibodies that unexpectedly possess greater affinity for their target after humanization. In certain embodiments, humanization increases the affinity for the antibody by 10%. In certain embodiments, humanization increases the affinity for the antibody by 25%. In certain embodiments, humanization increases the affinity for the antibody by 35%. In certain embodiments, humanization increases the affinity for the antibody by 50%. In certain embodiments, humanization increases the affinity for the antibody by 60%. In certain embodiments, humanization increases the affinity for the antibody by 75%. In certain embodiments, humanization increases the affinity for the antibody by 100%. Affinity is suitably measured using surface plasmon resonance (SPR). In certain embodiments, affinity is measured using glycosylated human LIF. In certain embodiments, the glycosylated human LIF is immobilized to the surface of the SPR chip. In certain embodiments, the antibody binds with a $K_D$ of less than about 300 nanomolar, 200 nanomolar, 150 nanomolar, 125 nanomolar 100 nanomolar, 90 nanomolar, 80 nanomolar, 70 nanomolar, 60 nanomolar, 50 nanomolar, 40 nanomolar, or less.

Novel Antibodies of the Current Disclosure

The antibodies described herein were generated from rats and mice immunized with DNA encoding human LIF.

In certain embodiments, described herein, is an antibody that specifically binds LIF comprising a VH-CDR1 set forth in any one of SEQ ID NOs: 1-7 or 33, a VH-CDR2 set forth in any one of SEQ ID NOs: 9-13 or 35, and a VH-CDR3 set forth in any one of SEQ ID NOs: 15-19 or 37. In certain embodiments, described herein, is an antibody that specifically binds LIF comprising a VL-CDR1 set forth in any one of SEQ ID NOs: 21-23 or 39, a VL-CDR2 set forth in SEQ ID NOs: 25-27 or 41, and a VL-CDR3 set forth in any one of SEQ ID NOs: 29, 30, 43. In certain embodiments, described herein, is an antibody that specifically binds LIF comprising a VH-CDR1 set forth in any one of SEQ ID NOs: 1-7 or 33, a VH-CDR2 set forth in any one of SEQ ID NOs: 9-13 or 35, and a VH-CDR3 set forth in any one of SEQ ID NOs: 15-19 or 37, a VL-CDR1 set forth in any one of SEQ ID NOs: 21-23 or 39, a VL-CDR2 set forth in SEQ ID NOs: 25-27 or 41, and a VL-CDR3 set forth in any one of SEQ ID NOs: 29, 30, 43. In certain embodiments, the antibody specifically binds to human LIF.

In certain embodiments, the antibody that specifically binds LIF comprises one or more human heavy chain framework regions comprising: a VH-FR1 amino acid sequence at least about 80%, about 90%, or about 95% identical to the amino acid sequence set forth in any one of SEQ ID NOs: 44-47, a VH-FR2 amino acid sequence at least about 80%, about 90%, or about 95% identical to the amino acid sequence set forth in any one of SEQ ID NOs: 48-49, a VH-FR3 amino acid sequence at least about 80%, about 90%, or about 95% identical to the amino acid sequence set forth in any one of SEQ ID NOs: 50-52, or a VH-FR4 region amino acid sequence at least about 80%, about 90%, or about 95% identical to the amino acid sequence set forth in any one of SEQ ID NOs: 53-55. In certain embodiments, the one or more human heavy chain framework regions comprise a VH-FR1 amino acid sequence at least about 80%, about 90%, or about 95% identical to the amino acid sequence set forth in SEQ ID NO: 45, a VH-FR2 amino acid sequence at least about 80%, about 90%, or about 95% identical to the amino acid sequence set forth in SEQ ID NO: 49, a VH-FR3 amino acid sequence at least about 80%, about 90%, or about 95% identical to the amino acid sequence set forth in SEQ ID NO: 50, and a VH-FR4 amino acid sequence at least about 80%, about 90%, or about 95% identical to the amino acid sequence set forth in SEQ ID NO: 54. In certain embodiments, the antibody that specifically binds LIF comprises one or more human light chain framework regions comprising: a VL-FR1 amino acid sequence at least about 80%, about 90%, or about 95% identical to the amino acid sequence set forth in any one of SEQ ID NOs: 56-59, a VL-FR2 amino acid sequence at least about 80%, about 90%, or about 95% identical to the amino acid sequence set forth in any one of SEQ ID NOs: 60-63, a VL-FR3 amino acid sequence at least about 80%, about 90%, or about 95% identical to the amino acid sequence set forth in any one of SEQ ID NOs: 64-67, or a VL-FR4 amino acid sequence at least about 80%, about 90%, or about 95% identical to the amino acid sequence set forth in any one of SEQ ID NOs: 68-70. In certain embodiments, the one or more human light chain framework regions comprise a VL-FR1 amino acid sequence at least about 80%, about 90%, or about 95% identical to the amino acid sequence set forth in SEQ ID NO: 57, a VL-FR2 amino acid sequence at least about 80%, about 90%, or about 95% identical to the amino acid sequence set forth in SEQ ID NO: 61, a VL-FR3 amino acid sequence at least about 80%, about 90%, or about 95% identical to the amino acid sequence set forth in SEQ ID NO: 65, and a VL-FR4 amino acid sequence at least about 80%, about 90%, or about 95% identical to the amino acid sequence set forth in SEQ ID NO: 68. In certain embodiments, the one or more human heavy chain framework regions and the one or more human light chain regions comprise a VH-FR1 amino acid sequence at least 90% identical to the amino acid sequence set forth in SEQ ID NO: 45, a VH-FR2 amino acid sequence at least about 80%, about 90%, or about 95% identical to the amino acid sequence set forth in SEQ ID NO: 49, a VH-FR3 amino acid sequence at least about 80%, about 90%, or about 95% identical to the amino acid sequence set forth in SEQ ID NO:

50, a VH-FR4 amino acid sequence at least about 80%, about 90%, or about 95% identical to the amino acid sequence set forth in SEQ ID NO: 54, a VL-FR1 amino acid sequence at least about 80%, 90%, or 95% identical to the amino acid sequence set forth in SEQ ID NO: 57, a VL-FR2 amino acid sequence at least 80%, 90%, or 95% identical to the amino acid sequence set forth in SEQ ID NO: 61, a VL-FR3 amino acid sequence at least 80%, 90%, or 95% identical to the amino acid sequence set forth in SEQ ID NO: 65, and a VL-FR4 amino acid sequence at least 80%, about 90%, or about 95% identical to the amino acid sequence set forth in SEQ ID NO: 68. In certain embodiments, the antibody that specifically binds LIF comprises one or more human heavy chain framework regions comprising: a VH-FR1 amino acid sequence identical to the amino acid sequence set forth in any one of SEQ ID NOs: 44-47, a VH-FR2 amino acid sequence identical to the amino acid sequence set forth in any one of SEQ ID NOs: 48-49, a VH-FR3 amino acid sequence identical to the amino acid sequence set forth in any one of SEQ ID NOs: 50-52, or a VH-FR4 region amino acid sequence identical to the amino acid sequence set forth in any one of SEQ ID NOs: 53-55. In certain embodiments, the one or more human heavy chain framework regions comprise a VH-FR1 amino acid sequence identical to the amino acid sequence set forth in SEQ ID NO: 45, a VH-FR2 amino acid sequence identical to the amino acid sequence set forth in SEQ ID NO: 49, a VH-FR3 amino acid sequence identical to the amino acid sequence set forth in SEQ ID NO: 50, and a VH-FR4 amino acid sequence identical to the amino acid sequence set forth in SEQ ID NO: 54. In certain embodiments, the antibody that specifically binds LIF comprises one or more human light chain framework regions comprising: a VL-FR1 amino acid sequence identical to the amino acid sequence set forth in any one of SEQ ID NOs: 56-59, a VL-FR2 amino acid sequence identical to the amino acid sequence set forth in any one of SEQ ID NOs: 60-63, a VL-FR3 amino acid sequence identical to the amino acid sequence set forth in any one of SEQ ID NOs: 64-67, or a VL-FR4 amino acid sequence identical to the amino acid sequence set forth in any one of SEQ ID NOs: 68-70. In certain embodiments, the one or more human light chain framework regions comprise a VL-FR1 amino acid sequence identical to the amino acid sequence set forth in SEQ ID NO: 57, a VL-FR2 amino acid sequence identical to the amino acid sequence set forth in SEQ ID NO: 61, a VL-FR3 amino acid sequence identical to the amino acid sequence set forth in SEQ ID NO: 65, and a VL-FR4 amino acid sequence identical to the amino acid sequence set forth in SEQ ID NO: 68. In certain embodiments, the one or more human heavy chain framework regions and the one or more human light chain regions comprise a VH-FR1 amino acid sequence identical to the amino acid sequence set forth in SEQ ID NO: 45, a VH-FR2 amino acid sequence identical to the amino acid sequence set forth in SEQ ID NO: 49, a VH-FR3 amino acid sequence identical to the amino acid sequence set forth in SEQ ID NO: 50, a VH-FR4 amino acid sequence identical to the amino acid sequence set forth in SEQ ID NO: 54, a VL-FR1 amino acid sequence identical to the amino acid sequence set forth in SEQ ID NO: 57, a VL-FR2 amino acid sequence identical to the amino acid sequence set forth in SEQ ID NO: 61, a VL-FR3 amino acid sequence identical to the amino acid sequence set forth in SEQ ID NO: 65, and a VL-FR4 amino acid sequence identical to the amino acid sequence set forth in SEQ ID NO: 68. In certain embodiments, the antibody specifically binds human LIF.

5D8

The antibodies described herein were generated from rats and mice immunized with DNA encoding human LIF. One such antibody (5D8) was cloned and sequenced and comprises CDRs (using the combination of the Kabat and IMGT CDR numbering methods) with the following amino acid sequences: a VH-CDR1 corresponding to SEQ ID NO: 1 (GFTFSHAWMH), a VH-CDR2 corresponding to SEQ ID NO: 9 (QIKAKSDDYATYYAESVKG), a VH-CDR3 corresponding to SEQ ID NO: 15 (TCWEWDLDF), a VL-CDR1 corresponding to SEQ ID NO: 21 (RSSQSLLDS-DGHTYLN), a VL-CDR2 corresponding to SEQ ID NO: 25 (SVSNLES), and a VL-CDR3 corresponding to SEQ ID NO: 29 (MQATHAPPYT).

In certain embodiments, described herein, is an antibody that specifically binds LIF comprising a VH-CDR1 at least 80% or 90% identical to that set forth in SEQ ID NO: 1 (GFTFSHAWMH), a VH-CDR2 at least 80%, 90%, or 95% identical to that set forth in SEQ ID NO: 9 (QIKAKSD-DYATYYAESVKG), and a VH-CDR3 at least 80% or 90% identical to that set forth in SEQ ID NO: 15 (TCWEWDLDF). In certain embodiments, described herein, is an antibody that specifically binds LIF comprising a VL-CDR1 at least 80% or 90% identical to that set forth in SEQ ID NO: 21 (RSSQSLLDSDGHTYLN), a VL-CDR2 at least 80% identical to that set forth in SEQ ID NO: 25 (SVSNLES), and a VL-CDR3 at least 80% or 90% identical to that set forth in SEQ ID NO: 29 (MQATHAPPYT). In certain embodiments, described herein, is an antibody that specifically binds LIF comprising a VH-CDR1 set forth in SEQ ID NO: 1 (GFTFSHAWMH), a VH-CDR2 set forth in SEQ ID NO: 9 (QIKAKSDDYATYYAESVKG), a VH-CDR3 set forth in SEQ ID NO: 15 (TCWEWDLDF), a VL-CDR1 set forth in SEQ ID NO: 21 (RSSQSLLDS-DGHTYLN), a VL-CDR2 set forth in SEQ ID NO: 25 (SVSNLES), and a VL-CDR3 set forth in SEQ ID NO: 29 (MQATHAPPYT). Certain conservative amino acid substitutions are envisioned in the amino acid sequences of the CDRs of this disclosure. In certain embodiments, the antibody comprises CDRs that differ from the amino acid sequence set forth in any one of SEQ ID NOs: 1, 9, 15, 21, 25, and 29 by 1, 2, 3, or 4 amino acids. In certain embodiments, the antibody comprises CDRs that differ from the amino acid sequence set forth in any one of SEQ ID NOs: 1, 9, 15, 21, 25, and 29 by 1, 2, 3, or 4 amino acids and does not affect the binding affinity by greater than 10%, 20%, or 30%. In certain embodiments, antibodies that specifically bind LIF comprise one or more human heavy chain framework regions comprising: a VH-FR1 amino acid sequence at least about 80%, about 90%, or about 95% identical to the amino acid sequence set forth in any one of SEQ ID NOs: 44-47, a VH-FR2 amino acid sequence at least about 80%, about 90%, or about 95% identical to the amino acid sequence set forth in any one of SEQ ID NOs: 48-49, a VH-FR3 amino acid sequence at least 90% identical to the amino acid sequence set forth in any one of SEQ ID NOs: 50-52, or a VH-FR4 region amino acid sequence at least about 80%, about 90%, or about 95% identical to the amino acid sequence set forth in any one of SEQ ID NOs: 53-55. In certain embodiments, the one or more human heavy chain framework regions comprises a VH-FR1 amino acid sequence at least about 80%, about 90%, or about 95% identical to the amino acid sequence set forth in SEQ ID NO: 45, a VH-FR2 amino acid sequence at least about 80%, about 90%, or about 95% identical to the amino acid sequence set forth in SEQ ID NO: 49, a VH-FR3 amino acid sequence at least about 80%, about 90%, or about 95% identical to the amino acid sequence set forth in SEQ ID NO: 50, and a VH-FR4 amino acid sequence at least about 80%, about 90%, or about 95% identical to the amino acid sequence set forth in SEQ ID NO: 54. In certain embodiments, the antibody that specifically binds LIF comprises one or more human light chain framework regions comprising: a VL-FR1 amino acid sequence at least about 80%, about 90%, or about 95% identical to the amino acid sequence set forth in any one of SEQ ID NOs: 56-59, a VL-FR2 amino acid sequence at least about 80%, about 90%, or about 95% identical to the amino acid sequence set forth in any one of SEQ ID NOs: 60-63, a VL-FR3 amino acid sequence at least about 80%, about 90%, or about 95% identical to the amino acid sequence set forth in any one of SEQ ID NOs: 64-67, or a VL-FR4 amino acid sequence at least about 80%, about 90%, or about 95% identical to the amino acid sequence set forth in any one of SEQ ID NOs: 68-70. In certain embodiments, the one or more human light chain framework regions comprise a VL-FR1 amino acid sequence at least about 80%, about 90%, or about 95% identical to the amino acid sequence set forth in SEQ ID NO: 57, a VL-FR2 amino acid sequence at least about 80%, about 90%, or about 95% identical to the amino acid sequence set forth in SEQ ID NO: 61, a VL-FR3 amino acid sequence at least about 80%, about 90%, or about 95% identical to the amino acid sequence set forth in SEQ ID NO: 65, and a VL-FR4 amino acid sequence at least 90% identical to the amino acid sequence set forth in SEQ ID NO: 68. In certain embodiments, the one or more human heavy chain framework regions and the one or more human light chain regions comprise all of a VH-FR1 amino acid sequence at least about 80%, about 90%, or about 95% identical to the amino acid sequence set forth in SEQ ID NO: 45, a VH-FR2 amino acid sequence at least about 80%, about 90%, or about 95% identical to the amino acid sequence set forth in SEQ ID NO: 49, a VH-FR3 amino acid sequence at least about 80%, about 90%, or about 95% identical to the amino acid sequence set forth in SEQ ID NO: 50, a VH-FR4 amino acid sequence at least 90% identical to the amino acid sequence set forth in SEQ ID NO: 54, a VL-FR1 amino acid sequence at least about 80%, about 90%, or about 95% identical to the amino acid sequence set forth in SEQ ID NO: 57, a VL-FR2 amino acid sequence at least about 80%, about 90%, or about 95% identical to the amino acid sequence set forth in SEQ ID NO: 61, a VL-FR3 amino acid sequence at least about 80%, about 90%, or about 95% identical to the amino acid sequence set forth in SEQ ID NO: 65, and a VL-FR4 amino acid sequence at least about 80%, about 90%, or about 95% identical to the amino acid sequence set forth in SEQ ID NO: 68. In certain embodiments, the antibody specifically binds human LIF. In certain embodiments, the antibody that specifically binds LIF comprises one or more human heavy chain framework regions comprising: a VH-FR1 amino acid sequence identical to the amino acid sequence set forth in any one of SEQ ID NOs: 44-47, a VH-FR2 amino acid sequence identical to the amino acid sequence set forth in any one of SEQ ID NOs: 48-49, a VH-FR3 amino acid sequence identical to the amino acid sequence set forth in any one of SEQ ID NOs: 50-52, or a VH-FR4 region amino acid sequence identical to the amino acid sequence set forth in any one of SEQ ID NOs: 53-55. In certain embodiments, the one or more human heavy chain framework regions comprise a VH-FR1 amino acid sequence identical to the amino acid sequence set forth in SEQ ID NO: 45, a VH-FR2 amino acid sequence identical to the amino acid sequence set forth in SEQ ID NO: 49, a VH-FR3 amino acid sequence identical to the amino acid sequence set forth in SEQ ID NO: 50, and a VH-FR4 amino acid sequence identical to the amino acid sequence set forth in SEQ ID NO: 54. In certain embodiments, the antibody that specifically binds LIF comprises one or more human light chain framework regions comprising: a VL-FR1 amino acid sequence identical to the amino acid sequence set forth in any one of SEQ ID NOs: 56-59, a VL-FR2 amino acid sequence identical to the amino acid sequence set forth in any one of SEQ ID NOs: 60-63, a VL-FR3 amino acid sequence identical to the amino acid sequence set forth in any one of SEQ ID NOs: 64-67, or a VL-FR4 amino acid sequence identical to the amino acid sequence set forth in any one of SEQ ID NOs: 68-70. In certain embodiments, the one or more human light chain framework regions comprise a VL-FR1 amino acid sequence identical to the amino acid sequence set forth in SEQ ID NO: 57, a VL-FR2 amino acid sequence identical to the amino acid sequence set forth in SEQ ID NO: 61, a VL-FR3 amino acid sequence identical to the amino acid sequence set forth in SEQ ID NO: 65, and a VL-FR4 amino acid sequence identical to the amino acid sequence set forth in SEQ ID NO: 68. In certain embodiments, the one or more human heavy chain framework regions and the one or more human light chain regions comprise a VH-FR1 amino acid sequence identical to the amino acid sequence set forth in SEQ ID NO: 45, a VH-FR2 amino acid sequence identical to the amino acid sequence set forth in SEQ ID NO: 49, a VH-FR3 amino acid sequence identical to the amino acid sequence set forth in SEQ ID NO: 50, a VH-FR4 amino acid sequence identical to the amino acid sequence set forth in SEQ ID NO: 54, a VL-FR1 amino acid sequence identical to the amino acid sequence set forth in SEQ ID NO: 57, a VL-FR2 amino acid sequence identical to the amino acid sequence set forth in SEQ ID NO: 61, a VL-FR3 amino acid sequence identical to the amino acid sequence set forth in SEQ ID NO: 65, and a VL-FR4 amino acid sequence identical to the amino acid sequence set forth in SEQ ID NO: 68. In certain embodiments, the antibody specifically binds human LIF.

In certain embodiments, described herein, is an antibody that specifically binds LIF comprising a VH-CDR1 amino acid sequence at least 80% or 90% identical to that set forth in SEQ ID NO: 1 (GFTFSHAWMH), a VH-CDR2 amino acid sequence at least 80%, 90%, or 95% identical to that set forth in SEQ ID NO: 9 (QIKAKSDDYATYYAESVKG), and a VH-CDR3 amino acid sequence at least 80% or 90% identical to that set forth in SEQ ID NO: 95 (TSWEWDLDF). In certain embodiments, described herein, is an antibody that specifically binds LIF comprising a VL-CDR1 amino acid sequence at least 80% or 90% identical to that set forth in SEQ ID NO: 21 (RSSQSLLDSDGHTYLN), a VL-CDR2 amino acid sequence at least 80% identical to that set forth in SEQ ID NO: 25 (SVSNLES), and a VL-CDR3 amino acid sequence at least 80% or 90% identical to that set forth in SEQ ID NO: 29 (MQATHAPPYT). In certain embodiments, described herein, is an antibody that specifically binds LIF comprising a VH-CDR1 amino acid sequence set forth in SEQ ID NO: 1 (GFTFSHAWMH), a VH-CDR2 amino acid sequence set forth in SEQ ID NO: 9 (QIKAKSDDYATYYAESVKG), a VH-CDR3 amino acid sequence set forth in SEQ ID NO: 95 (TSWEWDLDF), a VL-CDR1 amino acid sequence set forth in SEQ ID NO: 21 (RSSQSLLDSDGHTYLN), a VL-CDR2 amino acid sequence set forth in SEQ ID NO: 25 (SVSNLES), and a VL-CDR3 amino acid sequence set forth in SEQ ID NO: 29 (MQATHAPPYT). Certain conservative amino acid substitutions are envisioned in the amino acid sequences of the CDRs of this disclosure. In certain embodiments, the antibody comprises CDRs that differ from the amino acid sequence set forth in any one of SEQ ID NOs: 1, 9, 95, 21, 25, and 29 by 1, 2, 3, or 4 amino acids. In certain embodiments, the antibody comprises CDRs that differ from the amino acid sequence set forth in any one of SEQ ID NOs: 1, 9, 95, 21, 25, and 29 by 1, 2, 3, or 4 amino acids and does not affect the binding affinity by greater than 10%, 20%, or 30%. In certain embodiments, antibodies that specifically bind LIF comprise one or more human heavy chain framework regions comprising: a VH-FR1 amino acid sequence at least about 80%, about 90%, or about 95% identical to the amino acid sequence set forth in any one of SEQ ID NOs: 44-47, a VH-FR2 amino acid sequence at least about 80%, about 90%, or about 95% identical to the amino acid sequence set forth in any one of SEQ ID NOs: 48-49, a VH-FR3 amino acid sequence at least 90% identical to the amino acid sequence set forth in any one of SEQ ID NOs: 50-52, or a VH-FR4 region amino acid sequence at least about 80%, about 90%, or about 95% identical to the amino acid sequence set forth in any one of SEQ ID NOs: 53-55. In certain embodiments, the one or more human heavy chain framework regions comprises a VH-FR1 amino acid sequence at least about 80%, about 90%, or about 95% identical to the amino acid sequence set forth in SEQ ID NO: 45, a VH-FR2 amino acid sequence at least about 80%, about 90%, or about 95% identical to the amino acid sequence set forth in SEQ ID NO: 49, a VH-FR3 amino acid sequence at least about 80%, about 90%, or about 95% identical to the amino acid sequence set forth in SEQ ID NO: 50, and a VH-FR4 amino acid sequence at least about 80%, about 90%, or about 95% identical to the amino acid sequence set forth in SEQ ID NO: 54. In certain embodiments, the antibody that specifically binds LIF comprises one or more human light chain framework regions comprising: a VL-FR1 amino acid sequence at least about 80%, about 90%, or about 95% identical to the amino acid sequence set forth in any one of SEQ ID NOs: 56-59, a VL-FR2 amino acid sequence at least about 80%, about 90%, or about 95% identical to the amino acid sequence set forth in any one of SEQ ID NOs: 60-63, a VL-FR3 amino acid sequence at least about 80%, about 90%, or about 95% identical to the amino acid sequence set forth in any one of SEQ ID NOs: 64-67, or a VL-FR4 amino acid sequence at least about 80%, about 90%, or about 95% identical to the amino acid sequence set forth in any one of SEQ ID NOs: 68-70. In certain embodiments, the one or more human light chain framework regions comprise a VL-FR1 amino acid sequence at least about 80%, about 90%, or about 95% identical to the amino acid sequence set forth in SEQ ID NO: 57, a VL-FR2 amino acid sequence at least about 80%, about 90%, or about 95% identical to the amino acid sequence set forth in SEQ ID NO: 61, a VL-FR3 amino acid sequence at least about 80%, about 90%, or about 95% identical to the amino acid sequence set forth in SEQ ID NO: 65, and a VL-FR4 amino acid sequence at least 90% identical to the amino acid sequence set forth in SEQ ID NO: 68. In certain embodiments, the one or more human heavy chain framework regions and the one or more human light chain regions comprise all of a VH-FR1 amino acid sequence at least about 80%, about 90%, or about 95% identical to the amino acid sequence set forth in SEQ ID NO: 45, a VH-FR2 amino acid sequence at least about 80%, about 90%, or about 95% identical to the amino acid sequence set forth in SEQ ID NO: 49, a VH-FR3 amino acid sequence at least about 80%, about 90%, or about 95% identical to the amino acid sequence set forth in SEQ ID NO: 50, a VH-FR4 amino acid sequence at least 90% identical to the amino acid sequence set forth in SEQ ID NO: 54, a VL-FR1 amino acid sequence at least about 80%, about 90%, or about 95% identical to the amino acid sequence set forth in SEQ ID NO: 57, a VL-FR2 amino acid sequence at least about 80%, about 90%, or about 95% identical to the amino acid sequence set forth in SEQ ID NO: 61, a VL-FR3 amino acid sequence at least about 80%, about 90%, or about 95% identical to the amino acid sequence set forth in SEQ ID NO: 65, and a VL-FR4 amino acid sequence at least about 80%, about 90%, or about 95% identical to the amino acid sequence set forth in SEQ ID NO: 68. In certain embodiments, the antibody specifically binds human LIF. In certain embodiments, the antibody that specifically binds LIF comprises one or more human heavy chain framework regions comprising: a VH-FR1 amino acid sequence identical to the amino acid sequence set forth in any one of SEQ ID NOs: 44-47, a VH-FR2 amino acid sequence identical to the amino acid sequence set forth in any one of SEQ ID NOs: 48-49, a VH-FR3 amino acid sequence identical to the amino acid sequence set forth in any one of SEQ ID NOs: 50-52, or a VH-FR4 region amino acid sequence identical to the amino acid sequence set forth in any one of SEQ ID NOs: 53-55. In certain embodiments, the one or more human heavy chain framework regions comprise a VH-FR1 amino acid sequence identical to the amino acid sequence set forth in SEQ ID NO: 45, a VH-FR2 amino acid sequence identical to the amino acid sequence set forth in SEQ ID NO: 49, a VH-FR3 amino acid sequence identical to the amino acid sequence set forth in SEQ ID NO: 50, and a VH-FR4 amino acid sequence identical to the amino acid sequence set forth in SEQ ID NO: 54. In certain embodiments, the antibody that specifically binds LIF comprises one or more human light chain framework regions comprising: a VL-FR1 amino acid sequence identical to the amino acid sequence set forth in any one of SEQ ID NOs: 56-59, a VL-FR2 amino acid sequence identical to the amino acid sequence set forth in any one of SEQ ID NOs: 60-63, a VL-FR3 amino acid sequence identical to the amino acid sequence set forth in any one of SEQ ID NOs: 64-67, or a VL-FR4 amino acid sequence identical to the amino acid sequence set forth in any one of SEQ ID NOs: 68-70. In certain embodiments, the one or more human light chain framework regions comprise a VL-FR1 amino acid sequence identical to the amino acid sequence set forth in SEQ ID NO: 57, a VL-FR2 amino acid sequence identical to the amino acid sequence set forth in SEQ ID NO: 61, a VL-FR3 amino acid sequence identical to the amino acid sequence set forth in SEQ ID NO: 65, and a VL-FR4 amino acid sequence identical to the amino acid sequence set forth in SEQ ID NO: 68. In certain embodiments, the one or more human heavy chain framework regions and the one or more human light chain regions comprise a VH-FR1 amino acid sequence identical to the amino acid sequence set forth in SEQ ID NO: 45, a VH-FR2 amino acid sequence identical to the amino acid sequence set forth in SEQ ID NO: 49, a VH-FR3 amino acid sequence identical to the amino acid sequence set forth in SEQ ID NO: 50, a VH-FR4 amino acid sequence identical to the amino acid sequence set forth in SEQ ID NO: 54, a VL-FR1 amino acid sequence identical to the amino acid sequence set forth in SEQ ID NO: 57, a VL-FR2 amino acid sequence identical to the amino acid sequence set forth in SEQ ID NO: 61, a VL-FR3 amino acid sequence identical to the amino acid sequence set forth in SEQ ID NO: 65, and a VL-FR4 amino acid sequence identical to the amino acid sequence set forth in SEQ ID NO: 68. In certain embodiments, the antibody specifically binds human LIF.

In certain embodiments, described herein, is an antibody that specifically binds LIF comprising a humanized heavy chain variable region comprising an amino acid sequence at least about 80%, about 90%, about 95%, about 97%, about 98%, or about 99% identical to the amino acid sequence set forth in any one of SEQ ID NOs: 71, 72, and 74. In certain embodiments, described herein, is an antibody that specifically binds LIF comprising a humanized heavy chain variable region comprising an amino acid sequence set forth in any one of SEQ ID NOs: 71, 72, and 74. In certain embodiments, described herein, is an antibody that specifically binds LIF comprising a humanized light chain variable region comprising an amino acid sequence at least about 80%, about 90%, about 95%, about 97%, about 98%, or about 99% identical to the amino acid sequence set forth in any one of SEQ ID NOs: 75-78. In certain embodiments, described herein, is an antibody that specifically binds LIF comprising a humanized light chain variable region comprising an amino acid sequence set forth in any one of SEQ ID NOs: 75-78. In certain embodiments, the antibody specifically binds human LIF.

In certain embodiments, described herein, is an antibody that specifically binds LIF comprising a humanized heavy chain variable region comprising an amino acid sequence at least about 80%, about 90%, about 95%, about 97%, about 98%, or about 99% identical to the amino acid sequence set forth in SEQ ID NO:72; and a humanized light chain variable region comprising an amino acid sequence at least about 80%, about 90%, about 95%, about 97%, about 98%, or about 99% identical to the amino acid sequence set forth in SEQ ID NO: 76. In certain embodiments, described herein, is an antibody that specifically binds LIF comprising a humanized heavy chain variable region comprising an amino acid sequence set forth in SEQ ID NO: 72; and a humanized light chain variable region comprising an amino acid sequence set forth in SEQ ID NO: 76.

In certain embodiments, described herein, is an antibody that specifically binds LIF comprising a humanized heavy chain variable region comprising an amino acid sequence at least about 80%, about 90%, about 95%, about 97%, about 98%, or about 99% identical to the amino acid sequence set forth in SEQ ID NO: 96; and a humanized light chain variable region comprising an amino acid sequence at least about 80%, about 90%, about 95%, about 97%, about 98%, or about 99% identical to the amino acid sequence set forth in SEQ ID NO: 76. In certain embodiments, described herein, is an antibody that specifically binds LIF comprising a humanized heavy chain variable region comprising an amino acid sequence set forth in SEQ ID NO: 96; and a humanized light chain variable region comprising an amino acid sequence set forth in SEQ ID NO: 76.

In certain embodiments, described herein, is an antibody that specifically binds LIF comprising a humanized heavy chain comprising an amino acid sequence at least about 80%, about 90%, about 95%, about 97%, about 98%, or about 99% identical to the amino acid sequence set forth in any one of SEQ ID NOs:79-82; and a humanized light chain comprising an amino acid sequence at least about 80%, about 90%, about 95%, about 97%, about 98%, or about 99% identical to the amino acid sequence set forth in any one of SEQ ID NOs: 83-86. In certain embodiments, described herein, is an antibody that specifically binds LIF comprising a humanized heavy chain comprising an amino acid sequence set forth in any one of SEQ ID NOs: 79-82; and a humanized light chain comprising an amino acid sequence set forth in any one of SEQ ID NOs: 83-86. In certain embodiments, described herein, is an antibody that specifically binds LIF comprising a humanized heavy chain comprising an amino acid sequence at least about 80%, about 90%, about 95%, about 97%, about 98%, or about 99% identical to the amino acid sequence set forth in any one of SEQ ID NOs:87-90; and a humanized light chain comprising an amino acid sequence at least about 80%, about 90%, about 95%, about 97%, about 98%, or about 99% identical to the amino acid sequence set forth in any one of SEQ ID NOs: 91-94. In certain embodiments, described herein, is an antibody that specifically binds LIF comprising a humanized heavy chain comprising an amino acid sequence set forth in any one of SEQ ID NOs: 87-90; and a humanized light chain comprising an amino acid sequence set forth in any one of SEQ ID NOs: 91-94.

In certain embodiments, described herein, is an antibody that specifically binds LIF comprising a humanized heavy chain comprising an amino acid sequence at least about 80%, about 90%, about 95%, about 97%, about 98%, or about 99% identical to the amino acid sequence set forth in SEQ ID NO:80; and a humanized light chain comprising an amino acid sequence at least about 80%, about 90%, about 95%, about 97%, about 98%, or about 99% identical to the amino acid sequence set forth in SEQ ID NO: 84. In certain embodiments, described herein, is an antibody that specifically binds LIF comprising a humanized heavy chain comprising an amino acid sequence set forth in SEQ ID NO: 80; and a humanized light chain comprising an amino acid sequence set forth in SEQ ID NO: 84. In certain embodiments, described herein, is an antibody that specifically binds LIF comprising a humanized heavy chain comprising an amino acid sequence at least about 80%, about 90%, about 95%, about 97%, about 98%, or about 99% identical to the amino acid sequence set forth in SEQ ID NO:88; and a humanized light chain comprising an amino acid sequence at least about 80%, about 90%, about 95%, about 97%, about 98%, or about 99% identical to the amino acid sequence set forth in SEQ ID NO: 92. In certain embodiments, described herein, is an antibody that specifically binds LIF comprising a humanized heavy chain comprising an amino acid sequence set forth in SEQ ID NO: 88; and a humanized light chain comprising an amino acid sequence set forth in SEQ ID NO: 92. In certain embodiments, described herein, is an antibody that specifically binds LIF comprising a humanized heavy chain comprising an amino acid sequence at least about 80%, about 90%, about 95%, about 97%, about 98%, or about 99% identical to the amino acid sequence set forth in SEQ ID NO:88; and a humanized light chain comprising an amino acid sequence at least about 80%, about 90%, about 95%, about 97%, about 98%, or about 99% identical to the amino acid sequence set forth in SEQ ID NO: 97. In certain embodiments, described herein, is an antibody that specifically binds LIF comprising a humanized heavy chain comprising an amino acid sequence set forth in SEQ ID NO: 88; and a humanized light chain comprising an amino acid sequence set forth in SEQ ID NO: 97.

In a certain embodiments, described herein, is a recombinant antibody that specifically binds Leukemia Inhibitory Factor (LIF) comprising: a heavy chain complementarity determining region 1 (VH-CDR1) comprising an amino acid sequence set forth in SEQ ID NO: 2; a heavy chain complementarity determining region 2 (VH-CDR2) comprising an amino acid sequence set forth in SEQ ID NO: 10; a heavy chain complementarity determining region 3 (VH-CDR3) comprising an amino acid sequence set forth in SEQ ID NO: 15; a light chain complementarity determining region 1 (VL-CDR1) comprising an amino acid sequence set forth in SEQ ID NO: 22; and a light chain complementarity determining region 2 (VL-CDR2) comprising an amino acid sequence set forth in SEQ ID NO: 26; and a light chain complementarity determining region 3 (VL-CDR3) comprising an amino acid sequence set forth in SEQ ID NO: 29.

In a certain embodiments, described herein, is a recombinant antibody that specifically binds Leukemia Inhibitory Factor (LIF) comprising: a heavy chain complementarity determining region 1 (VH-CDR1) comprising an amino acid sequence set forth in SEQ ID NO: 3; a heavy chain complementarity determining region 2 (VH-CDR2) comprising an amino acid sequence set forth in SEQ ID NO: 9; a heavy chain complementarity determining region 3 (VH-CDR3) comprising an amino acid sequence set forth in SEQ ID NO: 16; a light chain complementarity determining region 1 (VL-CDR1) comprising an amino acid sequence set forth in SEQ ID NO: 21; and a light chain complementarity determining region 2 (VL-CDR2) comprising an amino acid sequence set forth in SEQ ID NO: 25; and a light chain complementarity determining region 3 (VL-CDR3) comprising an amino acid sequence set forth in SEQ ID NO: 29.

In a certain embodiments, described herein, is a recombinant antibody that specifically binds Leukemia Inhibitory Factor (LIF) comprising: a heavy chain complementarity determining region 1 (VH-CDR1) comprising an amino acid sequence set forth in SEQ ID NO: 3; a heavy chain complementarity determining region 2 (VH-CDR2) comprising an amino acid sequence set forth in SEQ ID NO: 10; a heavy chain complementarity determining region 3 (VH-CDR3) comprising an amino acid sequence set forth in SEQ ID NO: 16; a light chain complementarity determining region 1 (VL-CDR1) comprising an amino acid sequence set forth in SEQ ID NO: 22; and a light chain complementarity determining region 2 (VL-CDR2) comprising an amino acid sequence set forth in SEQ ID NO: 26; and a light chain complementarity determining region 3 (VL-CDR3) comprising an amino acid sequence set forth in SEQ ID NO: 29.

10 G7

Another antibody cloned and sequenced from a rat immunization (10 G7) comprises CDRs (using the combination of the Kabat and IMGT CDR numbering methods) with the following amino acid sequences: a VH-CDR1 corresponding to SEQ ID NO: 4 (GFTFSNAWMH), a VH-CDR2 corresponding to SEQ ID NO: 11 (QIKDKSDNYATYYAESVKG), a VH-CDR3 corresponding to SEQ ID NO: 17 (TCWEWYLDF), a VL-CDR1 corresponding to SEQ ID NO: 21 (RSSQSLLDSDGHTYLN), a VL-CDR2 corresponding to SEQ ID NO: 25 (SVSNLES), and a VL-CDR3 corresponding to SEQ ID NO: 29 (MQATHAPPYT).

In certain embodiments, described herein, is an antibody that specifically binds LIF comprising a VH-CDR1 comprising an amino acid sequence at least 80% or 90% identical to that set forth in SEQ ID NO: 4 (GFTFSNAWMH), a VH-CDR2 comprising an amino acid sequence at least 80%, 90%, or 95% identical to that set forth in SEQ ID NO: 11 (QIKDKSDNYATYYAESVKG), and a VH-CDR3 comprising an amino acid sequence at least 80% or 90% identical to that set forth in SEQ ID NO: 17 (TCWEWYLDF). In certain embodiments, described herein, is an antibody that specifically binds LIF comprising a VL-CDR1 comprising an amino acid sequence at least 80% or 90% identical to that set forth in SEQ ID NO: 21 (RSSQSLLDSDGHTYLN), a VL-CDR2 comprising an amino acid sequence at least 80% identical to that set forth in SEQ ID NO: 25 (SVSNLES), and a VL-CDR3 comprising an amino acid sequence at least 80% or 90% identical to that set forth in SEQ ID NO: 29 (MQATHAPPYT). In certain embodiments, described herein, is an antibody that specifically binds LIF comprising a VH-CDR1 comprising an amino acid sequence set forth in SEQ ID NO: 4 (GFTFSNAWMH), a VH-CDR2 comprising an amino acid sequence set forth in SEQ ID NO: 11 (QIKDKSDNYATYYAESVKG), a VH-CDR3 comprising an amino acid sequence set forth in SEQ ID NO: 17 (TCWEWYLDF), a VL-CDR1 comprising an amino acid sequence set forth in SEQ ID NO: 21 (RSSQSLLDSDGHTYLN), a VL-CDR2 comprising an amino acid sequence set forth in SEQ ID NO: 25 (SVSNLES), and a VL-CDR3 comprising an amino acid sequence set forth in SEQ ID NO: 29 (MQATHAPPYT). Certain conservative amino acid substitutions are envisioned in the amino acid sequences of the CDRs of this disclosure. In certain embodiments, the antibody comprises CDR amino acid sequences that differ from the amino acid sequence set forth in any one of SEQ ID NOs: 4, 11, 17, 21, 25, and 29 by 1, 2, 3, or 4 amino acids. In certain embodiments, the antibody comprises CDR amino acid sequence s that differ from the amino acid sequence set forth in any one of SEQ ID NOs: 4, 11, 17, 21, 25, and 29 by 1, 2, 3, or 4 amino acids and does not affect the binding affinity by greater than 10%, 20%, or 30%. In certain embodiments, the antibodies that specifically bind LIF comprises one or more human heavy chain framework regions comprising: a VH-FR1 amino acid sequence at least about 80%, about 90%, or about 95% identical to the amino acid sequence set forth in any one of SEQ ID NOs: 44-47, a VH-FR2 amino acid sequence at least about 80%, about 90%, or about 95% identical to the amino acid sequence set forth in any one of SEQ ID NOs: 48-49, a VH-FR3 amino acid sequence at least about 80%, about 90%, or about 95% identical to the amino acid sequence set forth in any one of SEQ ID NOs: 50-52, or a VH-FR4 region amino acid sequence at least about 80%, about 90%, or about 95% identical to the amino acid sequence set forth in any one of SEQ ID NOs: 53-55. In certain embodiments, the one or more human heavy chain framework regions comprise a VH-FR1 amino acid sequence at least about 80%, about 90%, or about 95% identical to the amino acid sequence set forth in SEQ ID NO: 45, a VH-FR2 amino acid sequence at least about 80%, about 90%, or about 95% identical to the amino acid sequence set forth in SEQ ID NO: 49, a VH-FR3 amino acid sequence at least about 80%, about 90%, or about 95% identical to the amino acid sequence set forth in SEQ ID NO: 50, and a VH-FR4 amino acid sequence at least about 80%, about 90%, or about 95% identical to the amino acid sequence set forth in SEQ ID NO: 54. In certain embodiments, the antibodies that specifically bind LIF comprise one or more human light chain framework regions comprising: a VL-FR1 amino acid sequence at least about 80%, about 90%, or about 95% identical to the amino acid sequence set forth in any one of SEQ ID NOs: 56-59, a VL-FR2 amino acid sequence at least about 80%, about 90%, or about 95% identical to the amino acid sequence set forth in any one of SEQ ID NOs: 60-63, a VL-FR3 amino acid sequence at least about 80%, about 90%, or about 95% identical to the amino acid sequence set forth in any one of SEQ ID NOs: 64-67, or a VL-FR4 amino acid sequence at least about 80%, about 90%, or about 95% identical to the amino acid sequence set forth in any one of SEQ ID NOs: 68-70. In certain embodiments, the one or more human light chain framework regions comprise a VL-FR1 amino acid sequence at least about 80%, about 90%, or about 95% identical to the amino acid sequence set forth in SEQ ID NO: 57, a VL-FR2 amino acid sequence at least about 80%, about 90%, or about 95% identical to the amino acid sequence set forth in SEQ ID NO: 61, a VL-FR3 amino acid sequence at least about 80%, about 90%, or about 95% identical to the amino acid sequence set forth in SEQ ID NO: 65, and a VL-FR4 amino acid sequence at least about 80%, about 90%, or about 95% identical to the amino acid sequence set forth in SEQ ID NO: 68. In certain embodiments, the one or more human heavy chain framework regions and the one or more human light chain regions comprise all of a VH-FR1 amino acid sequence at least about 80%, about 90%, or about 95% identical to the amino acid sequence set forth in SEQ ID NO: 45, a VH-FR2 amino acid sequence at least about 80%, about 90%, or about 95% identical to the amino acid sequence set forth in SEQ ID NO: 49, a VH-FR3 amino acid sequence at least about 80%, about 90%, or about 95% identical to the amino acid sequence set forth in SEQ ID NO: 50, a VH-FR4 amino acid sequence at least about 80%, about 90%, or about 95% identical to the amino acid sequence set forth in SEQ ID NO: 54, a VL-FR1 amino acid sequence at least about 80%, about 90%, or about 95% identical to the amino acid sequence set forth in SEQ ID NO: 57, a VL-FR2 amino acid sequence at least about 80%, about 90%, or about 95% identical to the amino acid sequence set forth in SEQ ID NO: 61, a VL-FR3 amino acid sequence at least about 80%, about 90%, or about 95% identical to the amino acid sequence set forth in SEQ ID NO: 65, and a VL-FR4 amino acid sequence at least about 80%, about 90%, or about 95% identical to the amino acid sequence set forth in SEQ ID NO: 68. In certain embodiments, the antibody specifically binds human LIF. In certain embodiments, the antibody that specifically binds LIF comprises one or more human heavy chain framework regions comprising: a VH-FR1 amino acid sequence identical to the amino acid sequence set forth in any one of SEQ ID NOs: 44-47, a VH-FR2 amino acid sequence identical to the amino acid sequence set forth in any one of SEQ ID NOs: 48-49, a VH-FR3 amino acid sequence identical to the amino acid sequence set forth in any one of SEQ ID NOs: 50-52, or a VH-FR4 region amino acid sequence identical to the amino acid sequence set forth in any one of SEQ ID NOs: 53-55. In certain embodiments, the one or more human heavy chain framework regions comprise a VH-FR1 amino acid sequence identical to the amino acid sequence set forth in SEQ ID NO: 45, a VH-FR2 amino acid sequence identical to the amino acid sequence set forth in SEQ ID NO: 49, a VH-FR3 amino acid sequence identical to the amino acid sequence set forth in SEQ ID NO: 50, and a VH-FR4 amino acid sequence identical to the amino acid sequence set forth in SEQ ID NO: 54. In certain embodiments, the antibody that specifically binds LIF comprises one or more human light chain framework regions comprising: a VL-FR1 amino acid sequence identical to the amino acid sequence set forth in any one of SEQ ID NOs: 56-59, a VL-FR2 amino acid sequence identical to the amino acid sequence set forth in any one of SEQ ID NOs: 60-63, a VL-FR3 amino acid sequence identical to the amino acid sequence set forth in any one of SEQ ID NOs: 64-67, or a VL-FR4 amino acid sequence identical to the amino acid sequence set forth in any one of SEQ ID NOs: 68-70. In certain embodiments, the one or more human light chain framework regions comprise a VL-FR1 amino acid sequence identical to the amino acid sequence set forth in SEQ ID NO: 57, a VL-FR2 amino acid sequence identical to the amino acid sequence set forth in SEQ ID NO: 61, a VL-FR3 amino acid sequence identical to the amino acid sequence set forth in SEQ ID NO: 65, and a VL-FR4 amino acid sequence identical to the amino acid sequence set forth in SEQ ID NO: 68. In certain embodiments, the one or more human heavy chain framework regions and the one or more human light chain regions comprise a VH-FR1 amino acid sequence identical to the amino acid sequence set forth in SEQ ID NO: 45, a VH-FR2 amino acid sequence identical to the amino acid sequence set forth in SEQ ID NO: 49, a VH-FR3 amino acid sequence identical to the amino acid sequence set forth in SEQ ID NO: 50, a VH-FR4 amino acid sequence identical to the amino acid sequence set forth in SEQ ID NO: 54, a VL-FR1 amino acid sequence identical to the amino acid sequence set forth in SEQ ID NO: 57, a VL-FR2 amino acid sequence identical to the amino acid sequence set forth in SEQ ID NO: 61, a VL-FR3 amino acid sequence identical to the amino acid sequence set forth in SEQ ID NO: 65, and a VL-FR4 amino acid sequence identical to the amino acid sequence set forth in SEQ ID NO: 68. In certain embodiments, the antibody specifically binds human LIF.

6B5

Another antibody cloned and sequenced from a rat immunization (6B5) comprises CDRs (using the Kabat numbering method) with the following amino acid sequences: a VH-CDR1 corresponding to SEQ ID NO: 7 (SKFMY), a VH-CDR2 corresponding to SEQ ID NO: 13 (WIYPGDGDTEYNQKFSE), a VH-CDR3 corresponding to SEQ ID NO: 19 (RDYHSSHFAY), a VL-CDR1 corresponding to SEQ ID NO: 23 (RSSQSLLHNNGNTYLS), a VL-CDR2 corresponding to SEQ ID NO: 27 (QVSNRFS), and a VL-CDR3 corresponding to SEQ ID NO: 30 (GQGTQYPYT).

In certain embodiments, described herein, is an antibody that specifically binds LIF comprising a VH-CDR1 amino acid sequence at least 80% identical to that set forth in SEQ ID NO: 7 (SKFMY), a VH-CDR2 amino acid sequence at least 80% or 90% identical to that set forth in SEQ ID NO: 13 (WIYPGDGDTEYNQKFSE), and a VH-CDR3 amino acid sequence at least 80% or 90% identical to that set forth in SEQ ID NO: 19 (RDYHSSHFAY). In certain embodiments, described herein, is an antibody that specifically binds LIF comprising a VL-CDR1 amino acid sequence at least 80% or 90% identical to that set forth in SEQ ID NO: 23 (RSSQSLLHNNGNTYLS), a VL-CDR2 amino acid sequence at least 80% identical to that set forth in SEQ ID NO: 27 (QVSNRFS), and a VL-CDR3 amino acid sequence at least 80% identical to that set forth in to SEQ ID NO: 30 (GQGTQYPYT). In certain embodiments, described herein, is an antibody that specifically binds LIF comprising a VH-CDR1 amino acid sequence set forth in SEQ ID NO: 7 (SKFMY), a VH-CDR2 amino acid sequence set forth SEQ ID NO: 13 (WIYPGDGDTEYNQKFSE), a VH-CDR3 amino acid sequence set forth in SEQ ID NO: 19 (RDYHSSHFAY), a VL-CDR1 amino acid sequence set forth in SEQ ID NO: 23 (RSSQSLLHNNGNTYLS), a VL-CDR2 amino acid sequence set forth in SEQ ID NO: 27 (QVSNRFS), and a VL-CDR3 amino acid sequence set forth in to SEQ ID NO: 30 (GQGTQYPYT). Certain conservative amino acid substitutions are envisioned in the amino acid sequences of the CDRs of this disclosure. In certain embodiments, the antibody comprises CDR amino acid sequences that differ from the amino acid sequence set forth in any one of SEQ ID NOs: 7, 13, 19, 23, 27, and 30 by 1, 2, 3, or 4 amino acids. In certain embodiments, the antibody comprises CDR amino acid sequences that differ from the amino acid sequence set forth in any one of SEQ ID NOs: 7, 13, 19, 23, 27, and 30 by 1, 2, 3, or 4 amino acids and does not affect the binding affinity by greater than 10%, 20%, or 30%. In certain embodiments, antibodies that specifically bind LIF comprise one or more human heavy chain framework regions comprising: a VH-FR1 amino acid sequence at least about 80%, about 90%, or about 95% identical to the amino acid sequence set forth in any one of SEQ ID NOs: 44-47, a VH-FR2 amino acid sequence at least about 80%, about 90%, or about 95% identical to the amino acid sequence set forth in any one of SEQ ID NOs: 48-49, a VH-FR3 amino acid sequence at least about 80%, about 90%, or about 95% identical to the amino acid sequence set forth in any one of SEQ ID NOs: 50-52, or a VH-FR4 region amino acid sequence at least about 80%, about 90%, or about 95% identical to the amino acid sequence set forth in any one of SEQ ID NOs: 53-55. In certain embodiments, the one or more human heavy chain framework regions comprises a VH-FR1 amino acid sequence at least about 80%, about 90%, or about 95% identical to the amino acid sequence set forth in SEQ ID NO: 45, a VH-FR2 amino acid sequence at least about 80%, about 90%, or about 95% identical to the amino acid sequence set forth in SEQ ID NO: 49, a VH-FR3 amino acid sequence at least about 80%, about 90%, or about 95% identical to the amino acid sequence set forth in SEQ ID NO: 50, and a VH-FR4 amino acid sequence at least about 80%, about 90%, or about 95% identical to the amino acid sequence set forth in SEQ ID NO: 54. In certain embodiments, antibodies that specifically bind LIF comprise one or more human light chain framework regions comprising: a VL-FR1 amino acid sequence at least about 80%, about 90%, or about 95% identical to the amino acid sequence set forth in any one of SEQ ID NOs: 56-59, a VL-FR2 amino acid sequence at least about 80%, about 90%, or about 95% identical to the amino acid sequence set forth in any one of SEQ ID NOs: 60-63, a VL-FR3 amino acid sequence at least about 80%, about 90%, or about 95% identical to the amino acid sequence set forth in any one of SEQ ID NOs: 64-67, or a VL-FR4 amino acid sequence at least about 80%, about 90%, or about 95% identical to the amino acid sequence set forth in any one of SEQ ID NOs: 68-70. In certain embodiments, the one or more human light chain framework regions comprise a VL-FR1 amino acid sequence at least about 80%, about 90%, or about 95% identical to the amino acid sequence set forth in SEQ ID NO: 57, a VL-FR2 amino acid sequence at least about 80%, about 90%, or about 95% identical to the amino acid sequence set forth in SEQ ID NO: 61, a VL-FR3 amino acid sequence at least about 80%, about 90%, or about 95% identical to the amino acid sequence set forth in SEQ ID NO: 65, and a VL-FR4 amino acid sequence at least about 80%, about 90%, or about 95% identical to the amino acid sequence set forth in SEQ ID NO: 68. In certain embodiments, the one or more human heavy chain framework regions and the one or more human light chain regions comprise all of a VH-FR1 amino acid sequence at least about 80%, about 90%, or about 95% identical to the amino acid sequence set forth in SEQ ID NO: 45, a VH-FR2 amino acid sequence at least about 80%, about 90%, or about 95% identical to the amino acid sequence set forth in SEQ ID NO: 49, a VH-FR3 amino acid sequence at least about 80%, about 90%, or about 95% identical to the amino acid sequence set forth in SEQ ID NO: 50, a VH-FR4 amino acid sequence at least about 80%, about 90%, or about 95% identical to the amino acid sequence set forth in SEQ ID NO: 54, a VL-FR1 amino acid sequence at least about 80%, about 90%, or about 95% identical to the amino acid sequence set forth in SEQ ID NO: 57, a VL-FR2 amino acid sequence at least about 80%, about 90%, or about 95% identical to the amino acid sequence set forth in SEQ ID NO: 61, a VL-FR3 amino acid sequence at least about 80%, about 90%, or about 95% identical to the amino acid sequence set forth in SEQ ID NO: 65, and a VL-FR4 amino acid sequence at least about 80%, about 90%, or about 95% identical to the amino acid sequence set forth in SEQ ID NO: 68. In certain embodiments, the antibody specifically binds human LIF. In certain embodiments, the antibody that specifically binds LIF comprises one or more human heavy chain framework regions comprising: a VH-FR1 amino acid sequence identical to the amino acid sequence set forth in any one of SEQ ID NOs: 44-47, a VH-FR2 amino acid sequence identical to the amino acid sequence set forth in any one of SEQ ID NOs: 48-49, a VH-FR3 amino acid sequence identical to the amino acid sequence set forth in any one of SEQ ID NOs: 50-52, or a VH-FR4 region amino acid sequence identical to the amino acid sequence set forth in any one of SEQ ID NOs: 53-55. In certain embodiments, the one or more human heavy chain framework regions comprise a VH-FR1 amino acid sequence identical to the amino acid sequence set forth in SEQ ID NO: 45, a VH-FR2 amino acid sequence identical to the amino acid sequence set forth in SEQ ID NO: 49, a VH-FR3 amino acid sequence identical to the amino acid sequence set forth in SEQ ID NO: 50, and a VH-FR4 amino acid sequence identical to the amino acid sequence set forth in SEQ ID NO: 54. In certain embodiments, the antibody that specifically binds LIF comprises one or more human light chain framework regions comprising: a VL-FR1 amino acid sequence identical to the amino acid sequence set forth in any one of SEQ ID NOs: 56-59, a VL-FR2 amino acid sequence identical to the amino acid sequence set forth in any one of SEQ ID NOs: 60-63, a VL-FR3 amino acid sequence identical to the amino acid sequence set forth in any one of SEQ ID NOs: 64-67, or a VL-FR4 amino acid sequence identical to the amino acid sequence set forth in any one of SEQ ID NOs: 68-70. In certain embodiments, the one or more human light chain framework regions comprise a VL-FR1 amino acid sequence identical to the amino acid sequence set forth in SEQ ID NO: 57, a VL-FR2 amino acid sequence identical to the amino acid sequence set forth in SEQ ID NO: 61, a VL-FR3 amino acid sequence identical to the amino acid sequence set forth in SEQ ID NO: 65, and a VL-FR4 amino acid sequence identical to the amino acid sequence set forth in SEQ ID NO: 68. In certain embodiments, the one or more human heavy chain framework regions and the one or more human light chain regions comprise a VH-FR1 amino acid sequence identical to the amino acid sequence set forth in SEQ ID NO: 45, a VH-FR2 amino acid sequence identical to the amino acid sequence set forth in SEQ ID NO: 49, a VH-FR3 amino acid sequence identical to the amino acid sequence set forth in SEQ ID NO: 50, a VH-FR4 amino acid sequence identical to the amino acid sequence set forth in SEQ ID NO: 54, a VL-FR1 amino acid sequence identical to the amino acid sequence set forth in SEQ ID NO: 57, a VL-FR2 amino acid sequence identical to the amino acid sequence set forth in SEQ ID NO: 61, a VL-FR3 amino acid sequence identical to the amino acid sequence set forth in SEQ ID NO: 65, and a VL-FR4 amino acid sequence identical to the amino acid sequence set forth in SEQ ID NO: 68. In certain embodiments, the antibody specifically binds human LIF.

9 G7

Another antibody cloned and sequenced from a mouse immunization (9 G7) comprises CDRs (using the Kabat numbering method) with the following amino acid sequences: a VH-CDR1 corresponding to SEQ ID NO: 33 (TAGMQ), a VH-CDR2 corresponding to SEQ ID NO: 35 (WINTQSGEPQYVDDFRG), a VH-CDR3 corresponding to SEQ ID NO: 37 (WALYSEYDVMDY), a VL-CDR1 corresponding to SEQ ID NO: 39 (KASENVDSYVS), a VL-CDR2 corresponding to SEQ ID NO: 41 (GASNRYT), and a VL-CDR3 corresponding to SEQ ID NO: 43 (GQSYRYPPT).

In certain embodiments, described herein, is an antibody that specifically binds LIF comprising a VH-CDR1 amino acid sequence at least 80% identical to that set forth in SEQ ID NO: 33 (TAGMQ), a VH-CDR2 amino acid sequence at least 80% or 90% identical to that set forth in SEQ ID NO: 35 (WINTQSGEPQYVDDFRG), and a VH-CDR3 amino acid sequence at least 80% or 90% identical to that set forth in SEQ ID NO: 37 (WALYSEYDVMDY). In certain embodiments, described herein, is an antibody that specifically binds LIF comprising a VL-CDR1 amino acid sequence at least 80% or 90% identical to that set forth in SEQ ID NO: 39 (KASENVDSYVS), a VL-CDR2 amino acid sequence at least 80% identical set forth in SEQ ID NO: 41 (GASNRYT), and a VL-CDR3 amino acid sequence at least 80% or 90% identical to that set forth in to SEQ ID NO: 43 (GQSYRYPPT). In certain embodiments, described herein, is an antibody that specifically binds LIF comprising a VH-CDR1 amino acid sequence set forth in SEQ ID NO: 33 (TAGMQ), a VH-CDR2 amino acid sequence set forth in SEQ ID NO: 35 (WINTQSGEPQYVDDFRG), a VH-CDR3 amino acid sequence set forth in SEQ ID NO: 37 (WALYSEYDVMDY), a VL-CDR1 amino acid sequence set forth in SEQ ID NO: 39 (KASENVDSYVS), a VL-CDR2 amino acid sequence set forth in SEQ ID NO: 41 (GASNRYT), and a VL-CDR3 amino acid sequence set forth in to SEQ ID NO: 43 (GQSYRYPPT). Certain conservative amino acid substitutions are envisioned in the amino acid sequences of the CDRs of this disclosure. In certain embodiments, the antibody comprises CDR amino acid sequences that differ from the amino acid sequence set forth in any one of SEQ ID NOs: 39, 41, 43, 33, 35, and 37 by 1, 2, 3, or 4 amino acids. In certain embodiments, the antibody comprises CDR amino acid sequences that differ from the amino acid sequence set forth in any one of SEQ ID NOs: 39, 41, 43, 33, 35, and 37 by 1, 2, 3, or 4 amino acids and does not affect the binding affinity by greater than 10%, 20%, or 30%. In certain embodiments, antibodies that specifically bind LIF comprise one or more human heavy chain framework regions comprising: a VH-FR1 amino acid sequence at least about 80%, about 90%, or about 95% identical to the amino acid sequence set forth in any one of SEQ ID NOs: 44-47, a VH-FR2 amino acid sequence at least about 80%, about 90%, or about 95% identical to the amino acid sequence set forth in any one of SEQ ID NOs: 48-49, a VH-FR3 amino acid sequence at least about 80%, about 90%, or about 95% identical to the amino acid sequence set forth in any one of SEQ ID NOs: 50-52, or a VH-FR4 region amino acid sequence at least about 80%, about 90%, or about 95% identical to the amino acid sequence set forth in any one of SEQ ID NOs: 53-55. In certain embodiments, the one or more human heavy chain framework regions comprise a VH-FR1 amino acid sequence at least about 80%, about 90%, or about 95% identical to the amino acid sequence set forth in SEQ ID NO: 45, a VH-FR2 amino acid sequence at least about 80%, about 90%, or about 95% identical to the amino acid sequence set forth in SEQ ID NO: 49, a VH-FR3 amino acid sequence at least about 80%, about 90%, or about 95% identical to the amino acid sequence set forth in SEQ ID NO: 50, and a VH-FR4 amino acid sequence at least about 80%, about 90%, or about 95% identical to the amino acid sequence set forth in SEQ ID NO: 54. In certain embodiments, antibodies that specifically bind LIF comprise one or more human light chain framework regions comprising: a VL-FR1 amino acid sequence at least about 80%, about 90%, or about 95% identical to the amino acid sequence set forth in any one of SEQ ID NOs: 56-59, a VL-FR2 amino acid sequence at least about 80%, about 90%, or about 95% identical to the amino acid sequence set forth in any one of SEQ ID NOs: 60-63, a VL-FR3 amino acid sequence at least about 80%, about 90%, or about 95% identical to the amino acid sequence set forth in any one of SEQ ID NOs: 64-67, or a VL-FR4 amino acid sequence at least about 80%, about 90%, or about 95% identical to the amino acid sequence set forth in any one of SEQ ID NOs: 68-70. In certain embodiments, the one or more human light chain framework regions comprise a VL-FR1 amino acid sequence at least about 80%, about 90%, or about 95% identical to the amino acid sequence set forth in SEQ ID NO: 57, a VL-FR2 amino acid sequence at least about 80%, about 90%, or about 95% identical to the amino acid sequence set forth in SEQ ID NO: 61, a VL-FR3 amino acid sequence at least about 80%, about 90%, or about 95% identical to the amino acid sequence set forth in SEQ ID NO: 65, and a VL-FR4 amino acid sequence at least about 80%, about 90%, or about 95% identical to the amino acid sequence set forth in SEQ ID NO: 68. In certain embodiments, the one or more human heavy chain framework regions and the one or more human light chain regions comprise all of a VH-FR1 amino acid sequence at least about 80%, about 90%, or about 95% identical to the amino acid sequence set forth in SEQ ID NO: 45, a VH-FR2 amino acid sequence at least about 80%, about 90%, or about 95% identical to the amino acid sequence set forth in SEQ ID NO: 49, a VH-FR3 amino acid sequence at least about 80%, about 90%, or about 95% identical to the amino acid sequence set forth in SEQ ID NO: 50, a VH-FR4 amino acid sequence at least about 80%, about 90%, or about 95% identical to the amino acid sequence set forth in SEQ ID NO: 54, a VL-FR1 amino acid sequence at least about 80%, about 90%, or about 95% identical to the amino acid sequence set forth in SEQ ID NO: 57, a VL-FR2 amino acid sequence at least about 80%, about 90%, or about 95% identical to the amino acid sequence set forth in SEQ ID NO: 61, a VL-FR3 amino acid sequence at least about 80%, about 90%, or about 95% identical to the amino acid sequence set forth in SEQ ID NO: 65, and a VL-FR4 amino acid sequence at least about 80%, about 90%, or about 95% identical to the amino acid sequence set forth in SEQ ID NO: 68. In certain embodiments, the antibody specifically binds human LIF. In certain embodiments, the antibody that specifically binds LIF comprises one or more human heavy chain framework regions comprising: a VH-FR1 amino acid sequence identical to the amino acid sequence set forth in any one of SEQ ID NOs: 44-47, a VH-FR2 amino acid sequence identical to the amino acid sequence set forth in any one of SEQ ID NOs: 48-49, a VH-FR3 amino acid sequence identical to the amino acid sequence set forth in any one of SEQ ID NOs: 50-52, or a VH-FR4 region amino acid sequence identical to the amino acid sequence set forth in any one of SEQ ID NOs: 53-55. In certain embodiments, the one or more human heavy chain framework regions comprise a VH-FR1 amino acid sequence identical to the amino acid sequence set forth in SEQ ID NO: 45, a VH-FR2 amino acid sequence identical to the amino acid sequence set forth in SEQ ID NO: 49, a VH-FR3 amino acid sequence identical to the amino acid sequence set forth in SEQ ID NO: 50, and a VH-FR4 amino acid sequence identical to the amino acid sequence set forth in SEQ ID NO: 54. In certain embodiments, the antibody that specifically binds LIF comprises one or more human light chain framework regions comprising: a VL-FR1 amino acid sequence identical to the amino acid sequence set forth in any one of SEQ ID NOs: 56-59, a VL-FR2 amino acid sequence identical to the amino acid sequence set forth in any one of SEQ ID NOs: 60-63, a VL-FR3 amino acid sequence identical to the amino acid sequence set forth in any one of SEQ ID NOs: 64-67, or a VL-FR4 amino acid sequence identical to the amino acid sequence set forth in any one of SEQ ID NOs: 68-70. In certain embodiments, the one or more human light chain framework regions comprise a VL-FR1 amino acid sequence identical to the amino acid sequence set forth in SEQ ID NO: 57, a VL-FR2 amino acid sequence identical to the amino acid sequence set forth in SEQ ID NO: 61, a VL-FR3 amino acid sequence identical to the amino acid sequence set forth in SEQ ID NO: 65, and a VL-FR4 amino acid sequence identical to the amino acid sequence set forth in SEQ ID NO: 68. In certain embodiments, the one or more human heavy chain framework regions and the one or more human light chain regions comprise a VH-FR1 amino acid sequence identical to the amino acid sequence set forth in SEQ ID NO: 45, a VH-FR2 amino acid sequence identical to the amino acid sequence set forth in SEQ ID NO: 49, a VH-FR3 amino acid sequence identical to the amino acid sequence set forth in SEQ ID NO: 50, a VH-FR4 amino acid sequence identical to the amino acid sequence set forth in SEQ ID NO: 54, a VL-FR1 amino acid sequence identical to the amino acid sequence set forth in SEQ ID NO: 57, a VL-FR2 amino acid sequence identical to the amino acid sequence set forth in SEQ ID NO: 61, a VL-FR3 amino acid sequence identical to the amino acid sequence set forth in SEQ ID NO: 65, and a VL-FR4 amino acid sequence identical to the amino acid sequence set forth in SEQ ID NO: 68. In certain embodiments, the antibody specifically binds human LIF.

The antibodies described herein directly bind human LIF. The canonical amino acid sequence of human LIF is given by SEQ ID NO: 98. Those of skill in the art will appreciate that natural variants of SEQ ID NO: 98 are possible amongst the human population that may lead to differences of 1, 2, 3, 4, or 5 amino acids between SEQ ID NO: 98 and LIF expressed by any given human individual. Small changes that arise due to natural variation are not expected to give rise to different binding kinetics or efficacy in treatment of any of the antibodies described herein.

Epitopes Bound by Therapeutically Useful LIF Antibodies

Described herein is a unique epitope of human LIF that when bound inhibits LIF biological activity (e.g., STAT3 phosphorylation) and inhibits tumor growth in vivo. The epitope described herein consists of two discontinuous stretches of amino acids (from residue 13 to residue 32 and from residue 120 to 138 of human LIF), that are present in two distinct topological domains (alpha helices A and C) of the human LIF protein. This binding is a combination of weak (Van der Waals attraction), medium (hydrogen binding), and strong (salt bridge) interactions. In certain embodiments, a contact residue is a residue on LIF that forms a hydrogen bond with a residue on an anti-LIF antibody. In certain embodiments, a contact residue is a residue on LIF that forms a salt bridge with a residue on an anti-LIF antibody. In certain embodiments, a contact residue is a residue on LIF that results in a Van der Waals attraction with and is within at least 5, 4, or 3 angstroms of a residue on an anti-LIF antibody.

In certain embodiments, described herein is an isolated antibody that binds any one, two, three, four, five, six, seven, eight, nine, ten, eleven, twelve, thirteen, fourteen, fifteen, sixteen, seventeen, eighteen, nineteen, or twenty of the following residues: A13, I14, R15, H16, P17, C18, H19, N20, Q25, Q29, Q32, D120, R123, S127, N128, L130, C131, C134, S135, or H138 of SEQ ID NO:98. In certain embodiments, described herein is an isolated antibody that binds all of the following residues: A13, I14, R15, H16, P17, C18, H19, N20, Q25, Q29, Q32, D120, R123, S127, N128, L130, C131, C134, S135, and H138 of SEQ ID NO:98. In certain embodiments, described herein is an isolated antibody that binds all of the following residues: A13, I14, R15, H16, P17, C18, H19, N20, Q25, Q29, Q32, D120, R123, S127, N128, L130, C131, C134, S135, and H138 of SEQ ID NO:98. In certain embodiments, the antibody only binds residues that participate with the antibody in strong or medium interactions. In certain embodiments, the antibody only binds residues that participate with the antibody in strong interactions. In a certain embodiment, the antibody interacts with helix A and C of LIF. In a certain embodiment, the antibody blocks LIF interaction with gp130.

In certain embodiments, described herein is an antibody comprising CDRs with an amino acid sequence set forth in any one of SEQ ID NOs: 1, 9, 15, 21, 25, and 29 that binds any one, two, three, four, five, six, seven, eight, nine, ten, eleven, twelve, thirteen, fourteen, fifteen, sixteen, seventeen, eighteen, nineteen, or twenty of the following residues: A13, I14, R15, H16, P17, C18, H19, N20, Q25, Q29, Q32, D120, R123, S127, N128, L130, C131, C134, S135, or H138 of SEQ ID NO:98. In certain embodiments, described herein is an antibody comprising CDRs with an amino acid sequence set forth in any one of SEQ ID NOs: 1, 9, 15, 21, 25, and 29 that binds to all of the following residues: A13, I14, R15, H16, P17, C18, H19, N20, Q25, Q29, Q32, D120, R123, S127, N128, L130, C131, C134, S135, and H138 of SEQ ID NO:98. In certain embodiments, the antibody only binds residues that participate with the antibody in strong or medium interactions. In certain embodiments, the antibody only binds residues that participate with the antibody in strong interactions.

In certain embodiments, described herein is an antibody comprising CDRs with an amino acid sequence set forth in any one of SEQ ID NOs: 1, 9, 95, 21, 25, and 29 that binds any one, two, three, four, five, six, seven, eight, nine, ten, eleven, twelve, thirteen, fourteen, fifteen, sixteen, seventeen, eighteen, nineteen, or twenty of the following residues: A13, I14, R15, H16, P17, C18, H19, N20, Q25, Q29, Q32, D120, R123, S127, N128, L130, C131, C134, S135, or H138 of SEQ ID NO:98. In certain embodiments, described herein is an antibody comprising CDRs with an amino acid sequence set forth in any one of SEQ ID NOs: 1, 9, 95, 21, 25, and 29 that binds to all of the following residues: A13, I14, R15, H16, P17, C18, H19, N20, Q25, Q29, Q32, D120, R123, S127, N128, L130, C131, C134, S135, and H138 of SEQ ID NO:98. In certain embodiments, the antibody only binds residues that participate with the antibody in strong or medium interactions. In certain embodiments, the antibody only binds residues that participate with the antibody in strong interactions.

In certain embodiments, described herein is an antibody comprising CDRs that differ from the amino acid sequence set forth in any one of SEQ ID NOs: 1, 9, 15, 21, 25, and 29 by 1, 2, 3, 4, or 5 amino acids and binds any one, two, three, four, five, six, seven, eight, nine, ten, eleven, twelve, thirteen, fourteen, fifteen, sixteen, seventeen, eighteen, nineteen, or twenty of the following residues: A13, I14, R15, H16, P17, C18, H19, N20, Q25, Q29, Q32, D120, R123, S127, N128, L130, C131, C134, S135, or H138 of SEQ ID NO:98. In certain embodiments, described herein is an antibody comprising CDRs that differ from the amino acid sequence set forth in any one of SEQ ID NOs: 1, 9, 15, 21, 25, and 29 by 1, 2, 3, 4, or 5 amino acids and binds to all of the following residues: A13, I14, R15, H16, P17, C18, H19, N20, Q25, Q29, Q32, D120, R123, S127, N128, L130, C131, C134, S135, and H138 of SEQ ID NO:98. In certain embodiments, the antibody only binds residues that participate with the antibody in strong or medium interactions. In certain embodiments, the antibody only binds residues that participate with the antibody in strong interactions.

In certain embodiments, described herein is an antibody comprising CDRs that differ from the amino acid sequence set forth in any one of SEQ ID NOs: 1, 9, 95, 21, 25, and 29 by 1, 2, 3, 4, or 5 amino acids and binds any one, two, three, four, five, six, seven, eight, nine, ten, eleven, twelve, thirteen, fourteen, fifteen, sixteen, seventeen, eighteen, nineteen, or twenty of the following residues: A13, I14, R15, H16, P17, C18, H19, N20, Q25, Q29, Q32, D120, R123, S127, N128, L130, C131, C134, S135, or H138 of SEQ ID NO:98. In certain embodiments, described herein is an antibody comprising CDRs that differ from the amino acid sequence set forth in any one of SEQ ID NOs: 1, 9, 95, 21, 25, and 29 by 1, 2, 3, 4, or 5 amino acids and bind to all of the following residues: A13, I14, R15, H16, P17, C18, H19, N20, Q25, Q29, Q32, D120, R123, S127, N128, L130, C131, C134, S135, and H138 of SEQ ID NO:98. In certain embodiments, the antibody only binds residues that that participate with the antibody in strong or medium interactions. In certain embodiments, the antibody only binds residues that that participate with the antibody in strong interactions.

In certain embodiments, described herein, is an antibody that specifically binds LIF comprising a humanized heavy chain variable region amino acid sequence at least about 80%, about 90%, about 95%, about 97%, about 98%, or about 99% identical to the amino acid sequence set forth in SEQ ID NO:72; and a humanized light chain variable region amino acid sequence at least about 80%, about 90%, about 95%, about 97%, about 98%, or about 99% identical to the amino acid sequence set forth in SEQ ID NO: 76 and binds any one, two, three, four, five, six, seven, eight, nine, ten, eleven, twelve, thirteen, fourteen, fifteen, sixteen, seventeen, eighteen, nineteen, or twenty of the following residues: A13, I14, R15, H16, P17, C18, H19, N20, Q25, Q29, Q32, D120, R123, S127, N128, L130, C131, C134, S135, or H138 of SEQ ID NO:98. In certain embodiments, described herein, is an antibody that specifically binds LIF comprising a humanized heavy chain variable region amino acid sequence at least about 80%, about 90%, about 95%, about 97%, about 98%, or about 99% identical to the amino acid sequence set forth in SEQ ID NO:72; and a humanized light chain variable region amino acid sequence at least about 80%, about 90%, about 95%, about 97%, about 98%, or about 99% identical to the amino acid sequence set forth in SEQ ID NO: 76 and binds all of the following residues: A13, I14, R15, H16, P17, C18, H19, N20, Q25, Q29, Q32, D120, R123, S127, N128, L130, C131, C134, S135, and H138 of SEQ ID NO:98. In certain embodiments, the antibody only binds residues that that participate with the antibody in strong or medium interactions. In certain embodiments, the antibody only binds residues that that participate with the antibody in strong interactions.

In certain embodiments, described herein, is an antibody that specifically binds LIF comprising a humanized heavy chain variable region amino acid sequence at least about 80%, about 90%, about 95%, about 97%, about 98%, or about 99% identical to the amino acid sequence set forth in SEQ ID NO: 96; and a humanized light chain variable region amino acid sequence at least about 80%, about 90%, about 95%, about 97%, about 98%, or about 99% identical to the amino acid sequence set forth in SEQ ID NO: 76 and binds any one, two, three, four, five, six, seven, eight, nine, ten, eleven, twelve, thirteen, fourteen, fifteen, sixteen, seventeen, eighteen, nineteen, or twenty of the following residues: A13, I14, R15, H16, P17, C18, H19, N20, Q25, Q29, Q32, D120, R123, S127, N128, L130, C131, C134, S135, or H138 of SEQ ID NO:98. In certain embodiments, described herein, is an antibody that specifically binds LIF comprising a humanized heavy chain variable region amino acid sequence at least about 80%, about 90%, about 95%, about 97%, about 98%, or about 99% identical to the amino acid sequence set forth in SEQ ID NO: 96; and a humanized light chain variable region amino acid sequence at least about 80%, about 90%, about 95%, about 97%, about 98%, or about 99% identical to the amino acid sequence set forth in SEQ ID NO: 76 and binds all of the following residues: A13, I14, R15, H16, P17, C18, H19, N20, Q25, Q29, Q32, D120, R123, S127, N128, L130, C131, C134, S135, and H138 of SEQ ID NO:98. In certain embodiments, the antibody only binds residues that that participate with the antibody in strong or medium interactions. In certain embodiments, the antibody only binds residues that that participate with the antibody in strong interactions.

Therapeutic Indications

In certain embodiments, the antibodies disclosed herein inhibit LIF signaling in cells. In certain embodiments, the $IC_{50}$ for biological inhibition of the antibody under serum starved conditions in U-251 cells is less than or equal to about 100, 75, 50, 40, 30, 20, 10, 5, or 1 nanomolar. In certain embodiments, the $IC_{50}$ for biological inhibition of the antibody under serum starved conditions in U-251 cells is less than or equal to about 900, 800, 700, 600, 500, 400, 300, 200, or 100 nanomolar.

In certain embodiments, the antibodies disclosed herein, are useful for treating tumors and cancers that express LIF. In certain embodiments, an individual treated with the antibodies of this disclosure has been selected for treatment as having a LIF positive tumor/cancer. In certain embodiments, the tumor is LIF positive or produces elevated levels of LIF. In certain embodiments, LIF positivity is determined in comparison to a reference value or a set pathological criteria. In certain embodiments, a LIF positive tumor expresses greater than 2-fold, 3-fold, 5-fold, 10-fold, 100-fold or more LIF than a non-transformed cell from which the tumor is derived. In certain embodiments, the tumor has acquired ectopic expression of LIF. A LIF positive tumor can be determined histologically using, for example, immunohistochemistry with an anti-LIF antibody; by commonly used molecular biology methods such as, for example, mRNA quantitation by real-time PCR or RNA-seq; or protein quantitation, for example, by western blot, flow cytometry, ELISA, or a homogenous protein quantitation assays (e.g., alphaLISA). In certain embodiments, the antibodies can be used to treat patients diagnosed with cancer. In certain embodiments, the cancer comprises one or more cancer stem cells or is one or more cancer stem cells.

In certain embodiments, the antibodies disclosed herein, are useful for treating tumors in cancers that express the LIF receptor (CD118). A LIF receptor positive tumor can be determined by histopathology or flow cytometry, and, in certain embodiments, comprises a cell that binds a LIF receptor antibody greater than 2×, 3×, 3×, 4×, 5×, 10× or more than an isotype control. In certain embodiments, the tumor has acquired ectopic expression of the LIF receptor. In a certain embodiment, the cancer is a cancer stem cell. In a certain embodiment, a LIF positive tumor or cancer can be determined by immunohistochemistry using anti-LIF an anti-LIF antibody. In a certain embodiment, a LIF positive tumor is determined by IHC analysis with a LIF Level in the top 10%, 20%, 30%, 40%, or top 50% of tumors.

The antibodies described herein influence numerous outcomes. In a certain embodiment, the antibodies described herein can reduce the presence of M2 macrophages in tumors by at least 10%, 20%, 30%, 40%, 50%, 60%, 70%, 80%, 90% or more in a tumor model compared to a control antibody (e.g., isotype control). M2 macrophages can be identified by staining for CCL22 and CD206 in IHC sections or by flow cytometry of tumor infiltrating immune or myeloid cells. In a certain embodiment, the antibodies described herein can reduce the binding of LIF to gp130 tumors by at least 10%, 20%, 30%, 40%, 50%, 60%, 70%, 80%, 90% or more when compared to a control antibody (e.g., isotype control). In a certain embodiment, the antibodies described herein can reduce LIF signaling by at least 10%, 20%, 30%, 40%, 50%, 60%, 70%, 80%, 90% or more in a LIF responsive cell line compared to a control antibody (e.g., isotype control). LIF signaling can be measured by, for example, western blot for phosphorylated STAT3 (a downstream target of LIF signaling). The antibodies here are also highly specific for LIF compared to other IL-6 family member cytokines. In certain embodiments, the antibodies bind human LIF with an affinity about 10×, about 50×, or about 100× greater than that of any other IL-6 family member cytokine. In certain embodiments, the LIF antibodies do not bind to other IL-6 family member cytokines that are produced in a mammalian system. In certain embodiments, the antibodies do not bind to Oncostatin M that has been produced in a mammalian system.

In certain embodiments, disclosed herein, are antibodies useful for the treatment of a cancer or tumor. In certain embodiments, the cancer comprises breast, heart, lung, small intestine, colon, spleen, kidney, bladder, head, neck, ovarian, prostate, brain, pancreatic, skin, bone, bone marrow, blood, thymus, uterine, testicular, and liver tumors. In certain embodiments, tumors which can be treated with the antibodies of the invention comprise adenoma, adenocarcinoma, angiosarcoma, astrocytoma, epithelial carcinoma, germinoma, glioblastoma, glioma, hemangioendothelioma, hemangiosarcoma, hematoma, hepatoblastoma, leukemia, lymphoma, medulloblastoma, melanoma, neuroblastoma, osteosarcoma, retinoblastoma, rhabdomyosarcoma, sarcoma and/or teratoma. In certain embodiments, the tumor/cancer is selected from the group of acral lentiginous melanoma, actinic keratosis, adenocarcinoma, adenoid cystic carcinoma, adenomas, adenosarcoma, adenosquamous carcinoma, astrocytic tumors, Bartholin gland carcinoma, basal cell carcinoma, bronchial gland carcinoma, capillary carcinoid, carcinoma, carcinosarcoma, cholangiocarcinoma, chondrosarcoma, cystadenoma, endodermal sinus tumor, endometrial hyperplasia, endometrial stromal sarcoma, endometrioid adenocarcinoma, ependymal sarcoma, Swing's sarcoma, focal nodular hyperplasia, gastronoma, germ line tumors, glioblastoma, glucagonoma, hemangioblastoma, hemangioendothelioma, hemangioma, hepatic adenoma, hepatic adenomatosis, hepatocellular carcinoma, insulinite, intraepithelial neoplasia, intraepithelial squamous cell neoplasia, invasive squamous cell carcinoma, large cell carcinoma, liposarcoma, lung carcinoma, lymphoblastic leukemia, lymphocytic leukemia, leiomyosarcoma, melanoma, malignant melanoma, malignant mesothelial tumor, nerve sheath tumor, medulloblastoma, medulloepithelioma, mesothelioma, mucoepidermoid carcinoma, myeloid leukemia, neuroblastoma, neuroepithelial adenocarcinoma, nodular melanoma, osteosarcoma, ovarian carcinoma, papillary serous adenocarcinoma, pituitary tumors, plasmacytoma, pseudosarcoma, prostate carcinoma, pulmonary blastoma, renal cell carcinoma, retinoblastoma, rhabdomyosarcoma, sarcoma, serous carcinoma, squamous cell carcinoma, small cell carcinoma, soft tissue carcinoma, somatostatin secreting tumor, squamous carcinoma, squamous cell carcinoma, undifferentiated carcinoma, uveal melanoma, verrucous carcinoma, vagina/vulva carcinoma, VIPpoma, and Wilm's tumor. In certain embodiments, the tumor/cancer to be treated with one or more antibodies of the invention comprise brain cancer, head and neck cancer, colorectal carcinoma, acute myeloid leukemia, pre-B-cell acute lymphoblastic leukemia, bladder cancer, astrocytoma, preferably grade II, III or IV astrocytoma, glioblastoma, glioblastoma multiforme, small cell cancer, and non-small cell cancer, preferably non-small cell lung cancer, lung adenocarcinoma, metastatic melanoma, androgen-independent metastatic prostate cancer, androgen-dependent metastatic prostate cancer, prostate adenocarcinoma, and breast cancer, preferably breast ductal cancer, and/or breast carcinoma. In certain embodiments, the cancer treated with the antibodies of this disclosure comprises glioblastoma. In certain embodiments, the cancer treated with one or more antibodies of this disclosure comprises pancreatic cancer. In certain embodiments, the cancer treated with one or more antibodies of this disclosure comprises ovarian cancer. In certain embodiments, the cancer treated with one or more antibodies of this disclosure comprises lung cancer. In certain embodiments, the cancer treated with one or more antibodies of this disclosure comprises prostate cancer. In certain embodiments, the cancer treated with one or more antibodies of this disclosure comprises colon cancer. In certain embodiments, the cancer treated comprises glioblastoma, pancreatic cancer, ovarian cancer, colon cancer, prostate cancer, or lung cancer. In a certain embodiment, the cancer is refractory to other treatment. In a certain embodiment, the cancer treated is relapsed. In a certain embodiment, the cancer is a relapsed/refractory glioblastoma, pancreatic cancer, ovarian cancer, colon cancer, prostate cancer, or lung cancer.

Therapeutic Methods

In certain embodiments, the antibodies can be administered by any route suitable for the administration of antibody-containing pharmaceutical compositions, such as, for example, subcutaneous, intraperitoneal, intravenous, intramuscular, intratumoral, or intracerebral, etc. In certain embodiments, the antibodies are administered intravenously. In certain embodiments, the antibodies are administered on a suitable dosage schedule, for example, weekly, twice weekly, monthly, twice monthly, etc. In certain embodiments, the antibodies are administered once every three weeks. The antibodies can be administered in any therapeutically effective amount. In certain embodiments, the therapeutically acceptable amount is between about 0.1 mg/kg and about 50 mg/kg. In certain embodiments, the therapeutically acceptable amount is between about 1 mg/kg and about 40 mg/kg. In certain embodiments, the therapeutically acceptable amount is between about 5 mg/kg and about 30 mg/kg.

Additional Therapeutic Agents

In certain embodiments, the antibodies can be administered with or during treatment with an additional therapeutic agent. In certain embodiments, the therapeutic agent comprises a recombinant protein or monoclonal antibody. In certain embodiments, the recombinant protein or monoclonal antibody comprises Etaracizumab (Abegrin), Tacatuzumab tetraxetan, Bevacizumab (Avastin), Labetuzumab, Cetuximab (Erbitux), Obinutuzumab (Gazyva), Trastuzumab (Herceptin), Clivatuzumab, Trastuzumab emtansine (Kadcyla), Ramucirumab, Rituximab (MabThera, Rituxan), Gemtuzumab ozogamicin (Mylotarg), Pertuzumab (Omnitarg), Girentuximab (Rencarex), or Nimotuzumab (Theracim, Theraloc). In certain embodiments, the monoclonal antibody comprises an immunomodulatory that targets a checkpoint inhibitor, for example PD-1 or CTLA-4. In certain embodiments, the immunomodulator comprises Nivolumab, Ipilimumab, Atezolizumab, or Pembrolizumab. In certain embodiments, the additional therapeutic agent is a chemotherapeutic agent. In certain embodiments, the chemotherapeutic agent is an alkylating agent (e.g., cyclophosphamide, ifosfamide, chlorambucil, busulfan, melphalan, mechlorethamine, uramustine, thiotepa, nitrosoureas, or temozolomide), an anthracycline (e.g., doxorubicin, adriamycin, daunorubicin, epirubicin, or mitoxantrone), a cytoskeletal disruptor (e.g., paclitaxel or docetaxel), a histone deacetylase inhibitor (e.g., vorinostat or romidepsin), an inhibitor of topoisomerase (e.g., irinotecan, topotecan, amsacrine, etoposide, or teniposide), a kinase inhibitor (e.g., bortezomib, erlotinib, gefitinib, imatinib, vemurafenib, or vismodegib), a nucleoside analog or precursor analog (e.g., azacitidine, azathioprine, capecitabine, cytarabine, fluorouracil, gemcitabine, hydroxyurea, mercaptopurine, methotrexate, or thioguanine), a peptide antibiotic (e.g., actinomycin or bleomycin), a platinum-based agent (e.g., cisplatin, oxaloplatin, or carboplatin), or a plant alkaloid (e.g., vincristine, vinblastine, vinorelbine, vindesine, podophyllotoxin, paclitaxel, or docetaxel). In some embodiments, the chemotherapeutic agent is a nucleoside analog. In some embodiments, the chemotherapeutic agent is gemcitabine. In certain embodiments, the additional therapeutic agent is radiation therapy.

Pharmaceutically Acceptable Carriers

In certain embodiments, the antibodies of the current disclosure are administered suspended in a sterile solution. In certain embodiments, the solution comprises a physiologically appropriate salt concentration (e.g., NaCl). In certain embodiments, the solution comprises between about 0.6% and 1.2% NaCl. In certain embodiments, the solution comprises between about 0.7% and 1.1% NaCl. In certain embodiments, the solution comprises between about 0.8% and 1.0% NaCl. In certain embodiments, a highly concentrated stock solution of antibody may be diluted in about 0.9% NaCl. In certain embodiments, the solution comprises about 0.9% NaCl. In certain embodiments, the solution further comprises one or more of: buffers, for example, acetate, citrate, histidine, succinate, phosphate, bicarbonate and hydroxymethylaminomethane (Tris); surfactants, for example, polysorbate 80 (Tween 80), polysorbate 20 (Tween 20), polysorbate and poloxamer 188; polyol/disaccharide/polysaccharides, for example, glucose, dextrose, mannose, mannitol, sorbitol, sucrose, trehalose, and dextran 40; amino acids, for example, histidine, glycine or arginine; antioxidants, for example, ascorbic acid, methionine; and chelating agents, for example, EGTA or EGTA. In certain embodiments, the antibodies of the current disclosure are shipped/stored lyophilized and reconstituted before administration. In certain embodiments, lyophilized antibody formulations comprise a bulking agent such as, mannitol, sorbitol, sucrose, trehalose, and dextran 40. In a certain embodiment, anti-LIF antibodies of this disclosure can be shipped and stored as a concentrated stock solution to be diluted at the treatment site of use. In certain embodiments, the stock solution comprises about 25 mM histidine, about 6% sucrose, about 0.01% polysorbate, and about 20 mg/mL of anti-LIF antibody.

EXAMPLES

The following illustrative examples are representative of embodiments of the software applications, systems, and methods described herein and are not meant to be limiting in any way.

Example 1—Generation of Rat Antibodies Specific for LIF

A cDNA encoding amino acids 23-202 of human LIF was cloned into expression plasmids (Aldevron GmbH, Freiburg, Germany). Groups of laboratory rats (Wistar) were immunized by intradermal application of DNA-coated gold-particles using a hand-held device for particle-bombardment ("gene gun"). Cell surface expression on transiently transfected HEK cells was confirmed with anti-tag antibodies recognizing a tag added to the N-terminus of the LIF protein. Serum samples were collected after a series of immunizations and tested in flow cytometry on HEK cells transiently transfected with the aforementioned expression plasmids. Antibody-producing cells were isolated and fused with mouse myeloma cells (Ag8) according to standard procedures. Hybridomas producing antibodies specific for LIF were identified by screening in a flow cytometry assay as described above. Cell pellets of positive hybridoma cells were prepared using an RNA protection agent (RNAlater, cat. #AM7020 by ThermoFisher Scientific) and further processed for sequencing of the variable domains of the antibodies.

Example 2—Generation of Mouse Antibodies Specific for LIF

A cDNA encoding amino acids 23-202 of human LIF was cloned into expression plasmids (Aldevron GmbH, Freiburg, Germany). Groups of laboratory mice (NMRI) were immunized by intradermal application of DNA-coated gold-particles using a hand-held device for particle-bombardment ("gene gun"). Cell surface expression on transiently transfected HEK cells was confirmed with anti-tag antibodies recognizing a tag added to the N-terminus of the LIF protein. Serum samples were collected after a series of immunizations and tested in flow cytometry on HEK cells transiently transfected with the aforementioned expression plasmids. Antibody-producing cells were isolated and fused with mouse myeloma cells (Ag8) according to standard procedures. Hybridomas producing antibodies specific for LIF were identified by screening in a flow cytometry assay as described above. Cell pellets of positive hybridoma cells were prepared using an RNA protection agent (RNAlater, cat. #AM7020 by ThermoFisher Scientific) and further processed for sequencing of the variable domains of the antibodies.

Example 3—Humanization of Rat Antibodies Specific for LIF

One clone from the rat immunization (5D8) was chosen for subsequent humanization. Humanization was conducted using standard CDR grafting methods. The heavy chain and light chain regions were cloned from the 5D8 hybridoma using standard molecular cloning techniques and sequenced by the Sanger method. A BLAST search was then conducted against human heavy chain and light chain variable sequences and 4 sequences from each were chosen as acceptor frameworks for humanization. These acceptor frameworks were deimmunized to remove T cell response epitopes. The heavy chain and light chain CDR1, CDR2 and CDR3 of 5D8 were cloned into the 4 different heavy chain acceptor frameworks (H1 to H4), and 4 different light chain frameworks (L1 to L4). Then all 16 different antibodies were tested for: expression in CHO-S cells (Selexis); inhibition of LIF-induced STAT3 phosphorylation; and binding affinity by Surface Plasmon Resonance (SPR). These experiments are summarized in Table 1.

TABLE 1

Summary of 5D8 humanization

| Heavy chain light chain combination | Inhibition of LIF-induced pSTAT3 from FIG. 1 | Affinity by SPR $K_{D1}$ (pM) | Expression (ug/mL) |
|---|---|---|---|
| H0L0 | +++ | 133 ± 46 | 393 |
| H1L1 | − | N/A | 627 |
| H1L2 | +++ | 55 ± 23 | 260 |
| H1L3 | +++ | 54 ± 31 | 70 |
| H1L4 | − | N/A | 560 |
| H2L1 | − | N/A | 369 |
| H2L2 | +++ | 52 ± 22 | 392 |
| H2L3 | ++ | 136 ± 19 | 185 |
| H2L4 | − | N/A | 78 |
| H3L1 | N/A | N/A | No expression |
| H3L2 | N/A | N/A | No expression |
| H3L3 | N/A | N/A | No expression |
| H3L4 | N/A | N/A | No expression |
| H4L1 | − | N/A | 259 |
| H4L2 | ++ | 913 ± 308 | 308 |
| H4L3 | + | | 252 |
| H4L4 | − | N/A | 186 |

N/A = Not attempted;
H0L0 = chimeric antibody with full rat heavy and light chain variable regions The expression performance of the transfected cells was compared in Erlenmeyer flasks (seeding $3 \times 10^5$ cells/mL, 200 mL culture volume) within fed-batch cultivation after 10 days of cell culture. At this point cells were harvested and the secreted antibody purified using a Protein A column and then quantitated. All humanized antibodies expressed except those using the H3 heavy chain.

Inhibition of LIF-induced STAT3 phosphorylation at tyrosine 705 was determined by western blot. U251 glioma cells were plated in 6-well plates at a density of 100.000 cells/well. Cells were cultured in complete medium for 24 hours before any treatment and after that, cells were serum starved for 8 hours. After that, cells with the indicated antibodies over night at a concentration of 10 μg/ml. After treatment, proteins were obtained in radio-immunoprecipitation assay (RIPA) lysis buffer containing phosphatase and protease inhibitors, quantified (BCA-protein assay, Thermo Fisher Scientific) and used in western blot. For western blot, membranes were blocked for 1 hour in 5% non-fat dried milk—TBST and incubated with the primary antibody overnight (p-STAT3, catalog #9145, Cell Signaling or STAT3, catalog #9132, Cell Signaling) or 30 minutes (β-actin-peroxidase, catalog #A3854, Sigma-Aldrich). Membranes were then washed with TBST, incubated with secondary and washed again. Proteins were detected by chemiluminescence (SuperSignal Substrate, catalog #34076, Thermo Fisher Scientific). These results are shown in FIG. 1. The darker the pSTAT3 band the less inhibition is present. Inhibition was high in lanes labeled 5D8 (non humanized rat), A(H0L0), C (H1L2), D (H1L3), and G (H2L2); inhibition was moderate in H (H2L3), O (H4L2), and P (H4L3); inhibition was absent in B (H1L1), E (H1L4), F (H2L1), I (H2L4), N (H4L1) and Q (H4L4).

Antibodies that exhibited inhibition of LIF-induced STAT3 phosphorylation were then analyzed by SPR to determine binding affinity. Briefly, binding of the A(H0L0), C (H1L2), D (H1L3), and G (H2L2), H (H2L3) and O (H4L2) humanized antibodies to amine coupled hLIF was observed using a Biacore™ 2002 Instrument. Kinetic constants and affinities were determined by mathematical sensorgram fitting (Langmuir interaction model [A+B=AB]) of all sensorgrams generated on all sensor chip surfaces at six ligand concentrations. The best fitted curves (minimal Chi2) of each concentration were used for calculation of kinetic constants and affinities. See Table 1.

Since the experimental setup used bivalent antibodies as analytes, best fitted sensorgrams, were also analyzed on basis of a bivalent analyte fitting model [A+B=AB; AB+B=AB2] in order to obtain a more detailed insight into the target binding mechanism of the humanized antibodies. Kinetic sensorgram analysis using a bivalent fitting model [A+B=AB; AB+B=AB2] confirmed the relative affinity ranking of the mAb samples.

The humanized 5D8 comprising H2 and L2 was selected for more in-depth analysis due to its high binding affinity and high yield from batch culture.

Example 4—Humanization of Clone 5D8 Improves Binding to LIF

We selected the H2L2 clone (h5D8) for further analysis and compared binding by SPR to the parental rat 5D8 (r5D8) and a mouse clone 1B2. The 1B2 antibody is a previously disclosed mouse anti-LIF antibody previously deposited at the Deutsche Sammlung von Mikroorganismen und Zellkulturen GmbH (DSM ACC3054) and was included for comparison purposes. Recombinant human LIF, purified from E. coli and HEK-293 cells, respectively, were used as ligands. The LIF from human or E. coli sources was covalently coupled to the surface of Biacore optical sensor chips using amine coupling chemistry, and binding affinities were calculated from the kinetic constants.

Materials and Methods

Human LIF from E. coli was obtained from Millipore, reference LIF 1010; human LIF from HEK-293 cells was obtained from ACRO Biosystems, reference LIF-H521b. LIF was coupled to the sensor chips using the Biacore Amine Coupling Kit (BR-1000-50; GE-Healthcare, Uppsala). Samples were run on a Biacore™ 2002 Instrument using CM5 optical sensor chips (BR-1000-12; GE-Healthcare, Uppsala). Biacore HBS-EP buffer was used during the machine runs (BR-1001-88; GE-Healthcare, Uppsala). Kinetic analysis of binding sensorgrams was performed using BIAevaluation 4.1 software. Kinetic constants and affinities were determined by mathematical sensorgram fitting (Langmuir interaction model [A+B=AB]) of all sensorgrams generated on all sensor chip surfaces at increasing analyte concentrations. Sensorgrams were also analyzed on the basis of a bivalent analyte sensorgram fitting model [A+B=AB; AB+B=AB$_2$], including component analysis, in order to generate an estimate on the bivalent contribution to the determined Langmuir antibody—target affinities (e.g., avidity contribution). The best fitted curves (minimal Chi$^2$) of each concentration were used for calculation of kinetic constants and affinities. Summaries of these affinity experiments are shown in Table 2 (human LIF made in E. coli) and Table 3 (human LIF made in HEK 293 cells).

TABLE 2

Improved binding of 5D8 after humanization

| | $K_D$ [pM] | |
|---|---|---|
| hLIF (E. coli) | Langmuir 1:1 sensorgram fitting | Bivalent analyte fitting |
| Mouse 1B2 | 400 ± 210 | 1500 ± 200 |
| r5D8 (Rat) | 130 ± 30 | 780 ± 130 |
| h5D8 (humanized) | 26 ± 14 | 82 ± 25 |

TABLE 3

Improved binding of 5D8 after humanization

| | $K_D$ [pM] | |
|---|---|---|
| hLIF (HEK 293) | Langmuir 1:1 sensorgram fitting | Bivalent analyte fitting |
| Mouse 1B2 | 320 ± 150 | 3900 ± 900 |
| r5D8 (rat) | 135 ± 100 | 410 ± 360 |
| h5D8 (humanized) | 13 ± 6 | 63 ± 30 |

The Langmuir 1:1 sensorgram fitting model from this set of experiments indicates that the humanized 5D8 (h5D8) antibody bound with ~10-25 times higher affinity to human LIF than mouse 1B2 and r5D8.

Next, the h5D8 antibody was tested against LIF of multiple species by SPR. h5D8 SPR binding kinetics were performed for recombinant LIF analytes derived from different species and expression systems: human LIF (*E. coli*, HEK293 cells); mouse LIF (*E. coli*, CHO cells); rat LIF (*E. coli*); cynomolgus monkey LIF (yeast, HEK293 cells).

Materials and Methods

The h5D8 antibody was immobilized to the sensor chip surface by non covalent, Fc specific capturing. Recombinant, Ig(Fc) specific *S. aureus* Protein A/G was used as capturing agent, allowing sterically uniform and flexible presentation of the anti-LIF antibody to the LIF analytes. Sources of the LIF analytes are as follows: Human LIF (from *E. coli*; Millipore reference LIF 1050); Human LIF (from HEK cells ACRO Biosystems LIF-H521); Mouse LIF (*E. coli*; Millipore Cat. No NF-LIF2010); Mouse LIF (from CHO cells; Reprokine Catalog # RCP09056); Monkey LIF (yeast Kingfisher Biotech Catalog # RP1074Y); Monkey LIF produced in HEK-293 cell. Overall h5D8 exhibited binding to LIF from several species. A summary of this affinity experiment is shown in

TABLE 4

Broad species reactivity of humanized 5D8

| | Langmuir 1:1 sensorgram fitting | | |
|---|---|---|---|
| Analyte | mean $K_a$ (1/Ms)[$10^{-5}$] | mean $K_d$ (1/S) [$10^{-5}$] | mean $K_D$ [pM] |
| Human LIF (*E.coli*) | 8.5 ± 0.7 | 7.2 ± 0.7 | 86 ± 9 |
| Human LIF (HEK-293) | 5.5 ± 0.02 | 3.1 ± 0.7 | 56 ± 13 |
| Mouse LIF (*E.coli*) | 21.4 ± 3.7 | 5.7 ± 1.0 | 27 ± 6 |
| Mouse LIF (CHO cells) | 6.5 ± 0.7 | 1.1 ± 0.3 | 17 ± 4 |
| Cyno Monkey LIF (yeast) | 6.3 ± 0.8 | 5.4 ± 0.7 | 89 ± 10 |
| Cyno Monkey LIF (HEK-293) | 2.4 ± 0.2 | 3.3 ± 0.3 | 134 ± 6 |

Figure 2A:
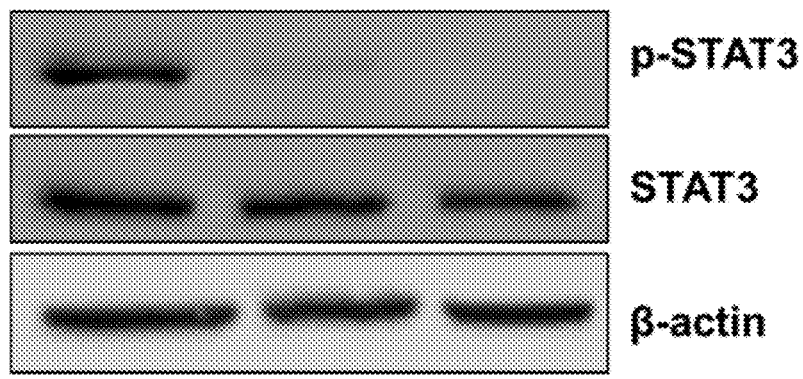
FIG. 2A and FIG. 2B depict western blots showing inhibition of LIF-induced STAT3 phosphorylation humanized and parental 5D8 antibody.
Figure 2B:
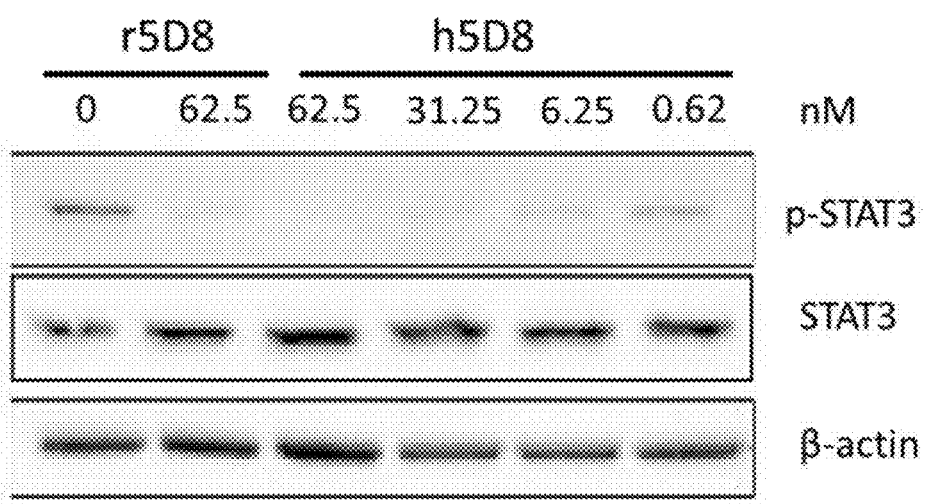

Example 5—Humanized Clone 5D8 Inhibits LIF-Induced Phosphorylation of STAT3 In Vitro To determine the biological activity of h5D8, the humanized and parental versions were tested in a cell culture model of LIF activation. FIG. 2A shows that the humanized clone exhibited increased inhibition of STAT3 phosphorylation (Tyr 705) when a glioma cell line was incubated with human LIF. FIG. 2B shows an experiment with the same set up of FIG. 2A repeated with different dilutions of the h5D8 antibody.

Methods

U251 glioma cells were plated in 6-well plates at a density of 150,000 cells/well. Cells were cultured in complete medium for 24 hours before any treatment. After that, cells were treated over night or not (control cells) with r5D8 anti-LIF antibody or h5D8 anti-LIF antibody at a concentration of 10 μg/ml.

After treatment, proteins were obtained in radio-immunoprecipitation assay (RIPA) lysis buffer containing phosphatase and protease inhibitors, quantified (BCA-protein assay, Thermo Fisher Scientific) and used in western blot. For western blot, membranes were blocked for 1 hour in 5% non-fatty milk—TBST and incubated with the primary antibody overnight (p-STAT3, catalog #9145, Cell Signaling or STAT3, catalog #9132, Cell Signaling) or 30 minutes (β-actin-peroxidase, catalog #A3854, Sigma-Aldrich). Membranes were then washed with TBST, incubated with secondary antibody if necessary, and washed again. Proteins were detected by chemiluminescence (SuperSignal Substrate, catalog #34076, Thermo Fisher Scientific).

Figure 3A:
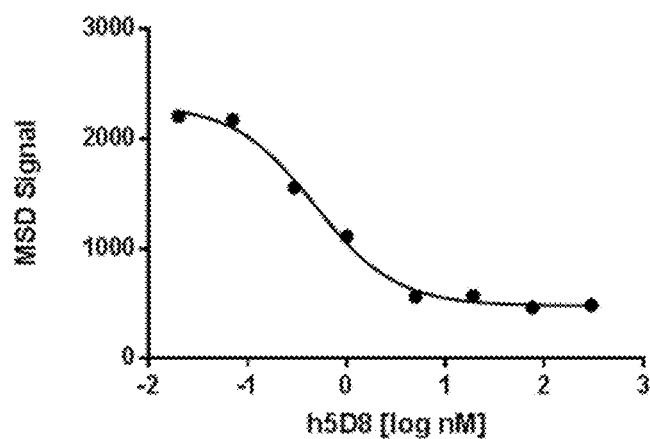
FIG. 3A shows an IC$_{50}$ for LIF inhibition in U-251 cells using the h5D8 antibody.
Figure 3B:
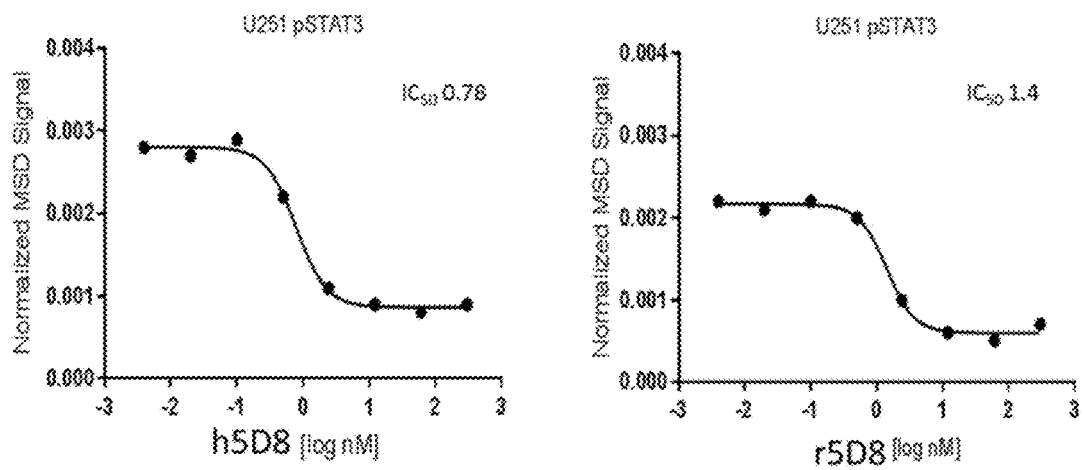
FIG. 3B shows representative IC$_{50}$ dose response curves of r5D8 and h5D8-1 inhibition of pSTAT3 under endogenous LIF stimulation conditions. Shown are the representative curves (n=1 h5D8, n=2 r5D8).

Example 6—$IC_{50}$ Value of h5D8 Antibody Treatment on Endogenous Levels of LIF in U-251 Cells We also determined an $IC_{50}$ of as low as 490 picomolar (FIG. 3A) for biological inhibition for h5D8 under serum starved conditions in U-251 cells. See representative results FIGS. 3A and 3B and Table 5.

TABLE 5

| Cell Line Tissue | Cell Line Name | Treatment | $IC_{50}$ (nM) | | | | $IC_{90}$ (nM) | JAK inhibition (%) |
|---|---|---|---|---|---|---|---|---|
| | | | n = 1 | n = 2 | Mean | SD | Mean | Mean |
| | | Endogenous LIF Condition | | | | | | |
| GBM | U251 | h5D8 | 0.78 | 0.54 | 0.66 | 0.12 | 4.1 | 84% |
| | | r5D8 | 1.6 | 1.5 | 1.4 | 0.15 | 8.5 | 86% |
| | | | 1.2 | 1.4 | | | | |

Methods

The U-251 cells were seeded at 600,000 cells per 6 cm plate (per condition). Cells were treated with h5D8 in corresponding concentration (titration) overnight at 37° C., under serum starvation (0.1% FBS). As a positive control for pSTAT3, recombinant LIF (R&D #7734-LF/CF) was used to stimulate the cells at 1.79 nM for 10 min at 37° C. As a negative control of pSTAT3, the JAK I inhibitor (Calbiochem #420099) was used at 1 uM for 30 min at 37° C. Cells were then harvested on ice for lysates following the Meso Scale Discovery Multi-Spot Assay System Total STAT3 (Cat# K150SND-2) and Phospho-STAT3 (Tyr705) (Cat# K150SVD-2) kits' protocol, to measure protein levels detectable by the MSD Meso Sector 5600.

Example 7—Additional Antibodies that Specifically Bind to Human LIF

Other rat antibody clones (10 G7 and 6B5) that specifically bind human LIF were identified and a summary of their binding characteristics are shown below in Table 6, clone 1B2 served as a comparison.

Methods

Kinetic real time binding analysis was performed for anti-LIF mAbs 1B2, 10 G7 and 6B5, immobilized on the surface of CM5 optical sensor chips, applying recombinant LIF target proteins [human LIF (*E. coli*); Millipore Cat. No. LIF 1010 and human LIF (HEK293 cells); ACRO Biosystems Cat. No. LIF-H521b] as analytes.

Kinetic constants and affinities were obtained by mathematical sensorgram fitting using a Langmuir 1:1 binding model applying global (simultaneous fitting of sensorgram sets) as well as single curve fitting algorithms. Plausibility of global fits was assessed by $k_{obs}$ analysis.

TABLE 6

Affinity measurements of additional anti-LIF antibodies

| | | Langmuir 1:1 sensorgram fitting | | |
|---|---|---|---|---|
| Analyte | clone | mean $K_a$ (1/Ms) | mean $K_d$ (1/S) | mean $K_D$ [nM] |
| Human LIF (*E. coli*) | 1B2 | 1.1 ± 0.4E5 | 1.1 ± 0.3E−3 | 9.7 ± 1.4 |
| Human LIF (HEK-293) | 1B2 | 2.0 ± 0.04E6 | 1.4 ± 0.2E−3 | 0.7 ± 0.03 |
| Human LIF (*E. coli*) | 10G7 | 7.9 ± 5.8E4 | 6.0 ± 2.3E−4 | 12.6 ± 9.5 |
| Human LIF (HEK-293) | 10G7 | 3.6 ± 1.75E5 | 3.1 ± 0.5E−4 | 1.1 ± 0.6 |
| Human LIF (*E. coli*) | 6B5 | N/A | N/A | N/A |
| Human LIF (HEK-293) | 6B5 | 3.6 ± 1.7E5 | 3.1 ± 0.5E−4 | 62 ± 6 |

Figure 4:
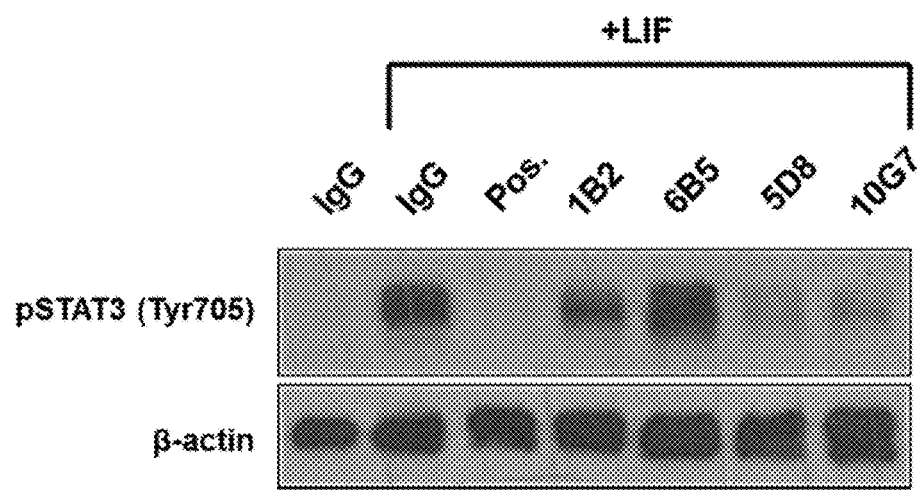
FIG. 4 depicts a western blot showing inhibition of LIF-induced STAT3 phosphorylation of different monoclonal antibodies described in this disclosure.

Example 8—Additional Anti LIF Antibodies Inhibit LIF-Induced Phosphorylation of STAT3 In Vitro Additional clones were tested for their ability to inhibit LIF-induced phosphorylation of STAT3 in cell culture. As shown in FIG. 4 clones 10 G7 and the previously detailed r5D8 exhibited high inhibition of LIF-induced STAT3 phosphorylation, compared to the 1B2 clone. Anti-LIF polyclonal anti-sera (pos.) was included as a positive control While 6B5 exhibited no inhibition, this may be explained by a possible lack of 6B5 binding to non-glycosylated LIF which was used in this experiment.

Methods

Patient derived glioma cells were plated in 6-well plates at a density of 150,000 cells/well. Cells were cultured in GBM medium that consisted of Neurobasal medium (Life Technologies) supplemented with B27 (Life Technologies), penicillin/streptomycin and growth factors (20 ng/ml EGF and 20 ng/ml FGF-2 [PeproTech]) for 24 hours before any treatment. The following day, cells were treated or not with recombinant LIF produced in *E. coli* or a mix of recombinant LIF plus the indicated antibodies for 15 minutes (final concentration of 10 µg/ml for the antibodies and 20 ng/ml of recombinant LIF). After treatment, proteins were obtained in radio-immunoprecipitation assay (RIPA) lysis buffer containing phosphatase and protease inhibitors, quantified (BCA-protein assay, Thermo Fisher Scientific) and used in western blot. For western blot, membranes were blocked for 1 hour in 5% non-fatty milk—TBST and incubated with the primary antibody overnight (p-STAT3, catalog #9145, Cell Signaling) or 30 minutes (β-actin-peroxidase, catalog #A3854, Sigma-Aldrich). Membranes were then washed with TBST, incubated with secondary antibody if necessary, and washed again. Proteins were detected by chemiluminescence (SuperSignal Substrate, catalog #34076, Thermo Fisher Scientific).

Example 9—LIF is Highly Overexpressed Across Multiple Tumor Types

Figure 5:
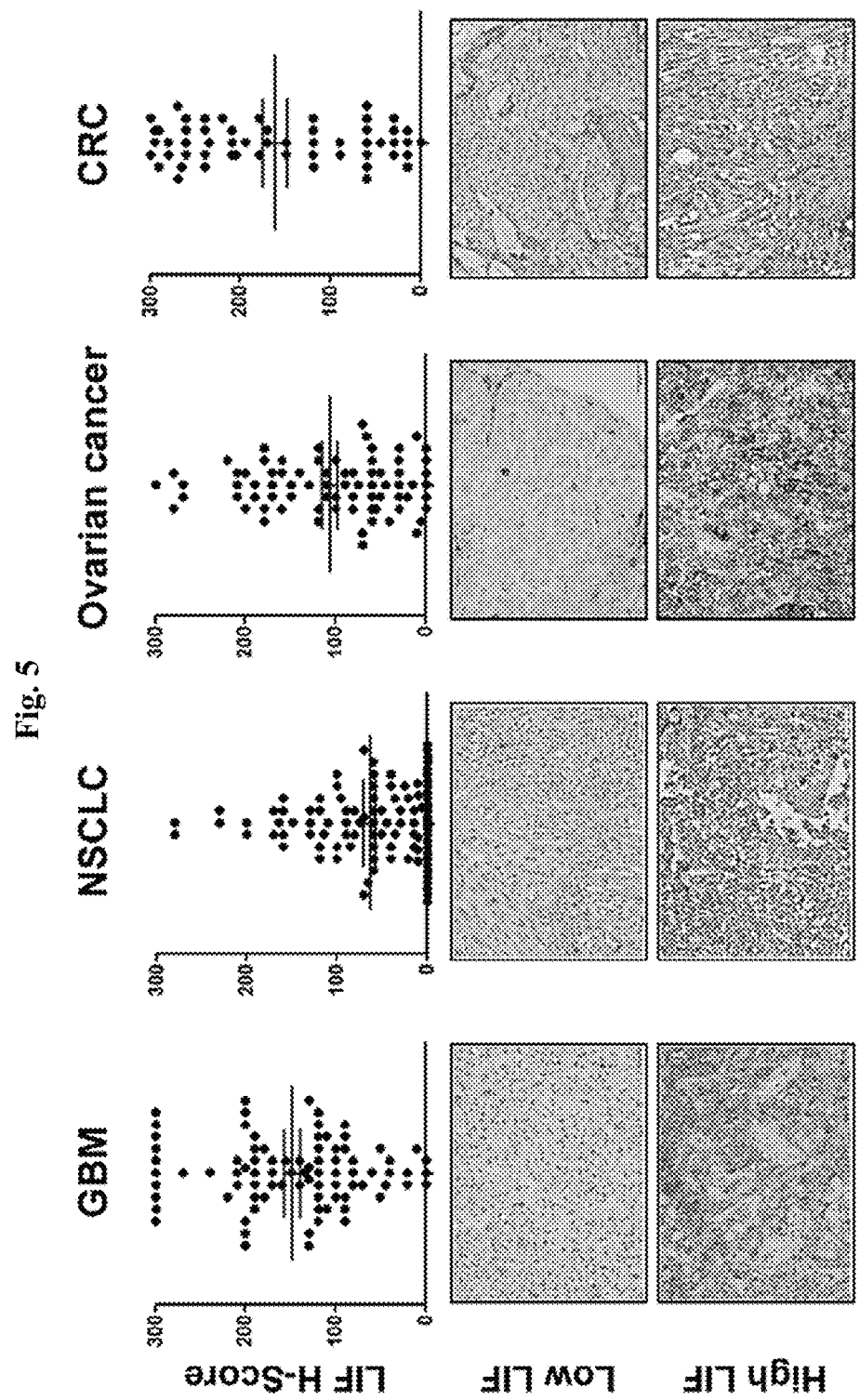
FIG. 5 depicts immunohistochemistry staining and quantitation of LIF expression in glioblastoma multiforme (GBM), NSCLC (non-small cell lung carcinoma), ovarian cancer, and colorectal cancer tumors from human patients. Bars represent mean+/−SEM.

Immunohistochemistry was conducted on multiple human tumor types to determine the degree of LIF expression. As shown in FIG. 5 LIF is highly expressed in glioblastoma multiforme (GBM), non-small cell lung cancer (NSCLC), ovarian cancer, and colorectal cancer (CRC).

Figure 6:
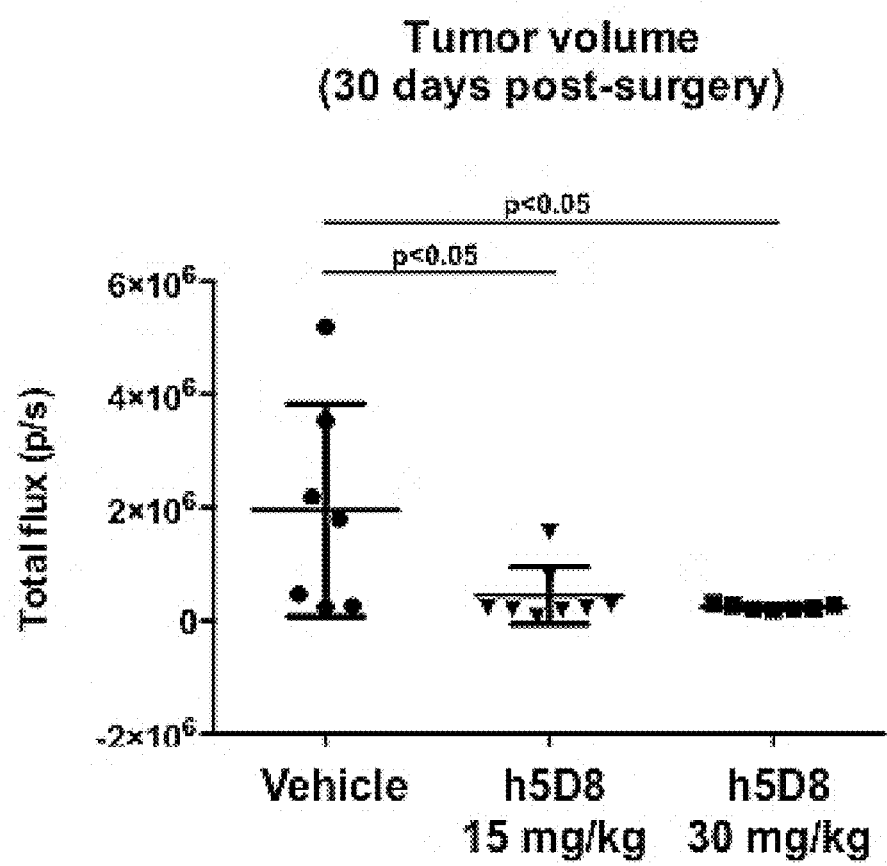
FIG. 6 is a graph showing an experiment conducted in a mouse model of non-small cell lung cancer using the humanized 5D8 antibody.

Example 10—Humanized Clone h5D8 Inhibits Tumor Growth in a Mouse Model of Non-Small Cell Lung Carcinoma To determine the ability of the humanized 5D8 clone to inhibit a LIF positive cancer in vivo this antibody was tested in a mouse model of non-small cell lung carcinoma (NSCLC). FIG. 6 shows reduced tumor growth in mice treated with this antibody compared to a vehicle negative control.

Methods

The murine non-small cell lung cancer (NSCLC) cell line KLN205 with high LIF levels was stably infected with lentivirus expressing the firefly luciferase gene for in vivo bioluminescence monitoring. To develop the mouse model, $5 \times 10^5$ KLN205 non-small cell lung cancer (NSCLC) cells were orthotopically implanted into the left lung of 8-week-old immunocompetent syngeneic DBA/2 mice by intercostal puncture. Mice were treated with a control vehicle or with 15 mg/kg or 30 mg/kg of the h5D8 antibody intraperitoneally twice a week and tumor growth was monitored by bioluminescence. For the bioluminescence imaging, mice received an intraperitoneal injection of 0.2 mL of 15 mg/mL D-luciferin under 1-2% inhaled isoflurane anesthesia. The bioluminescence signals were monitored using the IVIS system 2000 series (Xenogen Corp., Alameda, Calif., USA) consisting of a highly sensitive cooled CCD camera. Living Image software (Xenogen Corp.) was used to grid the imaging data and integrate the total bioluminescence signals in each boxed region. Data were analyzed using the total photon flux emission (photons/second) in the regions of interest (ROI). The results demonstrate that treatment with the h5D8 antibody promote tumor regression. Data are presented as mean±SEM.

Figure 7A:
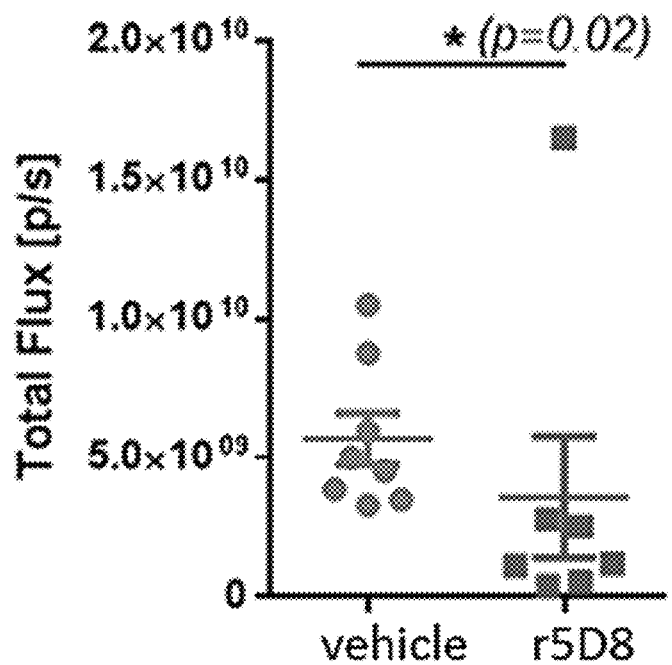
FIG. 7A shows the effect of r5D8 on inhibition of U251 cells in an orthotopic mouse model of GBM quantitation shown at day 26.
Figure 7B:
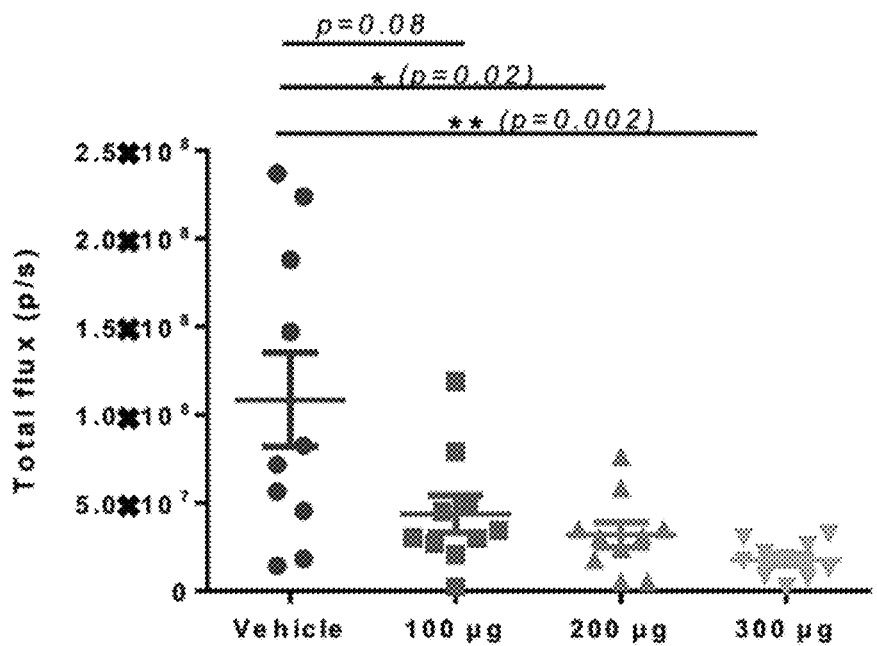
FIG. 7B shows data from mice inoculated with luciferase expressing human U251 GBM cells and then treated with 100, 200 or 300 μg of h5D8 or vehicle twice a week. Tumor size was determined by bioluminescence (Xenogen IVIS Spectrum) on day 7. The graph shows individual tumor measurements with horizontal bars indicating mean±SEM. Statistical significance was calculated using the unpaired non-parametric Mann-Whitney U-test.

Example 11—h5D8 Inhibits Tumor Growth in a Mouse Model of Glioblastoma Multiforme In an orthotopic GBM tumor model using a luciferase expressing human cell line U251, r5D8 significantly reduced tumor volumes in mice administered 300 µg r5D8 and h5D8 by intraperitoneal (IP) injection twice a week. Results of this study are shown in FIG. 7A (quantitation at day 26 post treatment). This experiment was also conducted using humanized h5D8 mice treated with 200 µg or 300 µg showed a statistically significant reduction in tumor after 7 days of treatment.

Methods

U251 cells stably expressing luciferase were harvested, washed in PBS, centrifuged at 400 g for 5 min, resuspended in PBS and counted with an automated cell counter (Countess, Invitrogen). Cells were kept on ice to maintain optimal viability. Mice were anaesthetized with intraperitoneal administration of Ketamine (Ketolar50®)/Xylacine (Rompún®) (75 mg/kg and 10 mg/kg respectively). Each mouse was carefully placed in the stereotactic device and immobilized. Hair from the head was removed with depilatory cream, and the head skin was cut with a scalpel to expose the skull. A small incision was carefully made with a drill in the coordinates 1.8 mm lateral and 1 mm anterior to the Lambda. 5 µL of cells were inoculated using a Hamilton 30 G syringe into the right corpus striatum, at 2.5 mm of depth. Head incision was closed with Hystoacryl tissue adhesive (Braun) and mice were injected with subcutaneous analgesic Meloxicam (Metacam®) (1 mg/kg). The final cell number implanted into each mouse was $3\times10^5$.

Mice were treated twice a week with h5D8 administered intraperitoneally. Treatment was initiated on day 0, immediately after tumor cell inoculation. Mice received a total of 2 doses of h5D8 or vehicle control.

Body weight and tumor volume: Body weight was measured 2 times/week and tumor growth was quantified by bioluminescence on day 7 (Xenogen IVIS Spectrum). To quantify bioluminescence activity in vivo, mice were anaesthetized using isofluorane, and injected intraperitoneally with luciferin substrate (PerkinElmer) (167 µg/kg).

Tumor size as determined by bioluminescence (Xenogen IVIS Spectrum) was evaluated at day 7. The individual tumor measurements and mean±SEM for each treatment group were calculated. Statistical significance was determined by the unpaired non-parametric Mann-Whitney U-test.

Example 12—h5D8 Inhibits Tumor Growth in a Mouse Model of Ovarian Cancer

The efficacy of r5D8 was evaluated in two other syngeneic tumor models. In the ovarian orthotopic tumor model ID8, IP administration of 300 µg r5D8 twice weekly significantly inhibited tumor growth as measured by abdominal volume (FIGS. 8A and 8B). Results in FIG. 8C show that h5D8 also reduced tumor volume at a dose of 200 µg and above.

Methods

ID8 cells were cultured in Dulbecco's Modified Eagle Medium (DMEM) (Gibco, Invitrogen), supplemented with 10% Fetal Bovine Serum (FBS) (Gibco, Invitrogen), 40 U/mL Penicillin and 40 µg/mL Streptomycin (PenStrep) (Gibco, Invitrogen) and 0.25 µg/mL Plasmocin (Invivogen).

The ID8 cells were harvested, washed in PBS, centrifuged at 400 g for 5 min and resuspended in PBS. Cells were kept on ice to maintain optimal viability and 200 µL of the cell suspension was injected intraperitoneally with a 27 G needle. The final cell number implanted into mice was $5\times10^6$.

Mice were treated twice weekly with h5D8 administered ip at different doses as indicated. Body weights were measured 2 times/week and tumor progression was monitored by measuring abdominal girth using a caliper (Fisher Scientific).

Example 13—r5D8 Inhibits Tumor Growth in a Mouse Model of Colorectal Cancer

Figure 9A:
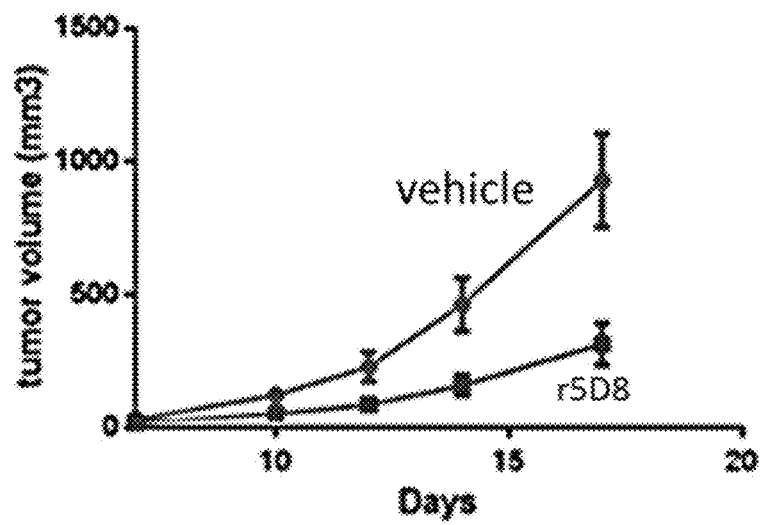
FIG. 9A shows the effect of r5D8 on inhibition of growth of colorectal cancer cells in an syngeneic mouse model.
Figure 9B:
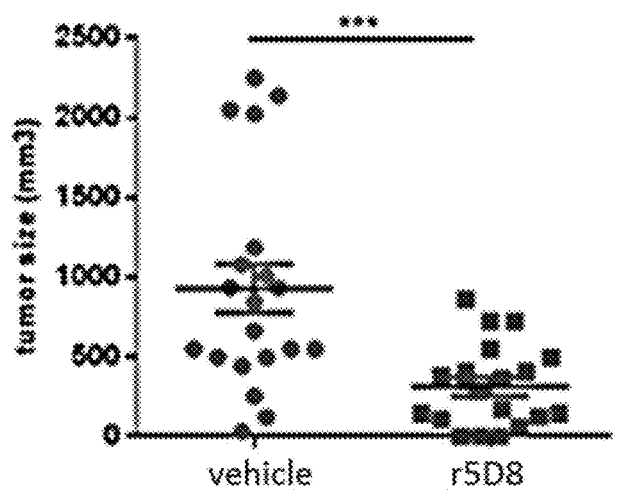
FIG. 9B shows the individual measurements of tumors at day 17.

In mice with subcutaneous colon CT26 tumors, r5D8 (administered 300 µg IP twice weekly) significantly inhibited tumor growth (FIGS. 9A and 9B).

Methods

CT26 cells were cultured in Roswell Park Memorial Institute medium (RPMI [Gibco, Invitrogen]), supplemented with 10% Fetal Bovine Serum (FBS), 40 U/mL penicillin and 40 µg/mL streptomycin (PenStrep) and 0.25 µg/mL Plasmocin.

CT26 cells ($8\times10^5$) were trypsinized, rinsed with PBS, centrifuged at 400 g for 5 minutes and resuspended in 100 µL PBS. Cells were kept on ice to avoid cell death. The CT26 cells were administered to mice via subcutaneous injection using a 27 G needle.

300 µg r5D8, or vehicle control, was administered to the mice via intraperitoneal injection (IP) twice weekly from day 3 post CT26 cell implant.

Body weight and tumor volumes were measured three times per week. Tumor volume was measured using a caliper (Fisher Scientific).

Example 14—r5D8 Reduces Inflammatory Infiltration in Tumor Models

Figure 10A:
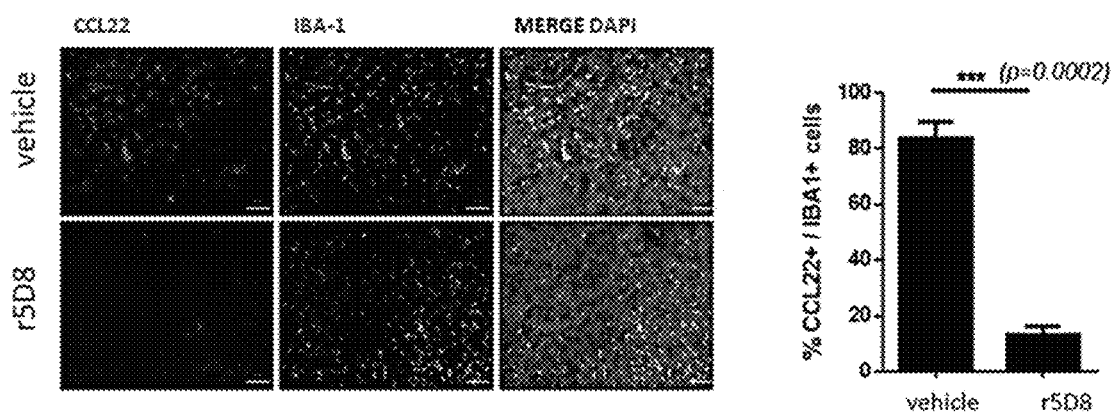
FIG. 10A shows reduction of macrophage infiltration to tumor sites in an orthotopic mouse model of GBM with a representative image and quantitation of CCL22+ cells.
Figure 10B:
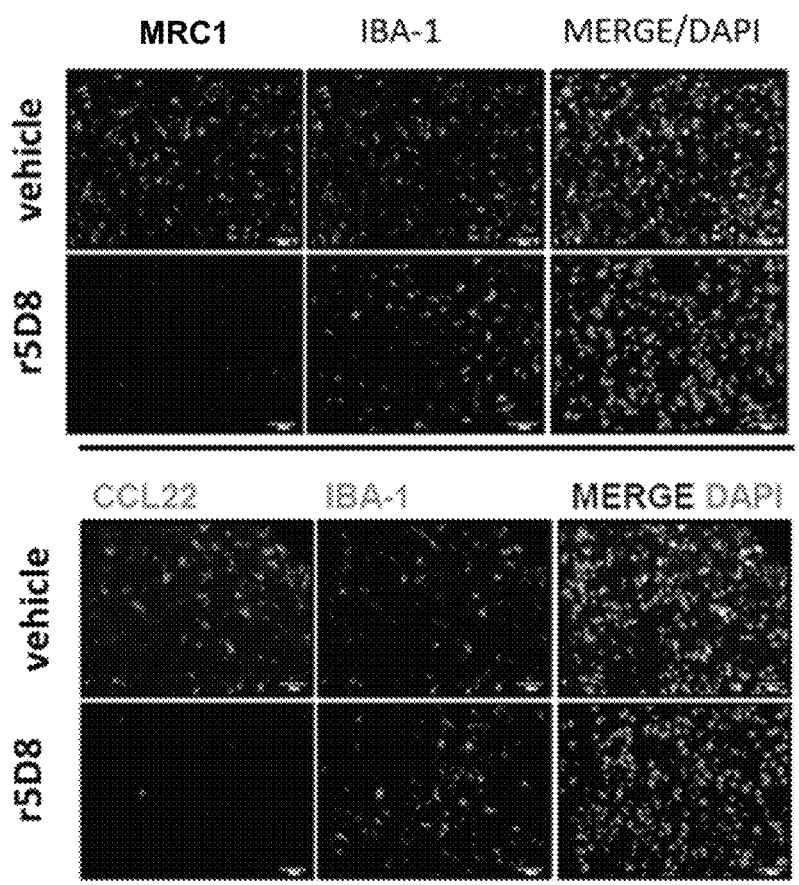
FIG. 10B shows reduction of macrophage infiltration in a human organotypic tissue slice culture model.
Figure 10C:
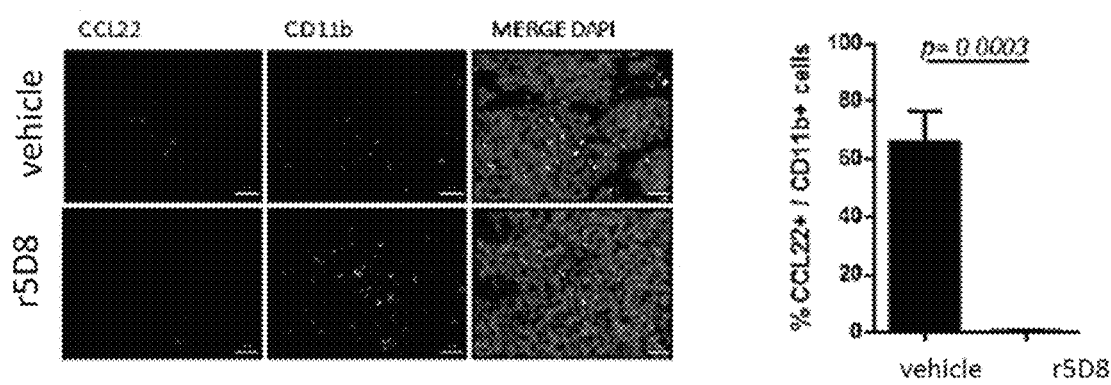
FIG. 10C shows reduction of macrophage infiltration to tumor sites in a syngeneic mouse model of ovarian cancer with a representative image and quantitation of CCL22+ cells.
Figure 10D:
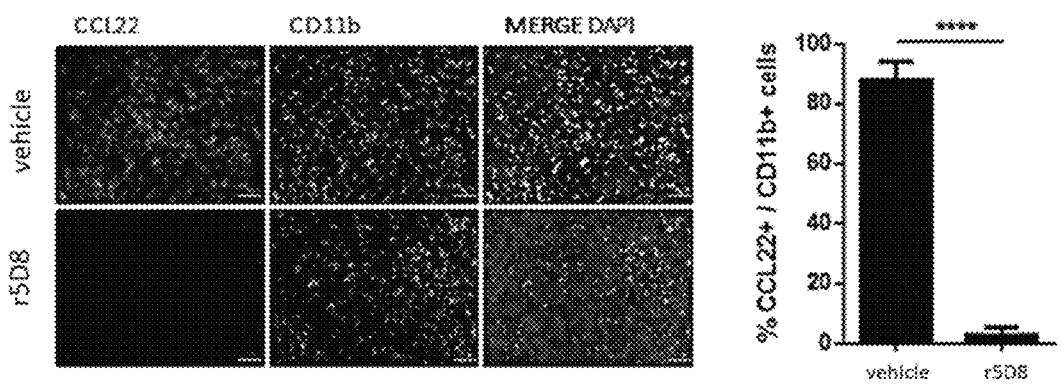
FIG. 10D shows reduction of macrophage infiltration to tumor sites in a syngeneic mouse model of colorectal cancer with a representative image and quantitation of CCL22+ cells.

In the U251 GBM orthotopic model, expression of CCL22, a marker of M2 polarized macrophages, was significantly decreased in tumors treated with r5D8 as shown in FIG. 10A. This finding was also confirmed in a physiologically relevant organotypic tissue slice culture model using r5D8 in which three patient samples showed a significant decrease in CCL22 and CD206 (MRC1) expression (also a marker of M2 macrophages) after treatment with as shown in FIG. 10B (compare upper left, control, to lower right, treated, for both MRC1 and CCL22). Furthermore, r5D8 also decreased CCL22$^+$M2 macrophages in syngeneic ID8 (FIG. 10C) and CT26 (FIG. 10D) tumors in immunocompetent mice.

Example 15—r5D8 Increases Non-Myeloid Effector Cells

Figure 11A:
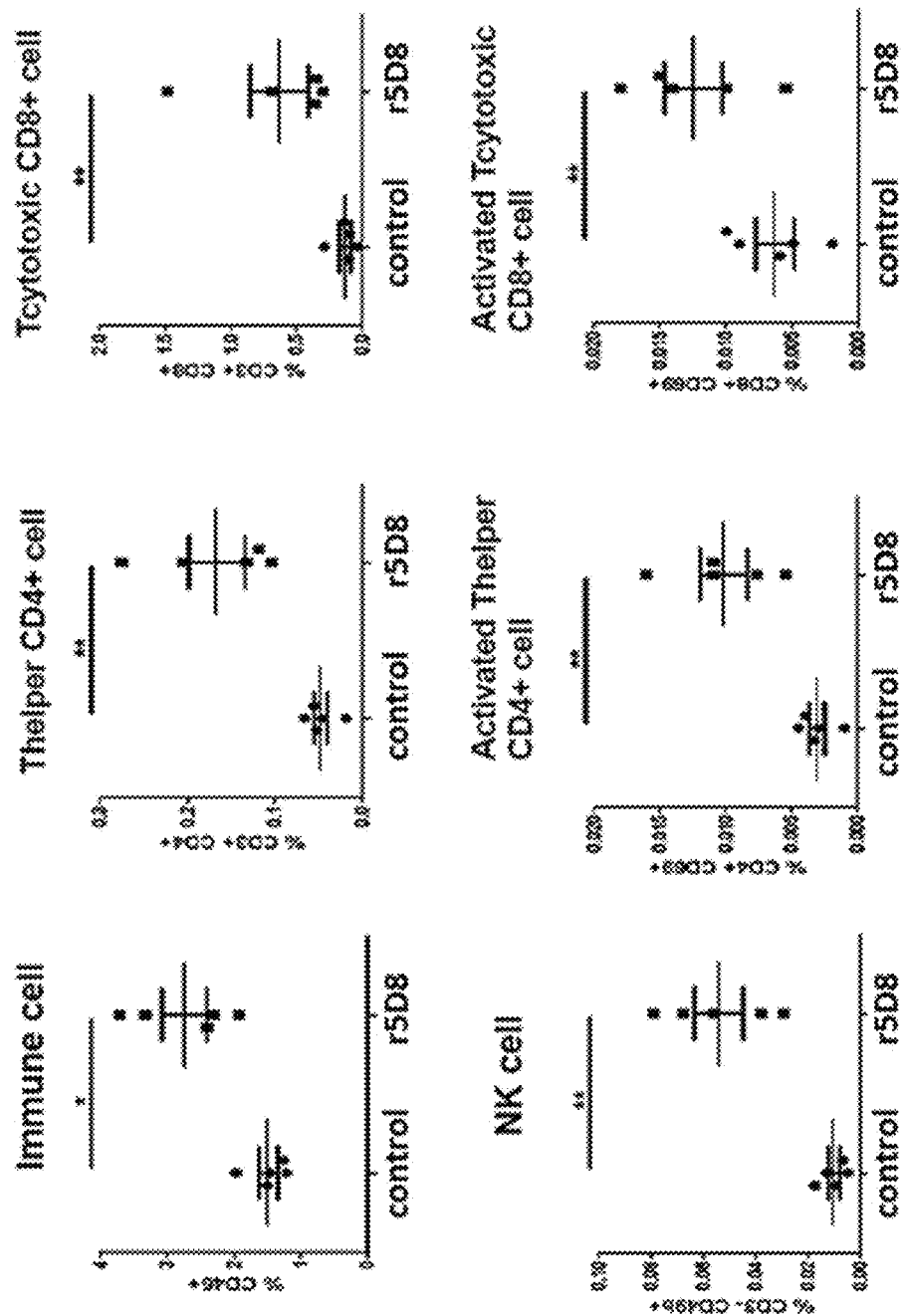
FIG. 11A shows increases in non-myeloid effector cells in a syngeneic mouse model of ovarian cancer after treatment with r5D8.
Figure 11B:
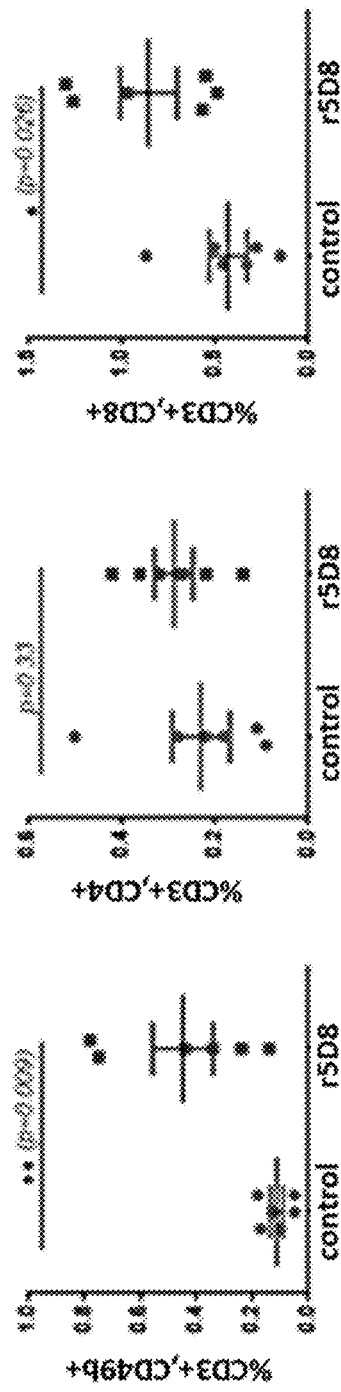
FIG. 11B shows increases in non-myeloid effector cells in a syngeneic mouse model of colorectal cancer after treatment with r5D8.
Figure 11C:
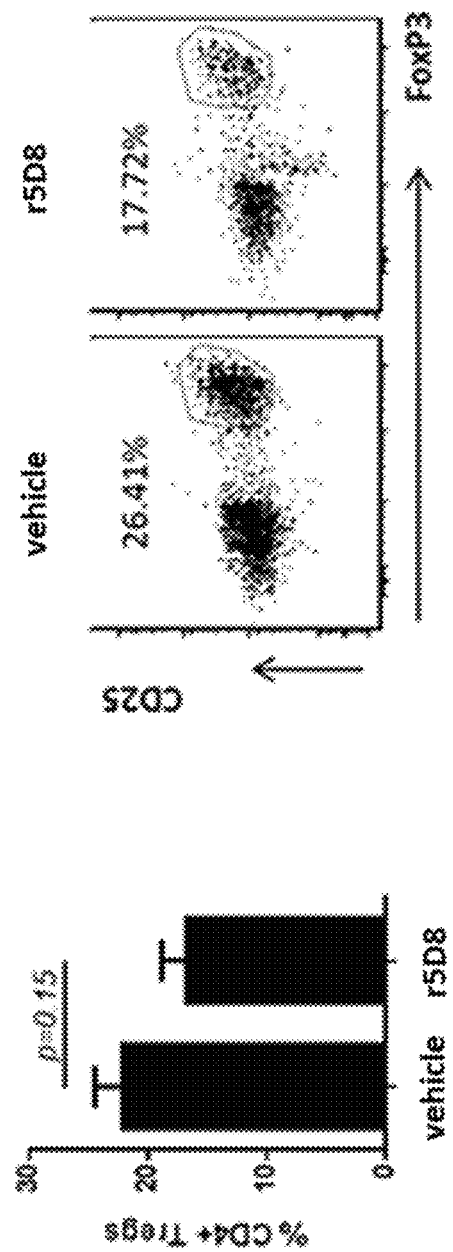
FIG. 11C shows decreases in percentage of CD4+$T_{REG}$ cells in a mouse model of NSCLC cancer after treatment with r5D8.
Figure 12:
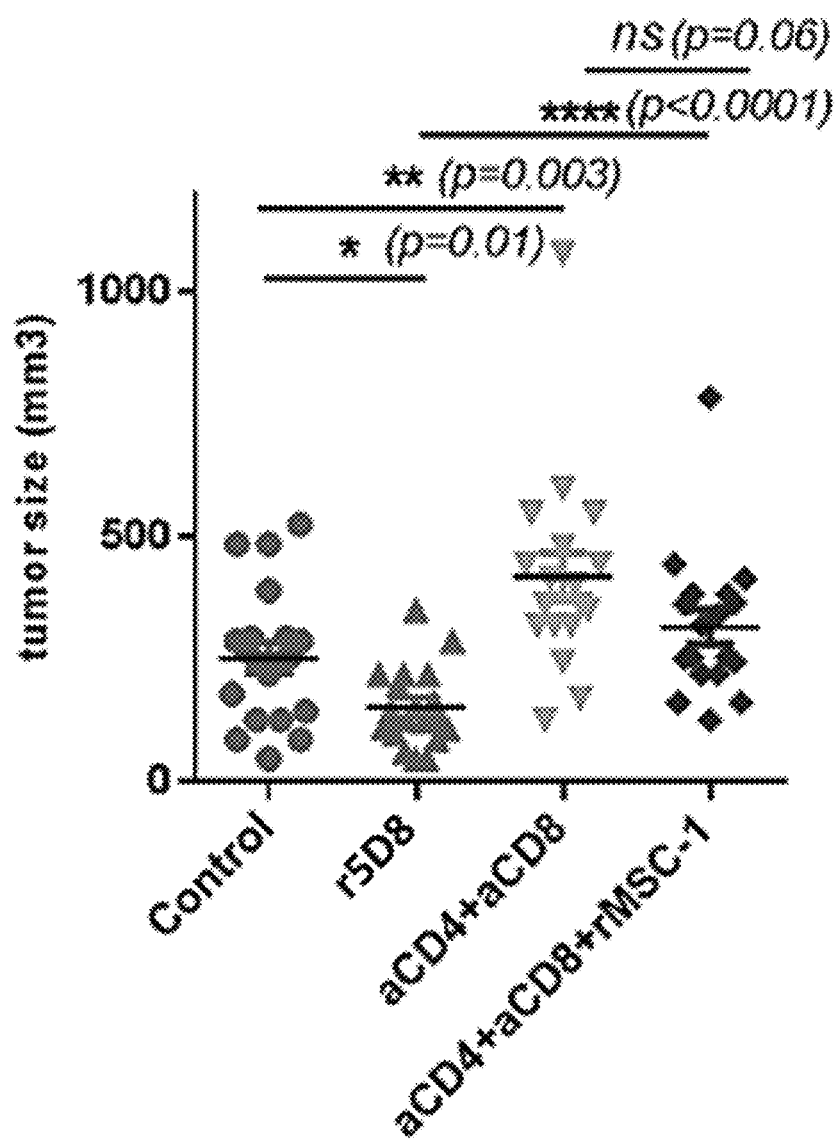
FIG. 12 shows data from mice bearing CT26 tumors treated twice weekly with PBS (control) or r5D8 administered intraperitoneally in the presence or absence of anti-CD4 and anti-CD8 depleting antibodies. The graph shows individual tumor measurements at d13 expressed as mean tumor volume+SEM. Statistical differences between groups was determined by unpaired non-parametric Mann-Whitney U-test. R5D8 inhibited the growth of CT26 tumors ($*p<0.05$). The tumor growth inhibition by r5D8 was significantly reduced in the presence of anti-CD4 and anti-CD8 depleting antibodies ($****p<0.0001$).

To investigate additional immune mechanisms, the effect of r5D8 on T cells and other non-myeloid immune effector cells within the tumor microenvironment were evaluated. In the ovarian orthotopic ID8 syngeneic model, r5D8 treatment resulted in an increase in intratumoral NK cells and an increase in total and activated CD4$^+$ and CD8$^+$T cells as shown in FIG. 11A. Similarly, in the colon syngeneic CT26 tumor model, r5D8 increased intratumoral NK cells, increased CD4+ and CD8+T cells and trended to decrease CD4+CD25+FoxP3+T-reg cells as shown in FIG. 11B. A trend for a decrease in CD4+CD25+FoxP3+T-reg cells was also observed in the syngeneic orthotopic KLN205 tumor model following r5D8treatment as shown in FIG. 11C. Consistent with a requirement for T cells to mediate efficacy, depletion of CD4+ and CD8+T cells in the CT26 model inhibited the anti-tumor efficacy of r5D8 as shown in FIG. 12.

Methods for T Cell Depletion

CT26 cells were cultured in RPMI culture medium (Gibco, Invitrogen), supplemented with 10% Fetal Bovine Serum (FBS [Gibco, Invitrogen]), 40 U/mL penicillin and 40 μg/mL streptomycin (PenStrep [Gibco, Invitrogen]) and 0.25 μg/mL Plasmocin (Invivogen). CT26 cells ($5\times10^5$) were collected, rinsed with PBS, centrifuged at 400 g for 5 minutes and resuspended in 100 μL PBS. Cells were kept on ice to avoid cell death. The CT26 cells were administered in both flanks to mice via subcutaneous injection using a 27 G syringe. Mice were treated twice weekly with r5D8 administered intraperitoneally as indicated in the study design. Vehicle control (PBS), rat r5D8, and/or anti-CD4 and anti-CD8 was administered to the mice via intraperitoneal injection (IP) twice weekly as stated in the study design. All antibody treatments were administered concomitantly.

Example 16—Crystal Structure of h5D8 in Complex with Human LIF

Figure 13A:
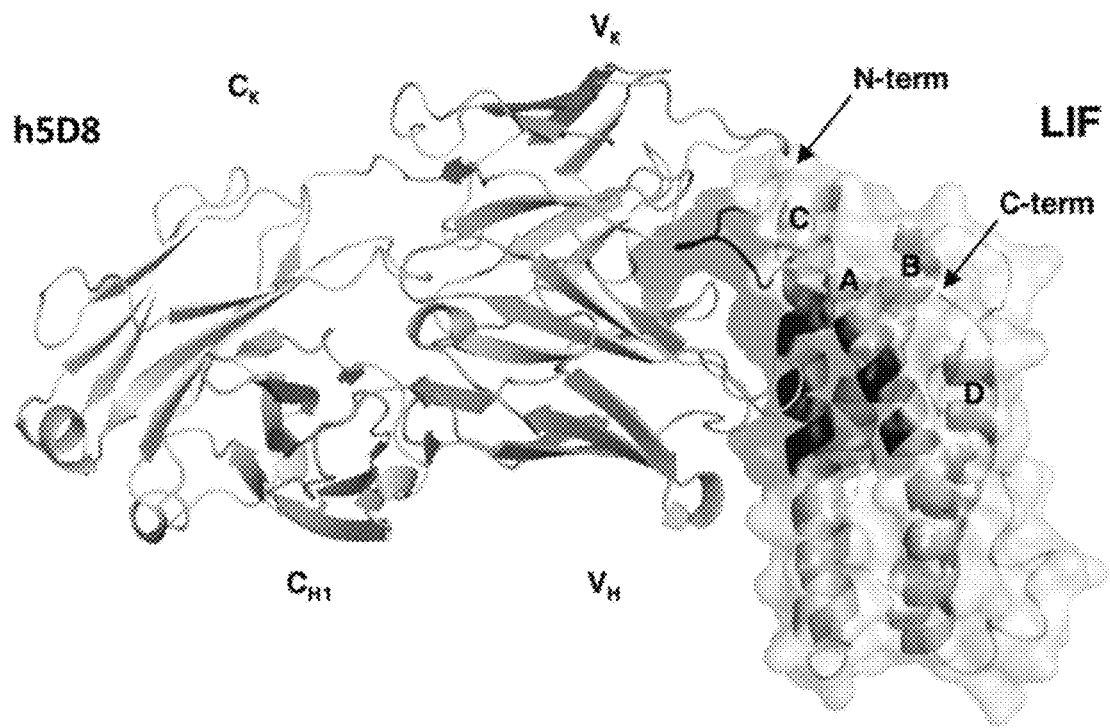
FIG. 13A illustrates Overview of the co-crystal structure of h5D8 Fab in complex with LIF. The gp130 interacting site is mapped on the surface of LIF (dark shaded)
Figure 13B:
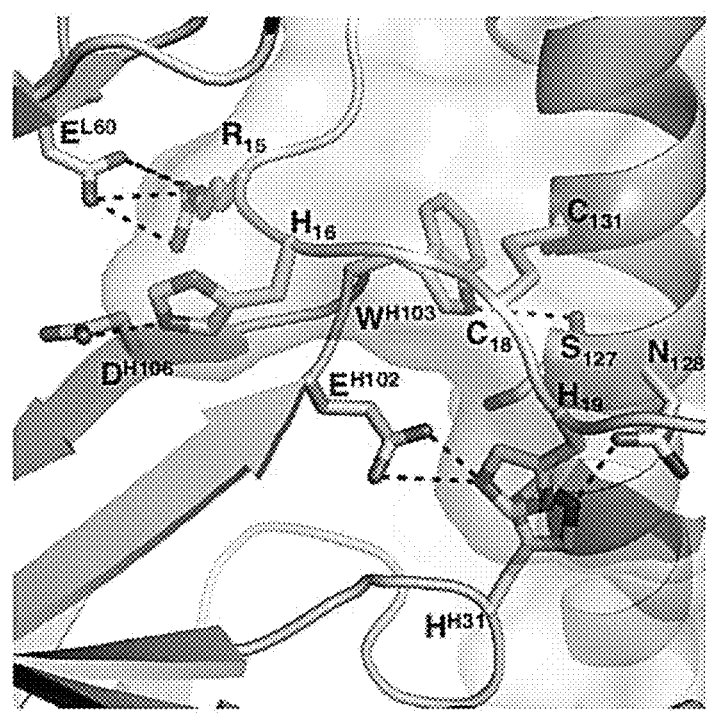
FIG. 13B illustrates detailed interactions between LIF and h5D8, showing residues forming salt bridges and h5D8 residues with buried surface areas greater than 100 Å$^2$.

The crystal structure of h5D8 was solved to a resolution of 3.1 angstroms in order to determine the epitope on LIF that h5D8 was bound to and to determine residues of h5D8 that participate in binding. The co-crystal structure revealed that the N-terminal loop of LIF is centrally positioned between the light and heavy chain variable regions of h5D8 (FIG. 13A). In addition, h5D8 interacts with residues on helix A and C of LIF, thereby forming a discontinuous and conformational epitope. Binding is driven by several salt-bridges, H-bonds and Van der Waals interactions (Table 7, FIG. 13B). The h5D8 epitope of LIF spans the region of interaction with gp130. See Boulanger, M. J., Bankovich, A. J., Kortemme, T., Baker, D. & Garcia, K. C. Convergent mechanisms for recognition of divergent cytokines by the shared signaling receptor gp130. *Molecular cell* 12, 577-589 (2003). The results are summarized below in Table 7 and depicted in FIG. 13.

TABLE 7

Summary of X-Ray crystal structure for h5D8 in complex with human LIF

| LIF Residue (epitope) | Interaction type | h5D8 Residue (paratope, Kabat numbering) |
|---|---|---|
| Ala13 | VDW | L-Tyr49, L-Asn53 |
| Ile14-O | HB | L-Ser50-OG |
| Ile | VDW | L-His30, L-Tyr32, L-Tyr49, L-Ser50 H-Trp97 |
| Arg15-NE | SB | L-Glu55-OE1, L-Glu55-OE2 |
| Arg15-NH1 | SB | L-Glu55-OE1, L-Glu55-OE2 |
| Arg15-NH2 | SB | L-Glu55-OE1, L-Glu55-OE2 |
| Arg15-O | HB | L-Asn34-ND2 |
| Arg15 | VDW | L-Asn34, L-Leu46, L-Tyr49, L-Glu55, L-Ser56 H-Glu96, H-Trp97, H-Asp98, H-Leu99, H-Asp101 |
| His16-NE2 | SB | H-Asp101-OD2 |
| His16 | VDW | L-Tyr32, L-Asn34, L-Met89 H-Trp95, H-Glu96, H-Trp97, H-Asp101 |

TABLE 7-continued

Summary of X-Ray crystal structure for h5D8 in complex with human LIF

| LIF Residue (epitope) | Interaction type | h5D8 Residue (paratope, Kabat numbering) |
|---|---|---|
| Pro17 | VDW | L-Tyr32, L-Ala91 H-Trp97 |
| Cys18 | VDW | L-Tyr32 H-Trp33, H-Trp97 |
| His19-NE2 | SB | H-Glu96-OE1, H-Glu96-OE2 |
| His19 | VDW | H-His31, H-Trp33, H-Glu96 |
| Asn20-OD1 | HB | H-Lys52-NZ |
| Asn20-ND2 | HB | H-Asp53-OD1 |
| Asn20 | VDW | H-Trp33, H-Lys52, H-Asp53 |
| Gln25-NE2 | HB | H-Asp53-OD2 |
| Gln25 | VDW | H-His31, H-Ser52C, H-Asp53 |
| Gln29 | VDW | H-His31 |
| Gln32 | VDW | H-Lys52B |
| Asp120-OD2 | HB | H-Ser30-OG |
| Asp120 | VDW | H-Thr28, H-Ser30 |
| Arg123-NE | HB | H-Thr28-0G |
| Arg123 | VDW | H-Thr28 |
| Gly124 | VDW | H-His31 |
| Leu125 | VDW | H-His31 |
| Ser127-OG | HB | H-Asp98-OD2 |
| Ser127-O | HB | H-Trp97-NE1 |
| Ser127 | VDW | H-His31, H-Trp97, H-Asp98 |
| Asn128-OD1 | HB | H-His31-NE2 |
| Asn128 | VDW | H-His31 |
| Leu130 | VDW | H-Trp97 |
| Cys131 | VDW | H-Trp97 |
| Cys134 | VDW | H-Trp97 |
| Ser135-O | HB | L-His30-NE2 |
| Ser135 | VDW | L-His30 |
| His138 | VDW | L-His30 |

VDW, van der Waals low energy binding;
HB, hydrogen bond (medium energy binding);
SB, salt bridge (high energy binding)

Methods

LIF was transiently expressed in HEK 293S (Gnt I$^{-/-}$) cells and purified using Ni-NTA affinity chromatography, followed by gel-filtration chromatography in 20 mM Tris pH 8.0 and 150 mM NaCl. The recombinant h5D8 Fab was transiently expressed in HEK 293F cells and purified using KappaSelect affinity chromatography, followed by cation exchange chromatography. Purified h5D8 Fab and LIF were mixed at a 1:2.5 molar ratio and incubated at room temperature for 30 min prior to deglycosylation using EndoH. Gel-filtration chromatography was subsequently used to purify the complex. The complex was concentrated to 20 mg/mL and set up for crystallization trials using sparse matrix screens. Crystals formed at 4° C. in a condition containing 19% (v/v) isopropanol, 19% (w/v) PEG 4000, 5% (v/v) glycerol, 0.095 M sodium citrate pH 5.6. The crystal diffracted to a resolution of 3.1 Å at the 08ID-1 beamline at the Canadian Light Source (CLS). Data were collected, processed and scaled using XDS as per Kabsch et al. Xds. *Acta crystallographica. Section D, Biological crystallography* 66, 125-132 (2010). Structures were determined by molecular replacement using Phaser as per McCoy et al. Phaser crystallographic software. *J Appl Crystallogr* 40, 658-674 (2007). Several iterations of model building and refinement were performed using Coot and phenix.refine until the structures converged to an acceptable $R_{work}$ and $R_{free}$. See Emsley et al. Features and development of Coot. *Acta crystallographica. Section D, Biological crystallography* 66, 486-501 (2010); and Adams, et al. PHENIX: a comprehensive Python-based system for macromolecular structure solution. *Acta crystallographica. Section D, Biological crystallography* 66, 213-221 (2010) respectively.

The figures were generated in PyMOL (The PyMOL Molecular Graphics System, Version 2.0 Schrödinger, LLC).

Example 17—h5D8 has High Specificity for LIF

We sought to test binding of h5D8 to other LIF family members to determine the binding specificity. Using Octet96 analysis h5D8 binding to human LIF is approximately 100-fold greater than binding to LIFs highest homology IL-6 family member Oncostatin M (OSM) when both proteins are produced in E. coli. When both proteins are produced in a mammalian system h5D8 exhibits no binding to OSM. Data are summarized in Table 8.

TABLE 8

Summary of h5D8 Affinity Measurements for Cytokines as Measured by Octet

|  | $K_D$ [M] | $k_{on}$ [1/MS] | $k_{dis}$ [1/s] |
|---|---|---|---|
| h5D8 + huLIF (E. coli) | 4.3E−10 +/− 2.0E−11 | 3.1E+05 +/− 3.1E+03 | 1.3E−04 +/− 5.8E−06 |
| h5D8 + huLIF (mammalian) | 1.3E−09 +/− 7.2E−11 | 1.2E+05 +/− 1.3E+03 | 1.5E−04 +/− 8.5E−06 |
| h5D8 + huOSM (E. coli) | 3.6E−08 +/− 1.4E−09 | 8.5E+04 +/− 3.1E+03 | 3.1E−03 +/− 4.1E−05 |
| h5D8 + huOSM (mammalian) | ND | ND | ND |
| h5D8 +huIL-6 (E. coli) | ND | ND | ND |

ND = no binding

Methods

Octet Binding Experiments: Reagents were used and prepared as per manufacturer's provided manual. A Basic Kinetics Experiment was performed using Octet Data Acquisition software ver. 9.0.0.26 as follows: Setup of sensors/program: i) Equilibration (60 seconds); ii) Loading (15 seconds); iii) Baseline (60 seconds); iv) Association (180 seconds); and v) Dissociation (600 seconds)

Octet Affinity of h5D8 for cytokines: A Basic Kinetics Experiment was performed using Octet Data Acquisition software ver. 9.0.0.26 as follows: Amine Reactive 2nd Generation Biosensors (AR2 G) were hydrated for a minimum of 15 minutes in water. Amine conjugation of h5D8 to the biosensors was performed according to ForteBio Technical Note 26 (please see References) using the Amine Coupling Second Generation Kit. Dip steps were as performed at 30° C., 1000 rpm as follows: i) 60 seconds Equilibration in water; ii) 300 seconds Activation in 20 mM ECD, 10 mM sulfo-NHS in water; iii) 600 second Immobilization of 10 µg/ml h5D8 in 10 mM Sodium Acetate, pH 6.0; iv) 300 seconds Quench in 1M Ethanolamine, pH 8.5; v) 120 seconds Baseline in water. Kinetics experiments were then performed with the following Dip and Read steps at 30° C., 1000 rpm: vi) 60 seconds Baseline in 1× kinetics buffer; vii) 180 seconds Association of appropriate serial dilutions of a cytokine in 1× kinetics buffer; viii) 300 seconds Dissociation in 1× kinetics buffer; ix) Three Regeneration/Neutralization cycles alternating between 10 mM glycine pH 2.0 and 1× kinetics buffer respectively (5 seconds in each for 3 cycles). Following regeneration, the biosensors were reused for subsequent binding analyses.

Human recombinant LIF produced from mammalian cells was from ACROBiosystems (LIF-H521b); human recombinant OSM produced in mammalian cells was from R & D (8475-OM/CF); and human recombinant OSM produced in E. coli cells was from R & D (295-OM-050/CF).

Example 18—Crystal Structure of h5D8 Fab

Five crystal structures of the h5D8 Fab under a wide spectrum of chemical conditions were determined. The high resolutions of these structures indicate that the conformations of CDR residues are associated with minor flexibility, and are highly similar in different chemical environments. A unique feature of this antibody is the presence of a non-canonical cysteine in position 100 of the variable heavy region. Structure analysis shows that the cysteine is unpaired and largely inaccessible to the solvent.

H5D8 Fab was obtained by papain digestion of its IgG, followed by purification using standard affinity, ion exchange and size chromatography techniques. Crystals were obtained using vapor diffusion methods and allowed to determine five crystal structures ranging between 1.65 Å to 2.0 Å in resolution. All structures were solved in the same crystallographic space group and with similar unit cell dimensions (P212121, a~53.8 Å, b~66.5 Å, c~143.3 Å), despite crystallization conditions ranging across five different pH levels: 5.6, 6.0, 6.5, 7.5 and 8.5. As such, these crystal structures allow for comparison of the three-dimensional disposition of h5D8 Fab unimpeded by crystal packing artefacts and across a wide spectrum of chemical conditions.

Figure 14A:
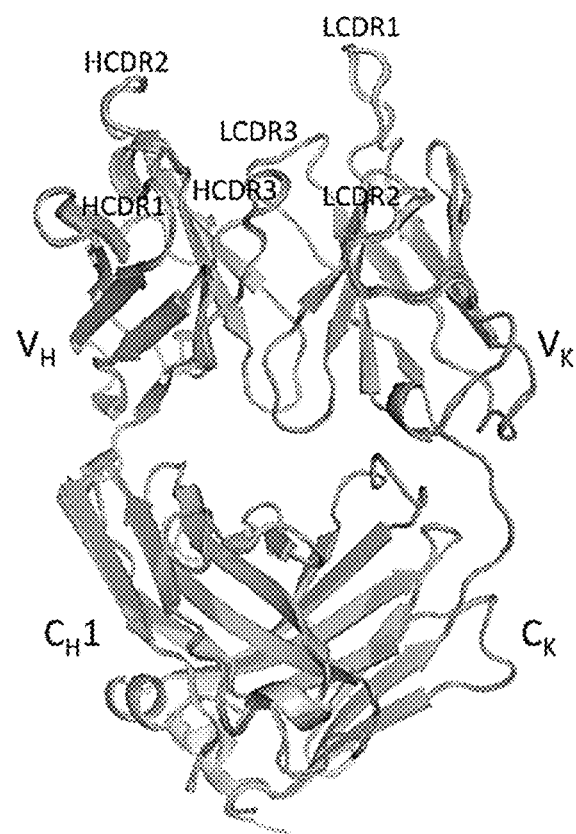
FIG. 14A illustrates superposition of the five h5D8 Fab crystal structures and indicates a high degree of similarity despite being crystallized in different chemical conditions.
Figure 14B:
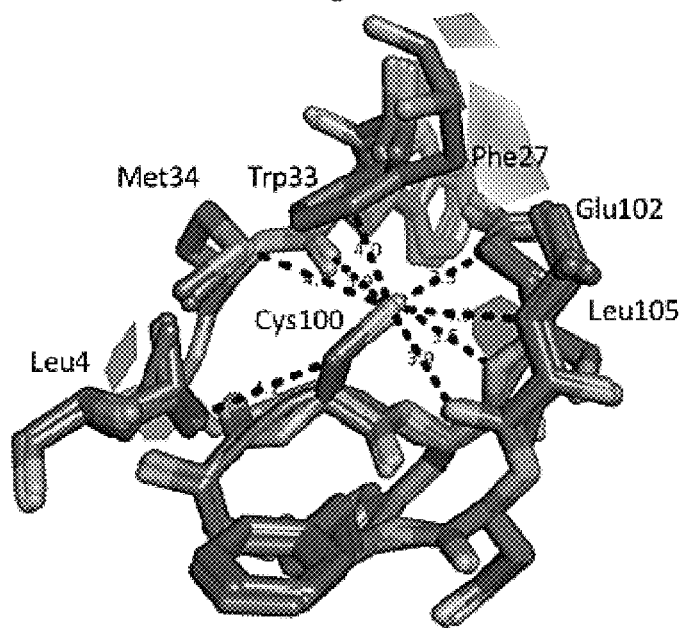
FIG. 14B illustrates an extensive network of van der Waals interactions mediated by unpaired Cys100. This residue is well-ordered, partakes in shaping the conformations of HCDR1 and HCDR3 and is not involved in undesired disulfide scrambling. Distances between residues are shown as dashed lines and labeled.

Electron density was observed for all complementarity determining region (CDR) residues, which were subsequently modeled. Noticeably, LCDR1 and HCDR2 adopted elongated conformations that together with shallow LCDR3 and HCDR3 regions formed a binding groove at the center of the paratope (FIG. 14A). The five structures were highly similar across all residues, with all-atoms root mean square deviations ranging between 0.197 Å and 0.327 Å (FIG. 14A). These results indicated that the conformations of CDR residues were maintained in various chemical environments, including pH levels ranging between 5.6 and 8.5 and ionic strengths ranging between 150 mM and 1 M. Analysis of the electrostatic surface of the h5D8 paratope revealed that positively and negatively charged regions equally contributed to hydrophilic properties, with no prevalent hydrophobic patches. h5D8 has the uncommon feature of a non-canonical cysteine at the base of HCDR3 (Cys100). In all five structures, this free cysteine is ordered and does not form any disulfide scrambles. Additionally, it is not modified by the addition of Cys (cysteinylation) or glutathione (glutathiolation) and makes van der Waals interactions (3.5-4.3 Å distances) with main chain and side chain atoms of Leu4, Phe27, Trp33, Met34, Glu102 and Leu105 of the heavy chain (FIG. 14B). Finally, Cys100 is a predominantly buried structural residue that appears to be involved in mediating the conformations of CDR1 and HCDR3. It is thus unlikely to have reactivity with other cysteines, as observed by a homogeneous disposition of this region in our five crystal structures.

Methods

H5D8-1 IgG was obtained from Catalent Biologics and was formulated in 25 mM histidine, 6% sucrose, 0.01% polysorbate 80, at pH 6.0. The formulated IgG was extensively buffer-exchanged into PBS using a 10K MWCO concentrator (Millipore) prior to digestion with 1:100 microgram papain (Sigma) for 1 hour at 37° C. in PBS, 1.25 mM EDTA, 10 mM cysteine. The papain-digested IgG was flown through a Protein A column (GE Healthcare) using an AKTA Start chromatography system (GE Healthcare). The Protein A flow-through, which contained the h5D8 Fab was recovered and buffer-exchanged into 20 mM sodium acetate, pH 5.6 using a 10K MWCO concentrator (Millipore). The resulting sample was loaded onto a Mono S cation exchange column (GE Healthcare) using an AKTA Pure chromatography system (GE Healthcare). Elution with a gradient of 1 M potassium chloride resulted in a predominant h5D8 Fab peak that was recovered, concentrated and purified to size homogeneity using a Superdex 200 Increase gel filtration column (GE Healthcare) in 20 mM Tris-HCl, 150 mM sodium chloride, at pH 8.0. The high purity of the h5D8 Fab was confirmed by SDS-PAGE under reducing and non-reducing conditions.

Purified h5D8 Fab was concentrated to 25 mg/mL using a 10K MWCO concentrator (Millipore). An Oryx 4 dispenser (Douglas Instruments) was used to set up vapor diffusion crystallization experiments with sparse matrix 96-conditions commercial screens JCSG TOP96 (Rigaku Reagents) and MCSG-1 (Anatrace) at 20° C. Crystals were obtained and harvested after four days in the following five crystallization conditions: 1) 0.085 M sodium citrate, 25.5% (w/v) PEG 4000, 0.17 M ammonium acetate, 15% (v/v) glycerol, pH 5.6; 2) 0.1 M IVIES, 20% (w/v) PEG 6000, 1 M lithium chloride, pH 6.0; 3) 0.1 M MES, 20% (w/v) PEG 4000, 0.6 M sodium chloride, pH 6.5; 4) 0.085 M sodium HEPES, 17% (w/v) PEG 4000, 8.5% (v/v) 2-propanol, 15% (v/v) glycerol, pH 7.5; and 5) 0.08 M Tris, 24% (w/v) PEG 4000, 0.16 M magnesium chloride, 20% (v/v) glycerol, pH 8.5. Prior to flash-freezing in liquid nitrogen, mother liquors containing the crystals were supplemented with 5-15% (v/v) glycerol or 10% (v/v) ethylene glycol, as required. Crystals were subjected to X-ray synchrotron radiation at the Advanced Photon Source, beamline 23-ID-D (Chicago, Ill.) and diffraction patterns were recorded on a Pilatus3 6M detector. Data were processed using XDS and structures were determined by molecular replacement using Phaser. Refinement was carried out in PHENIX with iterative model building in Coot. Figures were generated in PyMOL. All software were accessed through SBGrid.

Example 19—Mutations at Cysteine 100 of h5D8 Preserve Binding

Figure 15A:
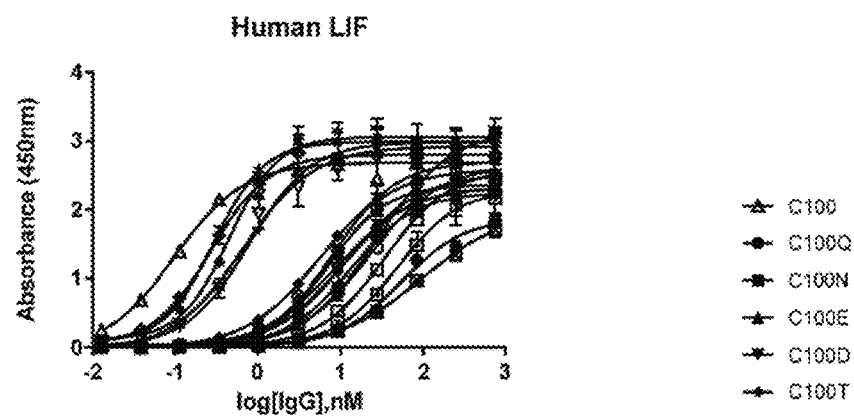
FIG. 15A illustrates binding of h5D8 C100 mutants to human LIF by ELISA.
Figure 15B:
FIG. 15B illustrates binding of h5D8 C100 mutants to mouse LIF by ELISA.

Analysis of h5D8 revealed a free cysteine residue at position 100 (C100) in the variable region of the heavy chain. H5D8 variants were generated by substituting C100 with each naturally occurring amino acid in order to characterize binding to and affinity for human and mouse LIF. Binding was characterized using ELISA and Octet assay. Results are summarized in Table 9. ELISA EC50 curves are shown in FIG. 15 (FIG. 15A human LIF and FIG. 15B Mouse LIF).

TABLE 9

Summary of affinities determined by Octet assay and EC50 determined by ELISA

| | Affinity/$k_D$ (M) | | Binding EC50 (nM) | |
|---|---|---|---|---|
| Mutation | human LIF | mouse LIF | human LIF | mouse LIF |
| C100 | <1.0E−12 ± 2.252E−11 | 9.946E−11 ± 8.272E−12 | 0.09878 | 0.1605 |
| C100S | 8.311E−10 ± 5.886E−11 | 2.793E−09 ± 5.925E−11 | n.d. | n.d. |
| C100Q | 3.87E−09 ± 1.55E−10 | 2.84E−09 ± 4.85E−11 | 10.18 | 26.33 |
| C100N | 5.59E−09 ± 1.01E−10 | 6.68E−09 ± 9.8E−11 | 13.18 | 45.87 |
| C100E | 2.67E−09 ± 4.64E−11 | 4.1E−09 ± 7.56E−11 | 7.179 | 25.3 |
| C100D | 2.02E−09 ± 8.08E−11 | 6.49E−09 ± 7.16E−11 | 11.89 | 22.88 |
| C100T | 4.36E−10 ± 2.1E−11 | 1.02E−09 ± 1.77E−11 | 5.575 | 8.753 |
| C100G | 2.49E−09 ± 4.2E−11 | 3.33E−09 ± 5.42E−11 | 21.94 | 40.17 |
| C100P | 2.74E−10 ± 2.97E−10 | <1.0E−12 ± 7.64E−10 | 34.44 | 101.9 |
| C100A | <1.0E−12 ± 2.713E−11 | <1.0E−12 ± 1.512E−11 | 0.6705 | 0.9532 |
| C100V | <1.0E−12 ± 1.805E−11 | <1.0E−12 ± 8.086E−12 | 0.2785 | 0.3647 |
| C100L | <1.0E−12 ± 1.963E−11 | 1.998E−10 ± 1.055E−11 | 0.454 | 0.547 |
| C100I | <1.0E−12 ± 1.424E−11 | 3.361E−11 ± 7.545E−12 | 0.299 | 0.3916 |
| C100M | 1.155E−09 ± 3.400E−11 | 2.676E−09 ± 2.449E−11 | 0.7852 | 1.563 |
| C100F | 4.376E−09 ± 1.127E−10 | 1.147E−08 ± 9.099E−11 | 8.932 | 21.53 |
| C100Y | 1.444E−08 ± 1.159E−09 | 2.514E−08 ± 2.047E−09 | n.d. | n.d. |
| C100W | 2.508E−08 ± 7.036E−09 | 4.819E−08 ± 4.388E−09 | n.d. | n.d. |
| C100H | 1.304E−10 ± 1.416E−10 | 4.284E−09 ± 1.231E−10 | 8.254 | n.d. |
| C100K | 7.477E−08 ± 1.581E−09 | 6.053E−08 ± 2.589E−09 | n.d. | n.d. |
| C100R | 1.455E−07 ± 6.964E−09 | 5.142E−08 ± 3.247E−09 | n.d. | n.d. |

Methods

ELISA: Binding of h5D8 C100 variants to human and mouse LIF was determined by ELISA. Recombinant human or mouse LIF protein was coated on Maxisorp 384-well plates at 1 ug/mL overnight at 4° C. Plates were blocked with 1x blocking buffer for 2 hours at room temperature. Titrations of each h5D8 C100 variants were added and allowed to bind for 1 hour at room temperature. Plates were washed three times with PBS+0.05% Tween-20. HRP-conjugated anti-human IgG was added and allowed to bind for 30 min at room temperature. Plates were washed three times with PBS+0.05% Tween-20 and developed using 1xTMB substrate. The reaction was stopped with 1M HCl and absorbance at 450 nm was measured. Generation of figures and non-linear regression analysis was performed using Graphpad Prism.

Octet RED96: The affinity of h5D8 C100 variants to human and mouse LIF was determined by BLI using the Octet RED96 system. h5D8 C100 variants were loaded onto Anti-Human Fc biosensors at 7.5 ug/mL following a 30 second baseline in 1×kinetics buffer. Titrations of human or mouse LIF protein were associated to the loaded biosensors for 90 seconds and allowed to dissociate in 1× kinetics buffer for 300 seconds. KDs were calculated by the data analysis software using a 1:1 global fit model.

Example 20—h5D8 Blocks Binding of LIF to Gp130 In Vitro

Figure 16A:
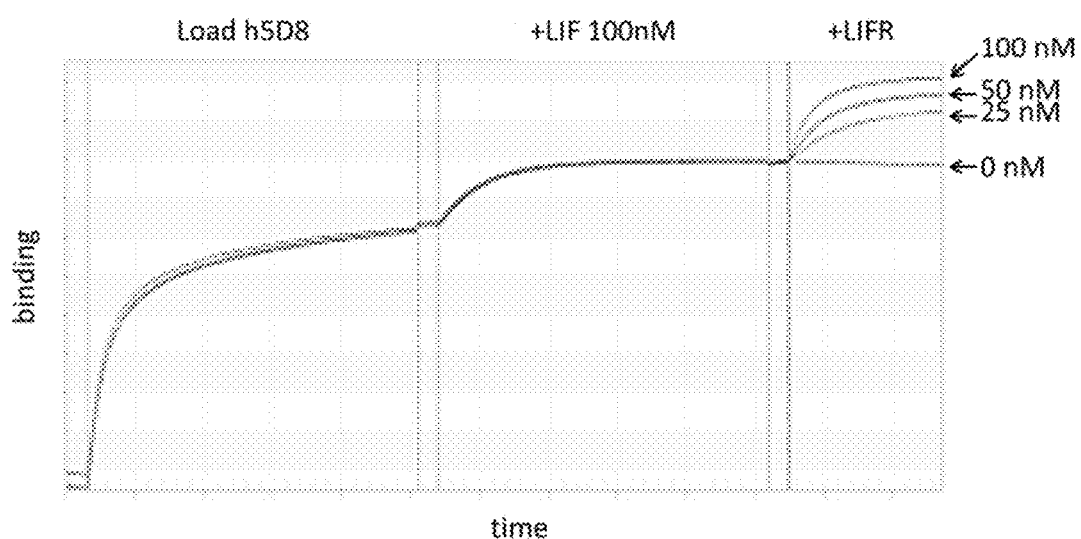
FIG. 16A illustrates that h5D8 does not block binding between LIF and LIFR by Octet. Sequential binding of h5D8 to LIF followed by LIFR.

To determine whether h5D8 prevented LIF from binding to LIFR, a molecular binding assay using the Octet RED 96 platform was performed. H5D8 was loaded onto AHC biosensors by anti-human Fc capture. Then, the biosensors were dipped in LIF and, as expected, association was observed (FIG. 16A, middle third). Subsequently, the biosensors were dipped in different concentrations of LIFR. A dose-dependent association was observed (FIG. 16A, right third). The control experiment demonstrated that this association was LIF-specific (not shown), and not due to a non-specific interaction of LIFR with h5D8 or with the biosensors.

Figure 16B:
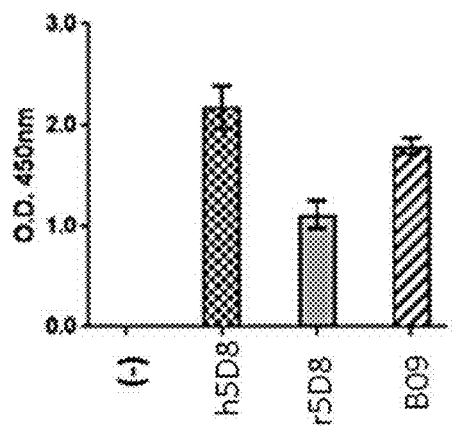
FIG. 16B and FIG. 16C illustrate ELISA analysis of LIF/mAb complexes binding to immobilized LIFR or gp130. Signals of species-specific peroxidase conjugated anti-IgG antibodies (anti-human for (−) and h5D8, anti-rat for r5d8 and B09) detecting the antibody portion of mAb/LIF complexes binding immobilized LIFR (FIG. 16B) or gp130 (FIG. 16C) coated plates.
Figure 16C:
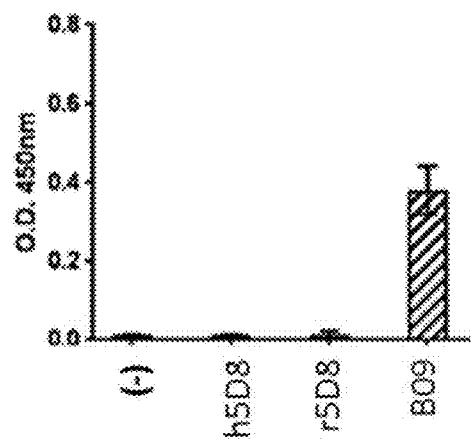

To further characterize the binding of h5D8 and LIF, a series of ELISA binding experiments was conducted. H5D8 and LIF were pre-incubated and were then introduced to plates coated with either recombinant human LIFR (hLIFR) or gp130. The lack of binding between the h5D8/LIF complex and the coated substrate would indicate that h5D8 in some way disrupted the binding of LIF to the receptor. Additionally, control antibodies that either did not bind LIF (isotype control, indicated by (−)) or that bind LIF at known binding sites (B09 does not compete with either gp130 or LIFR for LIF binding; r5D8 is the rat parental version of h5D8) were also used. The ELISA results demonstrated that the h5D8/LIF complex was able to bind hLIFR (as was r5D8/LIF complex), indicating that these antibodies did not prevent the LIF/LIFR association (FIG. 16A). In contrast, the h5D8/LIF complex (and a r5D8/LIF complex) was not able to bind recombinant human gp130 (FIG. 16B). This indicates that the gp130 binding site of LIF was affected when LIF was bound to h5D8.

Example 21—LIF and LIFR Expression in Human Tissues

Figure 17A:
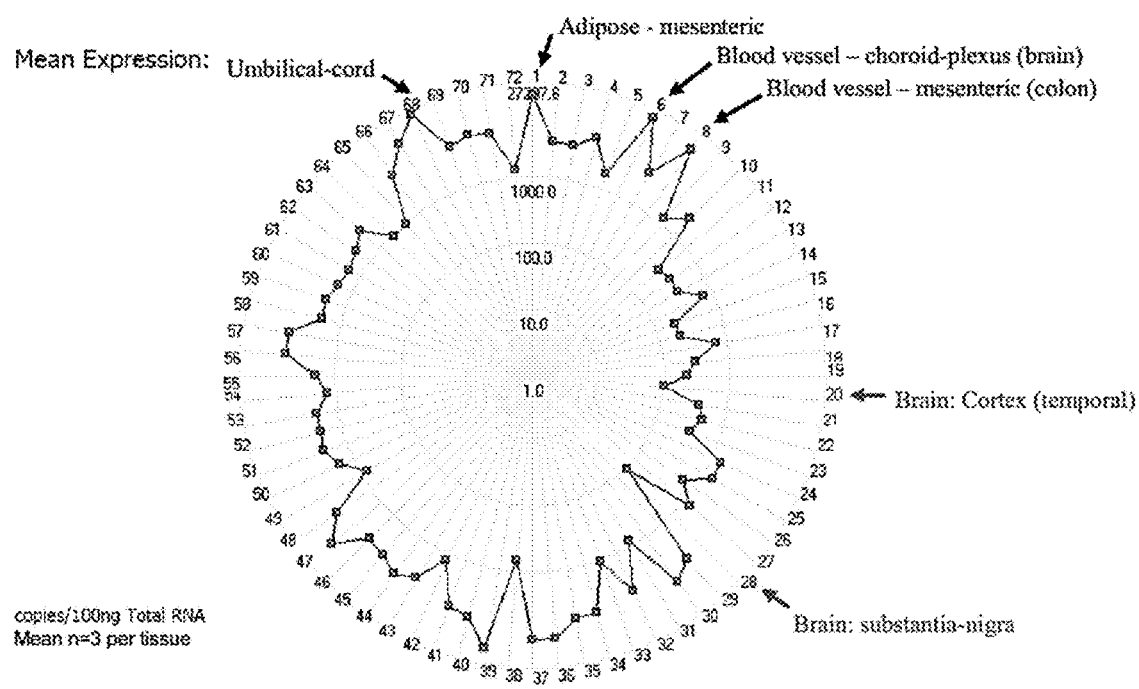
FIG. 17A and FIG. 17B illustrate mRNA expression of LIF (FIG. 16A) or LIFR (FIG. 16B) in 72 different human tissues.
Figure 17B:
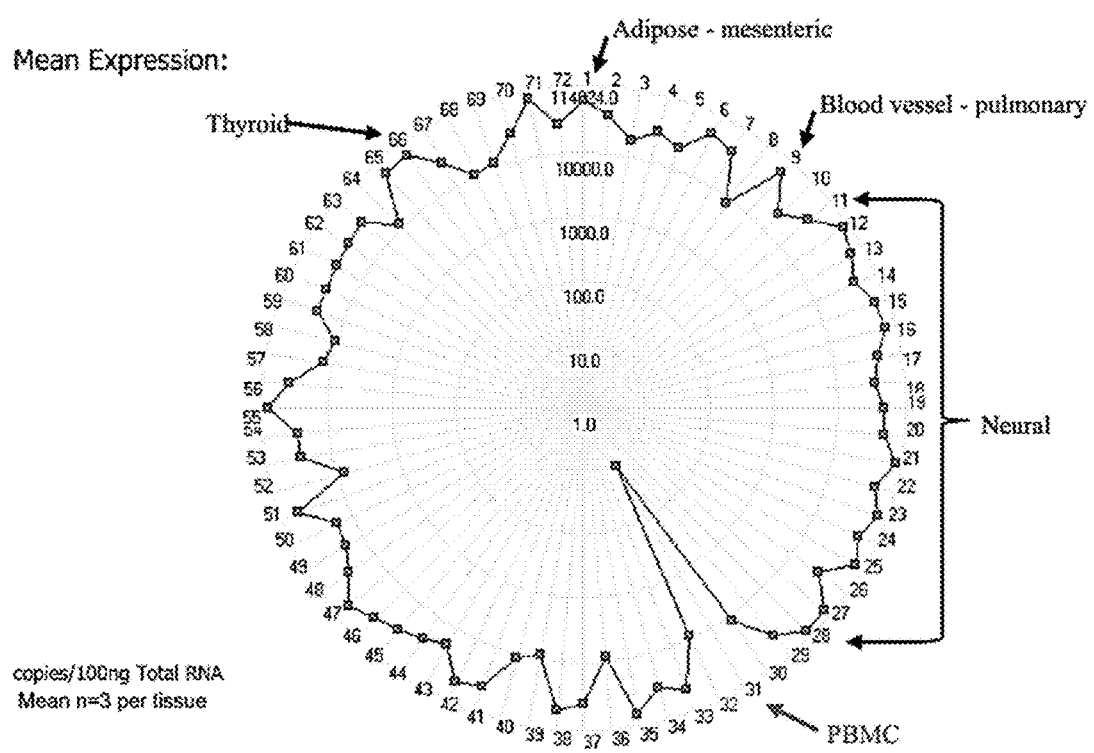

Quantitative real-time PCR was performed on many different types of human tissue in order to determine expression levels of LIF and LIFR. The mean expression levels shown in FIGS. 17A and 17B are given as copies per 100 ng of total RNA. Most tissues expressed at least 100 copies per 100 ng of total RNA. LIF mRNA expression was highest in human adipose tissue (mesenteric-ileum [1]), blood-vessel tissue (choroid-plexus [6] and mesenteric [8]) and umbilical cord [68] tissue and lowest in brain tissue (cortex [20] and substantia-nigra [28]). LIFR mRNA expression was highest in human adipose tissue (mesenteric-ileum [1]), blood vessel tissue (pulmonary [9]), brain tissue [11-28] and thyroid [66] tissue and was lowest in PBMCs [31]. LIF and LIFR mRNA expression levels in cynomolgus tissues were similar to those observed in human tissues, wherein LIF expression was high in adipose tissue and LIFR expression was high in adipose tissue and low in PBMCs (data not shown).

The tissue numbering for FIG. 17A and FIG. 17B is: 1—adipose (mesenteric-ileum); 2—adrenal gland; 3—bladder; 4—bladder (trigone); 5—blood-vessel (cerebral: middle-cerebral-artery); 6—blood vessel (choroid-plexus); 7—blood vessel (coronary artery); 8—blood vessel (mesenteric (colon)); 9—blood vessel (pulmonary); 10—blood vessel (renal); 11—brain (amygdala); 12—brain (caudate); 13—brain (cerebellum); 14 brain—(cortex: cingulate-anterior); 15—brain (cortex: cingulate-posterior); 16—brain (cortex: frontal-lateral); 17—brain (cortex: frontal-medial); 18—brain (cortex: occipital); 19—brain (cortex: parietal); 20—brain (cortex: temporal); 21—brain (dorsal-raphe-nucleus); 22—brain (hippocampus); 23—brain (hypothalamus: anterior); 24—brain (hypothalamus: posterior); 25—brain (locus coeruleus); 26—brain (medulla oblongata); 27—brain (nucleus accumbens); 28—brain (substantia nigra); 29—breast; 30—caecum; 31—peripheral blood mononuclear cell (PBMCs); 32—colon; 33—dorsal root ganlia (DRG); 34—duodenum; 35—fallopian tube; 36—gallbladder; 37—heart (left atrium); 38—heart (left ventricle); 39—ileum; 40—jejunum; 41—kidney (cortex); 42—kidney (medulla); 43—kidney (pelvis); 44—liver (parenchyma); 45—liver (bronchus: primary); 46—liver (bronchus: tertiary); 47—lung (parenchyma); 48—lymph gland (tonsil); 49—muscle (skeletal); 50—esophagus; 51—ovary; 52—pancreas; 53—pineal gland; 54—pituitary gland; 55—placenta; 56—prostate; 57—rectum; 58—skin (foreskin); 69—spinal cord; 60—spleen (parenchyma); 61—stomach (antrum); 62—stomach (body); 63—stomach (fundus); 64—stomach (pyloric canal); 65—testis; 66—thyroid gland; 67—trachea; 68—umbilical cord; 69—ureter; 70—uterus (cervix); 71—uterus (myometrium); and 72—vas deferens.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

| SEQUENCES | |
|---|---|
| SEQ ID NO | Sequence |
| 1 | GFTFSHAWMH |
| 2 | GFTFSHAW |
| 3 | HAWMH |
| 4 | GFTFSNAWMH |
| 5 | GFTFSNAW |

| SEQ ID NO | Sequence |
|---|---|
| 6 | NAWMH |
| 7 | SKFMY |
| 8 | SNFIH |
| 9 | QIKAKSDDYATYYAESVKG |
| 10 | IKAKSDDYAT |
| 11 | QIKDKSDNYATYYAESVKG |
| 12 | IKDKSDNYAT |
| 13 | WIYPGDGDTEYNQKFSE |
| 14 | WIYPGDGDIEYNQKFIG |
| 15 | TCWEWDLDF |
| 16 | WEWDLDF |
| 17 | TCWEWYLDF |
| 18 | WEWYLDF |
| 19 | RDYHSSHFAY |
| 20 | HYSSSMDA |
| 21 | RSSQSLLDSDGHTYLN |
| 22 | QSLLDSDGHTY |
| 23 | RSSQSLLHNNGNTYLS |
| 24 | RSSQSLVHSNGNTFLS |
| 25 | SVSNLES |
| 26 | SVS |
| 27 | QVSNRFS |
| 28 | KVSNRFS |
| 29 | MQATHAPPYT |
| 30 | GQGTQYPYT |
| 31 | GQGTQYPFT |
| 32 | SGYYWN |
| 33 | TAGMQ |
| 34 | CISYDGRNNYNPSLKN |
| 35 | WINTQSGEPQYVDDFRG |
| 36 | RYRYYNYGSYYAVDY |
| 37 | WALYSEYDVMDY |
| 38 | RASENIDGYLE |
| 39 | KASENVDSYVS |
| 40 | AATLLAD |
| 41 | GASNRYT |
| 42 | QHYYNTPLT |
| 43 | GQSYRYPPT |
| 44 | EVQLVESGGGLVKPGGSLKLSCAAS |
| 45 | QVQLQESGGGLVKPGGSLRLSCAAS |
| 46 | EVQLVESGGGVVQPGRSLRLSCAAS |
| 47 | EVQLMESGGGLVKPGGSLRLSCATS |
| 48 | WVRQAPGKGLEWVA |
| 49 | WVRQAPGKGLEWVG |
| 50 | RFTISRDDSKNTLYLQMNSLKTEDTAVYYC |
| 51 | RFSISRDNAKNSLYLQMNSLRVEDTVVYYC |
| 52 | RFTISRDDSKSTLFLQMNNLKTEDTAVYYC |
| 53 | WGQGTLVTVSS |
| 54 | WGQGTMVTVSS |
| 55 | WGQGTTVTVSS |
| 56 | DVVMTQSPLSLPVTLGQPASISC |
| 57 | DIVMTQTPLSSPVTLGQPASISC |
| 58 | DIVMTQTPLSLSVTPGQPASISC |
| 59 | DVVMTQSPLSQPVTLGQPASISC |
| 60 | WFQQRPGQSPRRLIY |
| 61 | WLQQRPGQPPRLLIY |
| 62 | WLLQKPGQPPQLLIY |
| 63 | WLQQRPGQSPRRLIY |
| 64 | GVPDRFSGSGSGTDFTLKISRVEAEDVGLYYC |
| 65 | GVPDRFSGSGAGTDFTLKISRVEAEDVGVYYC |
| 66 | GVPNRFSGSGSGTDFTLKISRVEAEDVGLYYC |
| 67 | GVPDRFNGSGSGTDFTLSISRVEAEDVGVYYC |
| 68 | FGQGTKLEIK |
| 69 | FGGGTKVEIK |
| 70 | FGQGTKVEIK |
| 71 | EVQLVESGGGLVKPGGSLKLSCAASGFTFSHAWMHWVRQAPGKGLEWVAQIKAKSDDYATYYAESVKGRFTISRDDSKNTLYLQMNSLKTEDTAVYYCTCWEWDLDFWGQGTLVTVSS |
| 72 | QVQLQESGGGLVKPGGSLRLSCAASGFTFSHAWMHWVRQAPGKGLEWVGQIKAKSDDYATYYAESVKGRFTISRDDSKNTLYLQMNSLKTEDTAVYYCTCWEWDLDFWGQGTMVTVSS |
| 73 | EVQLVESGGGVVQPGRSLRLSCAASGFTFSHAWMHWVRQAPGKGLEWVAQIKAKSDDYATYYAESVKGRFSISRDNAKNSLYLQMNSLRVEDTVVYYCTCWEWDLDFWGQGTTVTVSS |
| 74 | EVQLMESGGGLVKPGGSLRLSCATSGFTFSHAWMHWVRQAPGKGLEWVGQIKAKSDDYATYYAESVKGRFTISRDDSKSTLFLQMNNLKTEDTAVYYCTCWEWDLDFWGQGTLVTVSS |

| SEQ ID NO | Sequence |
|---|---|
| 75 | DVVMTQSPLSLPVTLGQPASISCRSSQSLLDSDGHTYLNWFQQRPGQSPRRLIYSVSNLESGVPDRFSGSGSGTDFTLKISRVEAEDVGLYYCMQATHAPPYTFGQGTKLEIK |
| 76 | DIVMTQTPLSSPVTLGQPASISCRSSQSLLDSDGHTYLNWLQQRPGQPPRLLIYSVSNLESGVPDRFSGSGAGTDFTLKISRVEAEDVGVYYCMQATHAPPYTFGQGTKLEIK |
| 77 | DIVMTQTPLSLSVTPGQPASISCRSSQSLLDSDGHTYLNWLLQKPGQPPQLLIYSVSNLESGVPNRFSGSGSGTDFTLKISRVEAEDVGLYYCMQATHAPPYTFGGGTKVEIK |
| 78 | DVVMTQSPLSQPVTLGQPASISCRSSQSLLDSDGHTYLNWLQQRPGQSPRRLIYSVSNLESGVPDRFNGSGSGTDFTLSISRVEAEDVGVYYCMQATHAPPYTFGQGTKVEIK |
| 79 | MGWTLVFLFLLSVTAGVHSEVQLVESGGGLVKPGGSLKLSCAASGFTFSHAWMHWVRQAPGKGLEWVAQIKAKSDDYATYYAESVKGRFTISRDDSKNTLYLQMNSLKTEDTAVYYCTCWEWDLDFWGQGTLVTVSSASTKGPSVFPLAPSSKSTSGGTAALGCLVKDYFPEPVTVSWNSNGALTSGVHTFPAVLQSSGLYSLSSVVTVPSSSLGTQTYICNVHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK |
| 80 | MGWTLVFLFLLSVTAGVHSQVQLQESGGGLVKPGGSLRLSCAASGFTFSHAWMHWVRQAPGKGLEWVGQIKAKSDDYATYYAESVKGRFTISRDDSKNTLYLQMNSLKTEDTAVYYCTCWEWDLDFWGQGTMVTVSSASTKGPSVFPLAPSSKSTSGGTAALGCLVKDYFPEPVTVSWNSGALTSGVHTFPAVLQSSGLYSLSSVVTVPSSSLGTQTYICNVHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK |
| 81 | MGWTLVFLFLLSVTAGVHSEVQLVESGGGVVQPGRSLRLSCAASGFTFSHAWMHWVRQAPGKGLEWVAQIKAKSDDYATYYAESVKGRFSISRDNAKNSLYLQMNSLRVEDTVVYYCTCWEWDLDFWGQGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK |
| 82 | MGWTLVFLFLLSVTAGVHSEVQLMESGGGLVKPGGSLRLSCATSGFTFSHAWMHWVRQAPGKGLEWVGQIKAKSDDYATYYAESVKGRFTISRDDSKSTLFLQMNNLKTEDTAVYYCTCWEWDLDFWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK |
| 83 | MVSSAQFLGLLLLCFQGTRCDVVMTQSPLSLPVTLGQPASISCRSSQSLLDSDGHTYLNWFQQRPGQSPRRLIYSVSNLESGVPDRFSGSGSGTDFTLKISRVEAEDVGLYYCMQATHAPPYTFGQGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| 84 | MVSSAQFLGLLLLCFQGTRCDIVMTQTPLSSPVTLGQPASISCRSSQSLLDSDGHTYLNWLQQRPGQPPRLLIYSVSNLESGVPDRFSGSGAGTDFTLKISRVEAEDVGVYYCMQATHAPPYTFGQGTKLEIKRTVAAPSVFIFPPSDEQLKSGTASVVCLLNNFYPREAKVQWKVDNALQSGNPSQESVTEQDSKDSTYSLSSTLTLSKADYEKHKVYACEVTHQGLSSVTKSFNRGEC |
| 85 | MVSSAQFLGLLLLCFQGTRCDIVMTQTPLSLSVTPGQPASISCRSSQSLLDSDGHTYLNWLLQKPGQPPQLLIYSVSNLESGVPNRFSGSGSGTDFTLKISRVEAEDVGLYYCMQATHAPPYTFGGGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| 86 | MVSSAQFLGLLLLCFQGTRCDVVMTQSPLSQPVTLGQPASISCRSSQSLLDSDGHTYLNWLQQRPGQSPRRLIYSVSNLESGVPDRFSGSGSGTDFTLSISRVEAEDVGVYYCMQATHAPPYTFGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| 87 | EVQLVESGGGLVKPGGSLKLSCAASGFTFSHAWMHWVRQAPGKGLEWVGQIKAKSDDYATYYAESVKGRFTISRDDSKNTLYLQMNSLKTEDTAVYYCTCWEWDLDFWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK |
| 88 | QVQLQESGGGLVKPGGSLRLSCAASGFTFSHAWMHWVRQAPGKGLEWVGQIKAKSDDYATYYAESVKGRFTISRDDSKNTLYLQMNSLKTEDTAVYYCTCWEWDLDFWGQGTMVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK |
| 89 | EVQLVESGGGVVQPGRSLRLSCAASGFTFSHAWMHWVRQAPGKGLEWVAQIKAKSDDYATYYAESVKGRFSISRDNAKNSLYLQMNSLRVEDTVVYYCTCWEWDLDFWGQGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK |
| 90 | EVQLMESGGGLVKPGGSLRLSCATSGFTFSHAWMHWVRQAPGKGLEWVGQIKAKSDDYATYYAESVKGRFTISRDDSKSTLFLQMNNLKTEDTAVYYCTCWEWDLDFWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK |
| 91 | DVVMTQSPLSLPVTLGQPASISCRSSQSLLDSDGHTYLNWFQQRPGQSPRRLIYSVSNLESGVPDRFSGSGSGTDFTLKISRVEAEDVGLYYCMQATHAPPYTFGQGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |

SEQUENCES

SEQ ID NO 92
DIVMTQTPLSSPVTLGQPASISCRSSQSLLDSDGHTYLNWLQQRP
GQPPRLLIYSVSNLESGVPDRFSGSGAGTDFTLKISRVEAEDVGV
YYCMQATHAPPYTFGQGTKLEIKRTVAAPSVFIFPPSDEQLKSGT
ASVVCLLNNFYPREAKVQWKVDNALQSGNSQESVTEQDSKDSTYS
LSSTLTLSKADYEKHKVYACEVTHQGLSSPVTKSFNRGEC

SEQ ID NO 93
DIVMTQTPLSLSVTPGQPASISCRSSQSLLDSDGHTYLNWLLQKP
GQPPQLLIYSVSNLESGVPNRFSGSGSGTDFTLKISRVEAEDVGL
YYCMQATHAPPYTFGGGTKVEIKRTVAAPSVFIFPPSDEQLKSGT
ASVVCLLNNFYPREAKVQWKVDNALQSGNSQESVTEQDSKDSTYS
LSSTLTLSKADYEKHKVYACEVTHQGLSSPVTKSFNRGEC

SEQ ID NO 94
DVVMTQSPLSQPVTLGQPASISCRSSQSLLDSDGHTYLNWLQQRP
GQSPRRLIYSVSNLESGVPDRFSGSGSGTDFTLSISRVEAEDVGV
YYCMQATHAPPYTFGQGTKVEIKRTVAAPSVFIFPPSDEQLKSGT
ASVVCLLNNFYPREAKVQWKVDNALQSGNSQESVTEQDSKDSTYS
LSSTLTLSKADYEKHKVYACEVTHQGLSSPVTKSFNRGEC

SEQ ID NO 95
TSWEWDLDF

SEQ ID NO 96
QVQLQESGGGLVKPGGSLRLSCAASGFTFSHAWMHWVRQAPGKGL
EWVGQIKAKSDDYATYYAESVKGRFTISRDDSKNTLYLQMNSLKT
EDTAVYYCTSWEWDLDFWGQGTMVTVSS

SEQ ID NO 97
QVQLQESGGGLVKPGGSLRLSCAASGFTFSHAWMHWVRQAPGKGL
EWVGQIKAKSDDYATYYAESVKGRFTISRDDSKNTLYLQMNSLKT
EDTAVYYCTSWEWDLDFWGQGTMVTVSSASTKGPSVFPLAPSSKS
TSGGTAALGCLVKDYFPEPVTVSWNSGALTSGVHTFPAVLQSSGL
YSLSSVVTVPSSSLGTQTYICNVNHKPSNTKVDKKVEPKSCDKTH
TCPPCPAPELLGGPSVFLFPPKPKDTLMISRTPEVTCVVVDVSHE
DPEVKFNWYVDGVEVHNAKTKPREEQYNSTYRVVSVLTVLHQDWL
NGKEYKCKVSNKALPAPIEKTISKAKGQPREPQVYTLPPSREEMT
KNQVSLTCLVKGFYPSDIAVEWESNGQPENNYKTTPPVLDSDGSF
FLYSKLTVDKSRWQQGNVFSCSVMHEALHNHYTQKSLSLSPGK

SEQ ID NO 98
SPLPITPVNATCAIRHPCHNNLMNQIRSLAQLNGSANALFILYY
TAQGEPFPNNLDKLCGPNVTDFPPFHANGTEKAKLVELYRIVVYL
GTSLGNITRDQKILNPSALSLHSKLNATADILRGLLSNVLCRLCS
KYHVGHVDVTYGPDTSGKDVFQKKKLGCQLLGKYKQIIAVLAQAF

---

What is claimed is:

1. A recombinant antibody that specifically binds Leukemia Inhibitory Factor (LIF), the antibody comprising:
   a) a heavy chain complementarity determining region 1 (VH-CDR1) comprising the amino acid sequence set forth in SEQ ID NO: 2 (GFTFSHAW);
   b) a heavy chain complementarity determining region 2 (VH-CDR2) comprising the amino acid sequence set forth in SEQ ID NO: 10 (IKAKSDDYAT);
   c) a heavy chain complementarity determining region 3 (VH-CDR3) comprising the amino acid sequence set forth in SEQ ID NO: 15 (TCWEWDLDF);
   d) a light chain complementarity determining region 1 (VL-CDR1) comprising the amino acid sequence set forth in SEQ ID NO: 22 (QSLLDSDGHTY);
   e) a light chain complementarity determining region 2 (VL-CDR2) comprising the amino acid sequence set forth in SEQ ID NO: 26 (SVS); and
   f) a light chain complementarity determining region 3 (VL-CDR3) comprising the amino acid sequence set forth in SEQ ID NO: 29 (MQATHAPPYT).

2. The recombinant antibody of claim 1, wherein the recombinant antibody binds to glycosylated LIF.

3. The recombinant antibody of claim 1, wherein the recombinant antibody is humanized.

4. The recombinant antibody of claim 1, wherein the recombinant antibody is deimmunized.

5. The recombinant antibody of claim 1, wherein the recombinant antibody comprises two heavy chains and two light chains.

6. The recombinant antibody of claim 1, wherein the recombinant antibody is an IgG antibody.

7. The recombinant antibody of claim 1, wherein the recombinant antibody is a Fab, F(ab)$_2$, single-domain antibody, a single chain variable fragment (scFv), or a nanobody.

8. The recombinant antibody of claim 1, wherein the VH-CDR1 comprises the amino acid sequence set forth in SEQ ID NO: 1 (GFTFSHAWMH), the VH-CDR2 comprises the amino acid sequence set forth in SEQ ID NO: 9 (QIKAKSDDYATYYAESVKG), and the VH-CDR3 comprises the amino acid sequence set forth in SEQ ID NO: 15 (TCWEWDLDF), and wherein the VL-CDR1 comprises the amino acid sequence set forth in SEQ ID NO: 21 (RSSQSLLDSDGHTYLN), the VL-CDR2 comprises the amino acid sequence set forth in SEQ ID NO: 25 (SVSNLES), and the VL-CDR3 comprises the amino acid sequence set forth in SEQ ID NO: 29 (MQATHAPPYT).

9. The recombinant antibody of claim 1, wherein the heavy chain comprises a VH sequence at least 90% identical to the amino acid sequence set forth in SEQ ID NO: 72; and the light chain comprises a VL sequence at least 90% identical to the amino acid sequence set forth in SEQ ID NO: 76.

10. The recombinant antibody of claim 9, wherein the VH sequence is at least 95% identical to the amino acid sequence set forth in SEQ ID NO: 72; and the VL sequence is at least 95% identical to the amino acid sequence set forth in SEQ ID NO: 76.

11. The recombinant antibody of claim 9, wherein the VH sequence comprises the amino acid sequence set forth in SEQ ID NO: 72, and the VL sequence comprises the amino acid sequence set forth in SEQ ID NO: 76.

12. The recombinant antibody of claim 1, wherein the heavy chain comprises a sequence at least 90% identical to the amino acid sequence set forth in SEQ ID NO: 88; and the light chain comprises a sequence at least 90% identical to the amino acid sequence set forth in SEQ ID NO: 92.

13. The recombinant antibody of claim 12, wherein the heavy chain comprises the sequence at least 95% identical to the amino acid sequence set forth in SEQ ID NO: 88; and the light chain comprises the sequence at least 95% identical to the amino acid sequence set forth in SEQ ID NO: 92.

14. The recombinant antibody of claim 13, wherein the heavy chain comprises the amino acid sequence set forth in SEQ ID NO: 88; and the light chain comprises the amino acid sequence set forth in SEQ ID NO: 92.

15. A pharmaceutical composition comprising the recombinant antibody of claim 1 and a pharmaceutically acceptable carrier.

16. The pharmaceutical composition of claim 15, formulated for intravenous injection.

17. The pharmaceutical composition of claim 15, wherein the pharmaceutical composition is in lyophilized form.

* * * * *

SEQUENCE LISTING

<160> NUMBER OF SEQ ID NOS: 98

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Phe Thr Phe Ser His Ala Trp Met His
1               5                   10

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Phe Thr Phe Ser His Ala Trp
1               5

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

His Ala Trp Met His
1               5

<210> SEQ ID NO 4
<211> LENGTH: 10

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Phe Thr Phe Ser Asn Ala Trp Met His
1               5                   10

<210> SEQ ID NO 5
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gly Phe Thr Phe Ser Asn Ala Trp
1               5

<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Asn Ala Trp Met His
1               5

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ser Lys Phe Met Tyr
1               5

<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ser Asn Phe Ile His
1               5

<210> SEQ ID NO 9
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gln Ile Lys Ala Lys Ser Asp Asp Tyr Ala Thr Tyr Tyr Ala Glu Ser
```

```
                    1               5               10              15
Val Lys Gly

<210> SEQ ID NO 10
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Ile Lys Ala Lys Ser Asp Asp Tyr Ala Thr
1               5                   10

<210> SEQ ID NO 11
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gln Ile Lys Asp Lys Ser Asp Asn Tyr Ala Thr Tyr Tyr Ala Glu Ser
1               5                   10                  15

Val Lys Gly

<210> SEQ ID NO 12
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Ile Lys Asp Lys Ser Asp Asn Tyr Ala Thr
1               5                   10

<210> SEQ ID NO 13
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Trp Ile Tyr Pro Gly Asp Gly Asp Thr Glu Tyr Asn Gln Lys Phe Ser
1               5                   10                  15

Glu

<210> SEQ ID NO 14
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Trp Ile Tyr Pro Gly Asp Gly Asp Ile Glu Tyr Asn Gln Lys Phe Ile
1               5                   10                  15

Gly
```

<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Thr Cys Trp Glu Trp Asp Leu Asp Phe
1               5

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Trp Glu Trp Asp Leu Asp Phe
1               5

<210> SEQ ID NO 17
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Thr Cys Trp Glu Trp Tyr Leu Asp Phe
1               5

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Trp Glu Trp Tyr Leu Asp Phe
1               5

<210> SEQ ID NO 19
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Arg Asp Tyr His Ser Ser His Phe Ala Tyr
1               5                   10

<210> SEQ ID NO 20
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 20

His Tyr Ser Ser Ser Met Asp Ala
1               5

<210> SEQ ID NO 21
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Arg Ser Ser Gln Ser Leu Leu Asp Ser Asp Gly His Thr Tyr Leu Asn
1               5                   10                  15

<210> SEQ ID NO 22
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gln Ser Leu Leu Asp Ser Asp Gly His Thr Tyr
1               5                   10

<210> SEQ ID NO 23
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Arg Ser Ser Gln Ser Leu Leu His Asn Asn Gly Asn Thr Tyr Leu Ser
1               5                   10                  15

<210> SEQ ID NO 24
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Arg Ser Ser Gln Ser Leu Val His Ser Asn Gly Asn Thr Phe Leu Ser
1               5                   10                  15

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Ser Val Ser Asn Leu Glu Ser
1               5

<210> SEQ ID NO 26
<211> LENGTH: 3
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Ser Val Ser
1

<210> SEQ ID NO 27
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Gln Val Ser Asn Arg Phe Ser
1               5

<210> SEQ ID NO 28
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Lys Val Ser Asn Arg Phe Ser
1               5

<210> SEQ ID NO 29
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Met Gln Ala Thr His Ala Pro Pro Tyr Thr
1               5                   10

<210> SEQ ID NO 30
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Gly Gln Gly Thr Gln Tyr Pro Tyr Thr
1               5

<210> SEQ ID NO 31
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Gly Gln Gly Thr Gln Tyr Pro Phe Thr
```

<210> SEQ ID NO 32
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Ser Gly Tyr Tyr Trp Asn
1               5

<210> SEQ ID NO 33
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Thr Ala Gly Met Gln
1               5

<210> SEQ ID NO 34
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Cys Ile Ser Tyr Asp Gly Arg Asn Asn Tyr Asn Pro Ser Leu Lys Asn
1               5                   10                  15

<210> SEQ ID NO 35
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Trp Ile Asn Thr Gln Ser Gly Glu Pro Gln Tyr Val Asp Asp Phe Arg
1               5                   10                  15

Gly

<210> SEQ ID NO 36
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Arg Tyr Arg Tyr Tyr Asn Tyr Gly Ser Tyr Tyr Ala Val Asp Tyr
1               5                   10                  15

<210> SEQ ID NO 37
<211> LENGTH: 12
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 37

Trp Ala Leu Tyr Ser Glu Tyr Asp Val Met Asp Tyr
1               5                   10

<210> SEQ ID NO 38
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Arg Ala Ser Glu Asn Ile Asp Gly Tyr Leu Glu
1               5                   10

<210> SEQ ID NO 39
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Lys Ala Ser Glu Asn Val Asp Ser Tyr Val Ser
1               5                   10

<210> SEQ ID NO 40
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Ala Ala Thr Leu Leu Ala Asp
1               5

<210> SEQ ID NO 41
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Gly Ala Ser Asn Arg Tyr Thr
1               5

<210> SEQ ID NO 42
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Gln His Tyr Tyr Asn Thr Pro Leu Thr
1               5
```

<210> SEQ ID NO 43
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Gly Gln Ser Tyr Arg Tyr Pro Pro Thr
1               5

<210> SEQ ID NO 44
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Glu Val Gln Leu Val Glu Ser Gly Gly Gly Leu Val Lys Pro Gly Gly
1               5                   10                  15

Ser Leu Lys Leu Ser Cys Ala Ala Ser
            20                  25

<210> SEQ ID NO 45
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Gln Val Gln Leu Gln Glu Ser Gly Gly Gly Leu Val Lys Pro Gly Gly
1               5                   10                  15

Ser Leu Arg Leu Ser Cys Ala Ala Ser
            20                  25

<210> SEQ ID NO 46
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Glu Val Gln Leu Val Glu Ser Gly Gly Gly Val Val Gln Pro Gly Arg
1               5                   10                  15

Ser Leu Arg Leu Ser Cys Ala Ala Ser
            20                  25

<210> SEQ ID NO 47
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Glu Val Gln Leu Met Glu Ser Gly Gly Gly Leu Val Lys Pro Gly Gly
1               5                   10                  15

Ser Leu Arg Leu Ser Cys Ala Thr Ser
            20                  25

<210> SEQ ID NO 48
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Trp Val Arg Gln Ala Pro Gly Lys Gly Leu Glu Trp Val Ala
1               5                   10

<210> SEQ ID NO 49
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Trp Val Arg Gln Ala Pro Gly Lys Gly Leu Glu Trp Val Gly
1               5                   10

<210> SEQ ID NO 50
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Arg Phe Thr Ile Ser Arg Asp Asp Ser Lys Asn Thr Leu Tyr Leu Gln
1               5                   10                  15
Met Asn Ser Leu Lys Thr Glu Asp Thr Ala Val Tyr Tyr Cys
            20                  25                  30

<210> SEQ ID NO 51
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Arg Phe Ser Ile Ser Arg Asp Asn Ala Lys Asn Ser Leu Tyr Leu Gln
1               5                   10                  15
Met Asn Ser Leu Arg Val Glu Asp Thr Val Val Tyr Tyr Cys
            20                  25                  30

<210> SEQ ID NO 52
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Arg Phe Thr Ile Ser Arg Asp Asp Ser Lys Ser Thr Leu Phe Leu Gln
1               5                   10                  15

Met Asn Asn Leu Lys Thr Glu Asp Thr Ala Val Tyr Tyr Cys
         20                  25                  30

<210> SEQ ID NO 53
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Trp Gly Gln Gly Thr Leu Val Thr Val Ser Ser
1               5                   10

<210> SEQ ID NO 54
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Trp Gly Gln Gly Thr Met Val Thr Val Ser Ser
1               5                   10

<210> SEQ ID NO 55
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Trp Gly Gln Gly Thr Thr Val Thr Val Ser Ser
1               5                   10

<210> SEQ ID NO 56
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Asp Val Val Met Thr Gln Ser Pro Leu Ser Leu Pro Val Thr Leu Gly
1               5                   10                  15

Gln Pro Ala Ser Ile Ser Cys
            20

<210> SEQ ID NO 57
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Asp Ile Val Met Thr Gln Thr Pro Leu Ser Ser Pro Val Thr Leu Gly
1               5                   10                  15

Gln Pro Ala Ser Ile Ser Cys
            20

```
<210> SEQ ID NO 58
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Asp Ile Val Met Thr Gln Thr Pro Leu Ser Leu Ser Val Thr Pro Gly
1               5                   10                  15

Gln Pro Ala Ser Ile Ser Cys
            20

<210> SEQ ID NO 59
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Asp Val Val Met Thr Gln Ser Pro Leu Ser Gln Pro Val Thr Leu Gly
1               5                   10                  15

Gln Pro Ala Ser Ile Ser Cys
            20

<210> SEQ ID NO 60
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Trp Phe Gln Gln Arg Pro Gly Gln Ser Pro Arg Arg Leu Ile Tyr
1               5                   10                  15

<210> SEQ ID NO 61
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Trp Leu Gln Gln Arg Pro Gly Gln Pro Pro Arg Leu Leu Ile Tyr
1               5                   10                  15

<210> SEQ ID NO 62
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Trp Leu Leu Gln Lys Pro Gly Gln Pro Pro Gln Leu Leu Ile Tyr
1               5                   10                  15

<210> SEQ ID NO 63
<211> LENGTH: 15
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Trp Leu Gln Gln Arg Pro Gly Gln Ser Pro Arg Arg Leu Ile Tyr
1               5                   10                  15

<210> SEQ ID NO 64
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Gly Val Pro Asp Arg Phe Ser Gly Ser Gly Ser Gly Thr Asp Phe Thr
1               5                   10                  15

Leu Lys Ile Ser Arg Val Glu Ala Glu Asp Val Gly Leu Tyr Tyr Cys
                20                  25                  30

<210> SEQ ID NO 65
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Gly Val Pro Asp Arg Phe Ser Gly Ser Gly Ala Gly Thr Asp Phe Thr
1               5                   10                  15

Leu Lys Ile Ser Arg Val Glu Ala Glu Asp Val Gly Val Tyr Tyr Cys
                20                  25                  30

<210> SEQ ID NO 66
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Gly Val Pro Asn Arg Phe Ser Gly Ser Gly Ser Gly Thr Asp Phe Thr
1               5                   10                  15

Leu Lys Ile Ser Arg Val Glu Ala Glu Asp Val Gly Leu Tyr Tyr Cys
                20                  25                  30

<210> SEQ ID NO 67
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Gly Val Pro Asp Arg Phe Asn Gly Ser Gly Ser Gly Thr Asp Phe Thr
1               5                   10                  15

Leu Ser Ile Ser Arg Val Glu Ala Glu Asp Val Gly Val Tyr Tyr Cys
                20                  25                  30
```

<210> SEQ ID NO 68
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Phe Gly Gln Gly Thr Lys Leu Glu Ile Lys
1               5                   10

<210> SEQ ID NO 69
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Phe Gly Gly Gly Thr Lys Val Glu Ile Lys
1               5                   10

<210> SEQ ID NO 70
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Phe Gly Gln Gly Thr Lys Val Glu Ile Lys
1               5                   10

<210> SEQ ID NO 71
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser His Ala
            20                  25                  30

Trp Met His Trp Val Arg Gln Ala Pro Gly Lys Gly Leu Glu Trp Val
        35                  40                  45

Ala Gln Ile Lys Ala Lys Ser Asp Asp Tyr Ala Thr Tyr Tyr Ala Glu
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Cys Trp Glu Trp Asp Leu Asp Phe Trp Gly Gln Gly Thr
            100                 105                 110

Leu Val Thr Val Ser Ser
        115

<210> SEQ ID NO 72

```
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Gln Val Gln Leu Gln Glu Ser Gly Gly Gly Leu Val Lys Pro Gly Gly
1               5                   10                  15

Ser Leu Arg Leu Ser Cys Ala Ala Ser Gly Phe Thr Phe Ser His Ala
            20                  25                  30

Trp Met His Trp Val Arg Gln Ala Pro Gly Lys Gly Leu Glu Trp Val
        35                  40                  45

Gly Gln Ile Lys Ala Lys Ser Asp Asp Tyr Ala Thr Tyr Tyr Ala Glu
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Cys Trp Glu Trp Asp Leu Asp Phe Trp Gly Gln Gly Thr
            100                 105                 110

Met Val Thr Val Ser Ser
        115

<210> SEQ ID NO 73
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser His Ala
            20                  25                  30

Trp Met His Trp Val Arg Gln Ala Pro Gly Lys Gly Leu Glu Trp Val
        35                  40                  45

Ala Gln Ile Lys Ala Lys Ser Asp Asp Tyr Ala Thr Tyr Tyr Ala Glu
    50                  55                  60

Ser Val Lys Gly Arg Phe Ser Ile Ser Arg Asp Asn Ala Lys Asn Ser
65                  70                  75                  80

Leu Tyr Leu Gln Met Asn Ser Leu Arg Val Glu Asp Thr Val Val Tyr
                85                  90                  95

Tyr Cys Thr Cys Trp Glu Trp Asp Leu Asp Phe Trp Gly Gln Gly Thr
            100                 105                 110

Thr Val Thr Val Ser Ser
        115

<210> SEQ ID NO 74
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74
```

```
Glu Val Gln Leu Met Glu Ser Gly Gly Gly Leu Val Lys Pro Gly Gly
1               5                   10                  15

Ser Leu Arg Leu Ser Cys Ala Thr Ser Gly Phe Thr Phe Ser His Ala
            20                  25                  30

Trp Met His Trp Val Arg Gln Ala Pro Gly Lys Gly Leu Glu Trp Val
            35                  40                  45

Gly Gln Ile Lys Ala Lys Ser Asp Asp Tyr Ala Thr Tyr Tyr Ala Glu
        50                  55                  60

Ser Val Lys Gly Arg Phe Thr Ile Ser Arg Asp Ser Lys Ser Thr
65                  70                  75                  80

Leu Phe Leu Gln Met Asn Asn Leu Lys Thr Glu Asp Thr Ala Val Tyr
                85                  90                  95

Tyr Cys Thr Cys Trp Glu Trp Asp Leu Asp Phe Trp Gly Gln Gly Thr
            100                 105                 110

Leu Val Thr Val Ser Ser
            115

<210> SEQ ID NO 75
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Leu Asp Ser
            20                  25                  30

Asp Gly His Thr Tyr Leu Asn Trp Phe Gln Gln Arg Pro Gly Gln Ser
            35                  40                  45

Pro Arg Arg Leu Ile Tyr Ser Val Ser Asn Leu Glu Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Leu Tyr Tyr Cys Met Gln Ala
                85                  90                  95

Thr His Ala Pro Pro Tyr Thr Phe Gly Gln Gly Thr Lys Leu Glu Ile
            100                 105                 110

Lys

<210> SEQ ID NO 76
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Leu Asp Ser
            20                  25                  30

Asp Gly His Thr Tyr Leu Asn Trp Leu Gln Gln Arg Pro Gly Gln Pro
            35                  40                  45

Pro Arg Leu Leu Ile Tyr Ser Val Ser Asn Leu Glu Ser Gly Val Pro
```

```
            50                  55                  60
Asp Arg Phe Ser Gly Ser Gly Ala Gly Thr Asp Phe Thr Leu Lys Ile
 65                  70                  75                  80

Ser Arg Val Glu Ala Glu Asp Val Gly Val Tyr Tyr Cys Met Gln Ala
                 85                  90                  95

Thr His Ala Pro Pro Tyr Thr Phe Gly Gln Gly Thr Lys Leu Glu Ile
            100                 105                 110

Lys

<210> SEQ ID NO 77
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Asp Ile Val Met Thr Gln Thr Pro Leu Ser Leu Ser Val Thr Pro Gly
 1               5                  10                  15

Gln Pro Ala Ser Ile Ser Cys Arg Ser Ser Gln Ser Leu Leu Asp Ser
             20                  25                  30

Asp Gly His Thr Tyr Leu Asn Trp Leu Leu Gln Lys Pro Gly Gln Pro
         35                  40                  45

Pro Gln Leu Leu Ile Tyr Ser Val Ser Asn Leu Glu Ser Gly Val Pro
     50                  55                  60

Asn Arg Phe Ser Gly Ser Gly Ser Gly Thr Asp Phe Thr Leu Lys Ile
 65                  70                  75                  80

Ser Arg Val Glu Ala Glu Asp Val Gly Leu Tyr Tyr Cys Met Gln Ala
                 85                  90                  95

Thr His Ala Pro Pro Tyr Thr Phe Gly Gly Gly Thr Lys Val Glu Ile
            100                 105                 110

Lys

<210> SEQ ID NO 78
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Asp Val Val Met Thr Gln Ser Pro Leu Ser Gln Pro Val Thr Leu Gly
 1               5                  10                  15

Gln Pro Ala Ser Ile Ser Cys Arg Ser Ser Gln Ser Leu Leu Asp Ser
             20                  25                  30

Asp Gly His Thr Tyr Leu Asn Trp Leu Gln Gln Arg Pro Gly Gln Ser
         35                  40                  45

Pro Arg Arg Leu Ile Tyr Ser Val Ser Asn Leu Glu Ser Gly Val Pro
     50                  55                  60

Asp Arg Phe Asn Gly Ser Gly Ser Gly Thr Asp Phe Thr Leu Ser Ile
 65                  70                  75                  80

Ser Arg Val Glu Ala Glu Asp Val Gly Val Tyr Tyr Cys Met Gln Ala
                 85                  90                  95

Thr His Ala Pro Pro Tyr Thr Phe Gly Gln Gly Thr Lys Val Glu Ile
            100                 105                 110
```

Lys

<210> SEQ ID NO 79
<211> LENGTH: 467
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Met Gly Trp Thr Leu Val Phe Leu Phe Leu Leu Ser Val Thr Ala Gly
1               5                   10                  15

Val His Ser Glu Val Gln Leu Val Glu Ser Gly Gly Gly Leu Val Lys
                20                  25                  30

Pro Gly Gly Ser Leu Lys Leu Ser Cys Ala Ala Ser Gly Phe Thr Phe
            35                  40                  45

Ser His Ala Trp Met His Trp Val Arg Gln Ala Pro Gly Lys Gly Leu
        50                  55                  60

Glu Trp Val Ala Gln Ile Lys Ala Lys Ser Asp Asp Tyr Ala Thr Tyr
65                  70                  75                  80

Tyr Ala Glu Ser Val Lys Gly Arg Phe Thr Ile Ser Arg Asp Asp Ser
                85                  90                  95

Lys Asn Thr Leu Tyr Leu Gln Met Asn Ser Leu Lys Thr Glu Asp Thr
            100                 105                 110

Ala Val Tyr Tyr Cys Thr Cys Trp Glu Trp Asp Leu Asp Phe Trp Gly
        115                 120                 125

Gln Gly Thr Leu Val Thr Val Ser Ser Ala Ser Thr Lys Gly Pro Ser
130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

-continued

```
Glu Lys Thr Ile Ser Lys Ala Lys Gly Gln Pro Arg Glu Pro Gln Val
            355                 360                 365

Tyr Thr Leu Pro Pro Ser Arg Asp Glu Leu Thr Lys Asn Gln Val Ser
370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
                420                 425                 430

Asp Lys Ser Arg Trp Gln Gln Gly Asn Val Phe Ser Cys Ser Val Met
            435                 440                 445

His Glu Ala Leu His Asn His Tyr Thr Gln Lys Ser Leu Ser Leu Ser
        450                 455                 460

Pro Gly Lys
465

<210> SEQ ID NO 80
<211> LENGTH: 467
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Met Gly Trp Thr Leu Val Phe Leu Phe Leu Leu Ser Val Thr Ala Gly
1               5                   10                  15

Val His Ser Gln Val Gln Leu Gln Glu Ser Gly Gly Gly Leu Val Lys
            20                  25                  30

Pro Gly Gly Ser Leu Arg Leu Ser Cys Ala Ala Ser Gly Phe Thr Phe
        35                  40                  45

Ser His Ala Trp Met His Trp Val Arg Gln Ala Pro Gly Lys Gly Leu
    50                  55                  60

Glu Trp Val Gly Gln Ile Lys Ala Lys Ser Asp Asp Tyr Ala Thr Tyr
65                  70                  75                  80

Tyr Ala Glu Ser Val Lys Gly Arg Phe Thr Ile Ser Arg Asp Asp Ser
                85                  90                  95

Lys Asn Thr Leu Tyr Leu Gln Met Asn Ser Leu Lys Thr Glu Asp Thr
            100                 105                 110

Ala Val Tyr Tyr Cys Thr Cys Trp Glu Trp Asp Leu Asp Phe Trp Gly
        115                 120                 125

Gln Gly Thr Met Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Lys Val Glu Pro Lys Ser Cys
225                 230                 235                 240
```

```
Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
            275                 280                 285

Glu Asp Pro Glu Val Lys Phe Asn Trp Tyr Val Asp Gly Val Glu Val
290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
            355                 360                 365

Tyr Thr Leu Pro Pro Ser Arg Asp Glu Leu Thr Lys Asn Gln Val Ser
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
            435                 440                 445

His Glu Ala Leu His Asn His Tyr Thr Gln Lys Ser Leu Ser Leu Ser
450                 455                 460

Pro Gly Lys
465

<210> SEQ ID NO 81
<211> LENGTH: 467
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Met Gly Trp Thr Leu Val Phe Leu Phe Leu Leu Ser Val Thr Ala Gly
1               5                   10                  15

Val His Ser Glu Val Gln Leu Val Glu Ser Gly Gly Gly Val Val Gln
            20                  25                  30

Pro Gly Arg Ser Leu Arg Leu Ser Cys Ala Ala Ser Gly Phe Thr Phe
        35                  40                  45

Ser His Ala Trp Met His Trp Val Arg Gln Ala Pro Gly Lys Gly Leu
    50                  55                  60

Glu Trp Val Ala Gln Ile Lys Ala Lys Ser Asp Asp Tyr Ala Thr Tyr
65                  70                  75                  80

Tyr Ala Glu Ser Val Lys Gly Arg Phe Ser Ile Ser Arg Asp Asn Ala
                85                  90                  95

Lys Asn Ser Leu Tyr Leu Gln Met Asn Ser Leu Arg Val Glu Asp Thr
            100                 105                 110

Val Val Tyr Tyr Cys Thr Cys Trp Glu Trp Asp Leu Asp Phe Trp Gly
```

|   |   |   | 115 |   |   |   | 120 |   |   |   | 125 |   |   |
|---|---|---|---|---|---|---|---|---|---|---|---|---|---|

Gln Gly Thr Thr Val Thr Val Ser Ser Ala Ser Thr Lys Gly Pro Ser
130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
210                 215                 220

Lys Pro Ser Asn Thr Lys Val Asp Lys Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Asp Glu Leu Thr Lys Asn Gln Val Ser
370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
450                 455                 460

Pro Gly Lys
465

<210> SEQ ID NO 82
<211> LENGTH: 467
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Met Gly Trp Thr Leu Val Phe Leu Phe Leu Ser Val Thr Ala Gly
1               5                   10                  15

Val His Ser Glu Val Gln Leu Met Glu Ser Gly Gly Gly Leu Val Lys
        20                  25                  30

Pro Gly Gly Ser Leu Arg Leu Ser Cys Ala Thr Ser Gly Phe Thr Phe
            35                  40                  45

Ser His Ala Trp Met His Trp Val Arg Gln Ala Pro Gly Lys Gly Leu
    50                  55                  60

Glu Trp Val Gly Gln Ile Lys Ala Lys Ser Asp Asp Tyr Ala Thr Tyr
65                  70                  75                  80

Tyr Ala Glu Ser Val Lys Gly Arg Phe Thr Ile Ser Arg Asp Asp Ser
                85                  90                  95

Lys Ser Thr Leu Phe Leu Gln Met Asn Asn Leu Lys Thr Glu Asp Thr
            100                 105                 110

Ala Val Tyr Tyr Cys Thr Cys Trp Glu Trp Asp Leu Asp Phe Trp Gly
        115                 120                 125

Gln Gly Thr Leu Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Lys Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Asp Glu Leu Thr Lys Asn Gln Val Ser
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val

<210> SEQ ID NO 83
<211> LENGTH: 240
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 83

```
Met Val Ser Ser Ala Gln Phe Leu Gly Leu Leu Leu Leu Cys Phe Gln
 1               5                   10                  15

Gly Thr Arg Cys Asp Val Val Met Thr Gln Ser Pro Leu Ser Leu Pro
             20                  25                  30

Val Thr Leu Gly Gln Pro Ala Ser Ile Ser Cys Arg Ser Ser Gln Ser
         35                  40                  45

Leu Leu Asp Ser Asp Gly His Thr Tyr Leu Asn Trp Phe Gln Gln Arg
     50                  55                  60

Pro Gly Gln Ser Pro Arg Arg Leu Ile Tyr Ser Val Ser Asn Leu Glu
 65                  70                  75                  80

Ser Gly Val Pro Asp Arg Phe Ser Gly Ser Gly Ser Gly Thr Asp Phe
                 85                  90                  95

Thr Leu Lys Ile Ser Arg Val Glu Ala Glu Asp Val Gly Leu Tyr Tyr
            100                 105                 110

Cys Met Gln Ala Thr His Ala Pro Pro Tyr Thr Phe Gly Gln Gly Thr
        115                 120                 125

Lys Leu Glu Ile Lys Arg Thr Val Ala Ala Pro Ser Val Phe Ile Phe
    130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
    210                 215                 220

Gln Gly Leu Ser Ser Pro Val Thr Lys Ser Phe Asn Arg Gly Glu Cys
225                 230                 235                 240
```

<210> SEQ ID NO 84
<211> LENGTH: 240
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 84

```
Met Val Ser Ser Ala Gln Phe Leu Gly Leu Leu Leu Leu Cys Phe Gln
```

(preceding continued sequence)

```
                                                            Asp Lys Ser Arg Trp Gln Gln Gly Asn Val Phe Ser Cys Ser Val Met
                        420                 425                 430

His Glu Ala Leu His Asn His Tyr Thr Gln Lys Ser Leu Ser Leu Ser
    435                 440                 445

Pro Gly Lys
450                 455                 460

465
```

```
            1               5                  10                 15
Gly Thr Arg Cys Asp Ile Val Met Thr Gln Thr Pro Leu Ser Ser Pro
                20                  25                  30

Val Thr Leu Gly Gln Pro Ala Ser Ile Ser Cys Arg Ser Ser Gln Ser
                35                  40                  45

Leu Leu Asp Ser Asp Gly His Thr Tyr Leu Asn Trp Leu Gln Gln Arg
      50                  55                  60

Pro Gly Gln Pro Pro Arg Leu Leu Ile Tyr Ser Val Ser Asn Leu Glu
65                  70                  75                  80

Ser Gly Val Pro Asp Arg Phe Ser Gly Ser Gly Ala Gly Thr Asp Phe
                85                  90                  95

Thr Leu Lys Ile Ser Arg Val Glu Ala Glu Asp Val Gly Val Tyr Tyr
                100                 105                 110

Cys Met Gln Ala Thr His Ala Pro Pro Tyr Thr Phe Gly Gln Gly Thr
                115                 120                 125

Lys Leu Glu Ile Lys Arg Thr Val Ala Ala Pro Ser Val Phe Ile Phe
      130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
                180                 185                 190

Asp Ser Lys Asp Ser Thr Tyr Ser Leu Ser Ser Thr Leu Thr Leu Ser
                195                 200                 205

Lys Ala Asp Tyr Glu Lys His Lys Val Tyr Ala Cys Glu Val Thr His
      210                 215                 220

Gln Gly Leu Ser Ser Pro Val Thr Lys Ser Phe Asn Arg Gly Glu Cys
225                 230                 235                 240

<210> SEQ ID NO 85
<211> LENGTH: 240
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

Met Val Ser Ser Ala Gln Phe Leu Gly Leu Leu Leu Cys Phe Gln
1               5                   10                  15

Gly Thr Arg Cys Asp Ile Val Met Thr Gln Thr Pro Leu Ser Leu Ser
                20                  25                  30

Val Thr Pro Gly Gln Pro Ala Ser Ile Ser Cys Arg Ser Ser Gln Ser
                35                  40                  45

Leu Leu Asp Ser Asp Gly His Thr Tyr Leu Asn Trp Leu Leu Gln Lys
      50                  55                  60

Pro Gly Gln Pro Pro Gln Leu Leu Ile Tyr Ser Val Ser Asn Leu Glu
65                  70                  75                  80

Ser Gly Val Pro Asn Arg Phe Ser Gly Ser Gly Ser Gly Thr Asp Phe
                85                  90                  95

Thr Leu Lys Ile Ser Arg Val Glu Ala Glu Asp Val Gly Leu Tyr Tyr
                100                 105                 110

Cys Met Gln Ala Thr His Ala Pro Pro Tyr Thr Phe Gly Gly Gly Thr
                115                 120                 125
```

Lys Val Glu Ile Lys Arg Thr Val Ala Ala Pro Ser Val Phe Ile Phe
130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
210                 215                 220

Gln Gly Leu Ser Ser Pro Val Thr Lys Ser Phe Asn Arg Gly Glu Cys
225                 230                 235                 240

<210> SEQ ID NO 86
<211> LENGTH: 240
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

Met Val Ser Ser Ala Gln Phe Leu Gly Leu Leu Leu Leu Cys Phe Gln
1               5                   10                  15

Gly Thr Arg Cys Asp Val Val Met Thr Gln Ser Pro Leu Ser Gln Pro
            20                  25                  30

Val Thr Leu Gly Gln Pro Ala Ser Ile Ser Cys Arg Ser Ser Gln Ser
        35                  40                  45

Leu Leu Asp Ser Asp Gly His Thr Tyr Leu Asn Trp Leu Gln Gln Arg
    50                  55                  60

Pro Gly Gln Ser Pro Arg Arg Leu Ile Tyr Ser Val Ser Asn Leu Glu
65                  70                  75                  80

Ser Gly Val Pro Asp Arg Phe Ser Gly Ser Gly Ser Gly Thr Asp Phe
                85                  90                  95

Thr Leu Ser Ile Ser Arg Val Glu Ala Glu Asp Val Gly Val Tyr Tyr
            100                 105                 110

Cys Met Gln Ala Thr His Ala Pro Pro Tyr Thr Phe Gly Gln Gly Thr
        115                 120                 125

Lys Val Glu Ile Lys Arg Thr Val Ala Ala Pro Ser Val Phe Ile Phe
130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
210                 215                 220

Gln Gly Leu Ser Ser Pro Val Thr Lys Ser Phe Asn Arg Gly Glu Cys
225                 230                 235                 240

<210> SEQ ID NO 87

<211> LENGTH: 448
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 87

```
Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser His Ala
            20                  25                  30

Trp Met His Trp Val Arg Gln Ala Pro Gly Lys Gly Leu Glu Trp Val
        35                  40                  45

Ala Gln Ile Lys Ala Lys Ser Asp Asp Tyr Ala Thr Tyr Tyr Ala Glu
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Cys Trp Glu Trp Asp Leu Asp Phe Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
```

```
                    370                 375                 380
Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 88
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Gln Val Gln Leu Gln Glu Ser Gly Gly Gly Leu Val Lys Pro Gly Gly
1               5                   10                  15

Ser Leu Arg Leu Ser Cys Ala Ala Ser Gly Phe Thr Phe Ser His Ala
            20                  25                  30

Trp Met His Trp Val Arg Gln Ala Pro Gly Lys Gly Leu Glu Trp Val
        35                  40                  45

Gly Gln Ile Lys Ala Lys Ser Asp Asp Tyr Ala Thr Tyr Tyr Ala Glu
    50                  55                  60

Ser Val Lys Gly Arg Phe Thr Ile Ser Arg Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Cys Trp Glu Trp Asp Leu Asp Phe Trp Gly Gln Gly Thr
            100                 105                 110

Met Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285
```

```
Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Arg Asp Glu Leu Thr Lys Asn Gln Val Ser Leu Thr Cys
            355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Lys
            435                 440                 445

<210> SEQ ID NO 89
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser His Ala
            20                  25                  30

Trp Met His Trp Val Arg Gln Ala Pro Gly Lys Gly Leu Glu Trp Val
        35                  40                  45

Ala Gln Ile Lys Ala Lys Ser Asp Asp Tyr Ala Thr Tyr Tyr Ala Glu
    50                  55                  60

Ser Val Lys Gly Arg Phe Ser Ile Ser Arg Asp Asn Ala Lys Asn Ser
65                  70                  75                  80

Leu Tyr Leu Gln Met Asn Ser Leu Arg Val Glu Asp Thr Val Val Tyr
                85                  90                  95

Tyr Cys Thr Cys Trp Glu Trp Asp Leu Asp Phe Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205
```

Asn Thr Lys Val Asp Lys Lys Val Glu Pro Lys Ser Cys Asp Lys Thr
            210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 90
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

Glu Val Gln Leu Met Glu Ser Gly Gly Gly Leu Val Lys Pro Gly Gly
1               5                   10                  15

Ser Leu Arg Leu Ser Cys Ala Thr Ser Gly Phe Thr Phe Ser His Ala
            20                  25                  30

Trp Met His Trp Val Arg Gln Ala Pro Gly Lys Gly Leu Glu Trp Val
        35                  40                  45

Gly Gln Ile Lys Ala Lys Ser Asp Asp Tyr Ala Thr Tyr Tyr Ala Glu
    50                  55                  60

Ser Val Lys Gly Arg Phe Thr Ile Ser Arg Asp Asp Ser Lys Ser Thr
65                  70                  75                  80

Leu Phe Leu Gln Met Asn Asn Leu Lys Thr Glu Asp Thr Ala Val Tyr
                85                  90                  95

Tyr Cys Thr Cys Trp Glu Trp Asp Leu Asp Phe Trp Gly Gln Gly Thr
            100                 105                 110

Leu Val Thr Val Ser Ser Ala Ser Thr Lys Gly Pro Ser Val Phe Pro

```
                    115                 120                 125
Leu Ala Pro Ser Ser Lys Ser Thr Ser Gly Gly Thr Ala Ala Leu Gly
            130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
        210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445
```

<210> SEQ ID NO 91
<211> LENGTH: 220
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91

```
Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Leu Asp Ser
            20                  25                  30
```

```
Asp Gly His Thr Tyr Leu Asn Trp Phe Gln Gln Arg Pro Gly Gln Ser
            35                  40                  45

Pro Arg Arg Leu Ile Tyr Ser Val Ser Asn Leu Glu Ser Gly Val Pro
 50                      55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Leu Tyr Tyr Cys Met Gln Ala
                 85                  90                  95

Thr His Ala Pro Pro Tyr Thr Phe Gly Gln Gly Thr Lys Leu Glu Ile
            100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
            195                 200                 205

Ser Pro Val Thr Lys Ser Phe Asn Arg Gly Glu Cys
            210                 215                 220

<210> SEQ ID NO 92
<211> LENGTH: 220
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

Asp Ile Val Met Thr Gln Thr Pro Leu Ser Ser Pro Val Thr Leu Gly
 1               5                  10                  15

Gln Pro Ala Ser Ile Ser Cys Arg Ser Ser Gln Ser Leu Leu Asp Ser
             20                  25                  30

Asp Gly His Thr Tyr Leu Asn Trp Leu Gln Gln Arg Pro Gly Gln Pro
            35                  40                  45

Pro Arg Leu Leu Ile Tyr Ser Val Ser Asn Leu Glu Ser Gly Val Pro
 50                  55                  60

Asp Arg Phe Ser Gly Ser Gly Ala Gly Thr Asp Phe Thr Leu Lys Ile
 65                  70                  75                  80

Ser Arg Val Glu Ala Glu Asp Val Gly Val Tyr Tyr Cys Met Gln Ala
                 85                  90                  95

Thr His Ala Pro Pro Tyr Thr Phe Gly Gln Gly Thr Lys Leu Glu Ile
            100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175
```

```
Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 93
<211> LENGTH: 220
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 93

Asp Ile Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Leu Asp Ser
            20                  25                  30

Asp Gly His Thr Tyr Leu Asn Trp Leu Leu Gln Lys Pro Gly Gln Pro
        35                  40                  45

Pro Gln Leu Leu Ile Tyr Ser Val Ser Asn Leu Glu Ser Gly Val Pro
    50                  55                  60

Asn Arg Phe Ser Gly Ser Gly Ser Gly Thr Asp Phe Thr Leu Lys Ile
65                  70                  75                  80

Ser Arg Val Glu Ala Glu Asp Val Gly Leu Tyr Tyr Cys Met Gln Ala
                85                  90                  95

Thr His Ala Pro Pro Tyr Thr Phe Gly Gly Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 94
<211> LENGTH: 220
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

Asp Val Val Met Thr Gln Ser Pro Leu Ser Gln Pro Val Thr Leu Gly
1               5                   10                  15

Gln Pro Ala Ser Ile Ser Cys Arg Ser Ser Gln Ser Leu Leu Asp Ser
            20                  25                  30
```

```
Asp Gly His Thr Tyr Leu Asn Trp Leu Gln Gln Arg Pro Gly Gln Ser
            35                  40                  45

Pro Arg Leu Ile Tyr Ser Val Ser Asn Leu Glu Ser Gly Val Pro
 50                  55                  60

Asp Arg Phe Ser Gly Ser Gly Ser Gly Thr Asp Phe Thr Leu Ser Ile
 65                  70                  75                  80

Ser Arg Val Glu Ala Glu Asp Val Gly Val Tyr Tyr Cys Met Gln Ala
                 85                  90                  95

Thr His Ala Pro Pro Tyr Thr Phe Gly Gln Gly Thr Lys Val Glu Ile
                100                 105                 110

Lys Arg Thr Val Ala Ala Pro Ser Val Phe Ile Phe Pro Pro Ser Asp
                115                 120                 125

Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
                180                 185                 190

Glu Lys His Lys Val Tyr Ala Cys Glu Val Thr His Gln Gly Leu Ser
                195                 200                 205

Ser Pro Val Thr Lys Ser Phe Asn Arg Gly Glu Cys
                210                 215                 220

<210> SEQ ID NO 95
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Thr Ser Trp Glu Trp Asp Leu Asp Phe
1               5

<210> SEQ ID NO 96
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

Gln Val Gln Leu Gln Glu Ser Gly Gly Gly Leu Val Lys Pro Gly Gly
1               5                   10                  15

Ser Leu Arg Leu Ser Cys Ala Ala Ser Gly Phe Thr Phe Ser His Ala
                20                  25                  30

Trp Met His Trp Val Arg Gln Ala Pro Gly Lys Gly Leu Glu Trp Val
                35                  40                  45

Gly Gln Ile Lys Ala Lys Ser Asp Asp Tyr Ala Thr Tyr Tyr Ala Glu
            50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95
```

Tyr Cys Thr Ser Trp Glu Trp Asp Leu Asp Phe Trp Gly Gln Gly Thr
                100                 105                 110

Met Val Thr Val Ser Ser
            115

<210> SEQ ID NO 97
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 97

Gln Val Gln Leu Gln Glu Ser Gly Gly Gly Leu Val Lys Pro Gly Gly
1               5                   10                  15

Ser Leu Arg Leu Ser Cys Ala Ala Ser Gly Phe Thr Phe Ser His Ala
            20                  25                  30

Trp Met His Trp Val Arg Gln Ala Pro Gly Lys Gly Leu Glu Trp Val
        35                  40                  45

Gly Gln Ile Lys Ala Lys Ser Asp Asp Tyr Ala Thr Tyr Tyr Ala Glu
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Ser Trp Glu Trp Asp Leu Asp Phe Trp Gly Gln Gly Thr
            100                 105                 110

Met Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr

```
                  325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
            405                 410                 415

Arg Trp Gln Gln Gly Asn Val Phe Ser Cys Ser Val Met His Glu Ala
        420                 425                 430

Leu His Asn His Tyr Thr Gln Lys Ser Leu Ser Leu Ser Pro Gly Lys
    435                 440                 445

<210> SEQ ID NO 98
<211> LENGTH: 180
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

Ser Pro Leu Pro Ile Thr Pro Val Asn Ala Thr Cys Ala Ile Arg His
1               5                   10                  15

Pro Cys His Asn Asn Leu Met Asn Gln Ile Arg Ser Gln Leu Ala Gln
            20                  25                  30

Leu Asn Gly Ser Ala Asn Ala Leu Phe Ile Leu Tyr Tyr Thr Ala Gln
        35                  40                  45

Gly Glu Pro Phe Pro Asn Asn Leu Asp Lys Leu Cys Gly Pro Asn Val
    50                  55                  60

Thr Asp Phe Pro Pro Phe His Ala Asn Gly Thr Glu Lys Ala Lys Leu
65                  70                  75                  80

Val Glu Leu Tyr Arg Ile Val Val Tyr Leu Gly Thr Ser Leu Gly Asn
                85                  90                  95

Ile Thr Arg Asp Gln Lys Ile Leu Asn Pro Ser Ala Leu Ser Leu His
            100                 105                 110

Ser Lys Leu Asn Ala Thr Ala Asp Ile Leu Arg Gly Leu Leu Ser Asn
        115                 120                 125

Val Leu Cys Arg Leu Cys Ser Lys Tyr His Val Gly His Val Asp Val
    130                 135                 140

Thr Tyr Gly Pro Asp Thr Ser Gly Lys Asp Val Phe Gln Lys Lys Lys
145                 150                 155                 160

Leu Gly Cys Gln Leu Leu Gly Lys Tyr Lys Gln Ile Ile Ala Val Leu
                165                 170                 175

Ala Gln Ala Phe
            180
```